United States Patent
Kang et al.

(10) Patent No.: US 11,512,285 B2
(45) Date of Patent: Nov. 29, 2022

(54) METHOD OF PREPARING INDUCED NEURAL STEM CELLS REPROGRAMMED FROM NON-NEURONAL CELLS USING HMGA2

(71) Applicants: SEOUL NATIONAL UNIVERSITY R&DB FOUNDATION, Seoul (KR); KANGSTEM BIOTECH CO., LTD., Seoul (KR)

(72) Inventors: Kyung Sun Kang, Seoul (KR); Kyung Rok Yu, Seoul (KR)

(73) Assignees: SEOUL NATIONAL UNIVERSITY R&DB FOUNDATION, Seoul (KR); KANGSTEM BIOTECH CO., LTD., Seoul (KR)

( * ) Notice: Subject to any disclaimer, the term of this patent is extended or adjusted under 35 U.S.C. 154(b) by 247 days.

(21) Appl. No.: 14/782,340

(22) PCT Filed: Apr. 4, 2014

(86) PCT No.: PCT/KR2014/002918
§ 371 (c)(1),
(2) Date: Oct. 5, 2015

(87) PCT Pub. No.: WO2014/163425
PCT Pub. Date: Oct. 9, 2014

(65) Prior Publication Data
US 2016/0215259 A1   Jul. 28, 2016

(30) Foreign Application Priority Data

Apr. 6, 2013 (KR) .................. 10-2013-0037790
Jul. 23, 2013 (KR) .................. 10-2013-0087020

(51) Int. Cl.
| | | |
|---|---|---|
| A61K 35/30 | (2015.01) | |
| C12N 5/0797 | (2010.01) | |
| A61K 38/17 | (2006.01) | |
| G01N 33/50 | (2006.01) | |

(52) U.S. Cl.
CPC .......... C12N 5/0623 (2013.01); A61K 35/30 (2013.01); A61K 38/1709 (2013.01); G01N 33/5058 (2013.01); *C12N 2501/602* (2013.01); *C12N 2501/998* (2013.01); *C12N 2502/1352* (2013.01); *C12N 2506/00* (2013.01); *C12N 2506/025* (2013.01); *C12N 2510/00* (2013.01)

(58) Field of Classification Search
CPC .................................................. C12N 5/0623
See application file for complete search history.

(56) References Cited

U.S. PATENT DOCUMENTS

| | | |
|---|---|---|
| 2011/0250684 A1 | 10/2011 | Akamatsu et al. |
| 2012/0269778 A1 | 10/2012 | Huang et al. |
| 2013/0045187 A1 | 2/2013 | Semechkin et al. |

FOREIGN PATENT DOCUMENTS

| | | | |
|---|---|---|---|
| KR | 1020060093269 | 8/2006 | |
| KR | 20110110058 A | 10/2011 | |
| KR | 20130030303 A | 3/2013 | |
| WO | 2011/158967 A1 | 12/2011 | |
| WO | WO-2011158967 A1 * | 12/2011 | .......... C12N 5/0696 |
| WO | 2012022725 A2 | 2/2012 | |
| WO | WO-2012022725 A2 * | 2/2012 | .......... C12N 5/0623 |

OTHER PUBLICATIONS

Temple et al (Nature, 414: 112-117, 2001).*
Zhao et al (PNAS, 107(5): 1876-1881, 2010).*
Li et al, (Neuropsychopharmacology, 34(11): 2404-2419, 2009).*
Zhang et al ,Psychopharmacology (2006) 186: 209-217.*
Liu et al (Cell Research, 22(7): 1087-1091, 2012).*
Yang (Cell Stem Cell, 2; 9(6): 1-18, 2011 (Year: 2011).*
Brevini et al., 2010, Theriogenology, vol. 74, pp. 544-550 (Year: 2010).*
Paris et al. (2010, Theriogenology, vol. 74, pp. 516-524) (Year: 2010).*
Munoz et al. (2009) Stem Cell Rev. and Rep., vol. 5, 6-9 (Year: 2009).*
Laurent (Cell Stem Cell 8, 106-118, Jan. 7, 2011 (Year: 2011).*
Han, Dong Wook et al. "Direct Reprogramming of Fibroblasts into Neural Stem Cells by Defined Factors." Cell Stem Cell, vol. 10, No. 4, Apr. 1, 2012, pp. 465-472, XP055027756.
Ring, Karen L. et al. "Direct Reprogramming of Mouse and Human Fibroblasts into Multipotent Neural Stem Cells with a Single Factor." Cell Stem Cell, vol. 11, No. 1, May 15, 2012, pp. 100-109.
Zhu Saiyong et al. "Small molecules enable OCT4-mediated direct reprogramming into expandable human neural stem cells." Cell Research, vol. 24, No. 1, Jan. 1, 2014, pp. 126-129.

(Continued)

*Primary Examiner* — Anoop K Singh
*Assistant Examiner* — Magdalene K Sgagias
(74) *Attorney, Agent, or Firm* — Edwin S. Flores; Daniel J. Chalker; Chalker Flores, LLP

(57) ABSTRACT

The present invention relates to a method of preparing induced neural stem cells which are reprogrammed from differentiated cells.

The method of producing the induced neural stem cells according to the present invention enables preparation of the induced neural stem cells from non-neuronal cells using only two inducing factors of SOX2 and HMGA2. Therefore, the method of the present invention can prepare induced neural stem cells in a more efficient manner than the conventional methods, which use four or five inducing factors. Additionally, the method of the present invention shows significantly higher inducing efficiency and proliferation capacity than when only a single SOX2 gene is used, thus increasing its potency to be used for therapeutic purposes.

5 Claims, 56 Drawing Sheets
Specification includes a Sequence Listing.

(56) References Cited

OTHER PUBLICATIONS

Ahmed, Sohail et al. "Transcription factors and neural stem cell self-renewal, growth and differentiation." Cell Adh. Migr., Oct., Nov. & Dec. 2009,3(4),p. 412-424.
Yu, Kyung-Rok et al., "HMGA2 regulates the in vitro aging and proliferation of human umbilical cord blood-derived stromal cells through the mTOR/p70S6K signaling pathway" Stem Cell Research (2013) 10, 156-165.
Yamanaka, Shinya "Pluripotency and nuclear reprogramming" Phil. Trans. R. Soc. B (2008) 363, 2079-2087.
Takahashi, Kazutoshi et al "Induction of Pluripotent Stem Cells from Mouse Embryonic and Adult Fibroblast Cultures by Defined Factors" Cell 126, 663-676, Aug. 25, 2006.
Yu, Junying et al "Induced Pluripotent Stem Cell Lines Derived from Human Somatic Cells" Science 318, 1917 (2007).
Takahashi, Kazutoshi et al "Induction of Pluripotent Stem Cells from Adult Human Fibroblasts by Defined Factors" Cell 131, 861-872, Nov. 30, 2007.
Vierbuchen, Thomas "Direct conversion of fibroblasts to functional neurons by defined factors" Nature, vol. 463, Feb. 25, 2010.
Thier, Marc "Direct Conversion of Fibroblasts into Stably Expandable Neural Stem Cells" Cell Stem Cell 10, 473-479, Apr. 6, 2012.
Their, Marc et al. "Direct Conversion of Fibroblasts into Stably Expandable Neural Stem Cells" Cell Stem Cell 10, 473-479 Apr. 6, 2012.

\* cited by examiner

[FIG. 1A]
hDF
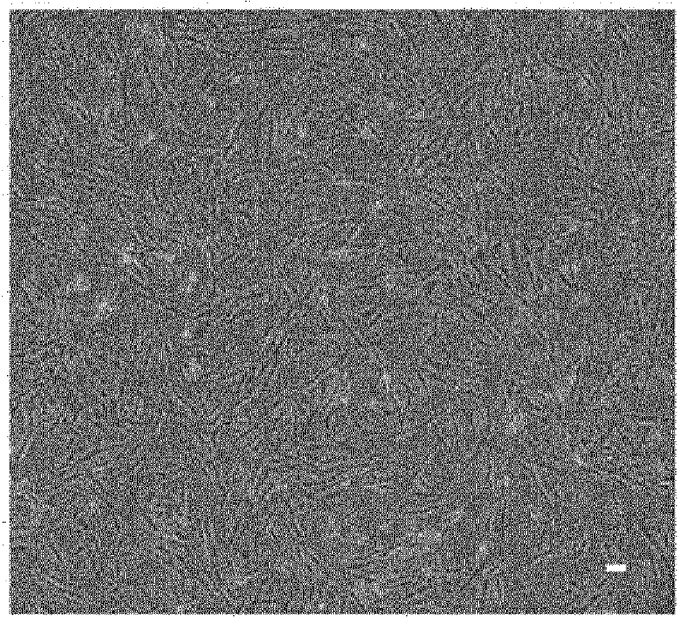
x40 scale bar= 100um
[FIG. 1B]
hDF-iNSC (SOX2)
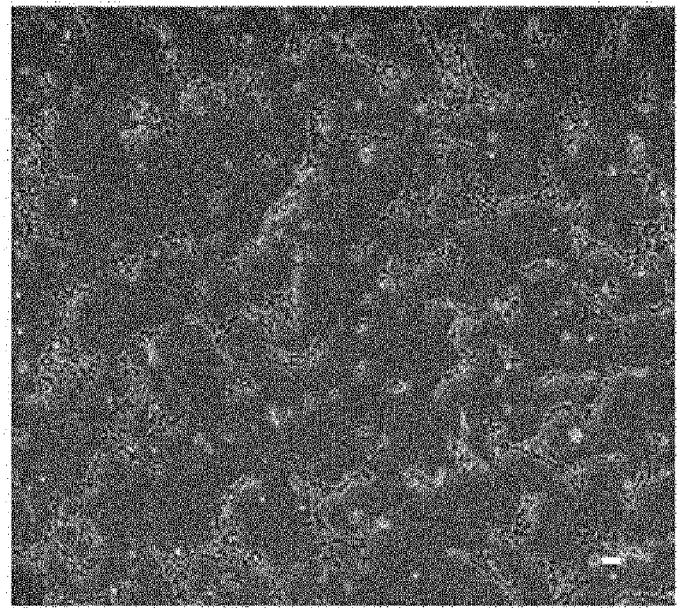
x40 scale bar= 100um

[FIG. 1C]
hDF-iNSC (SOX2)
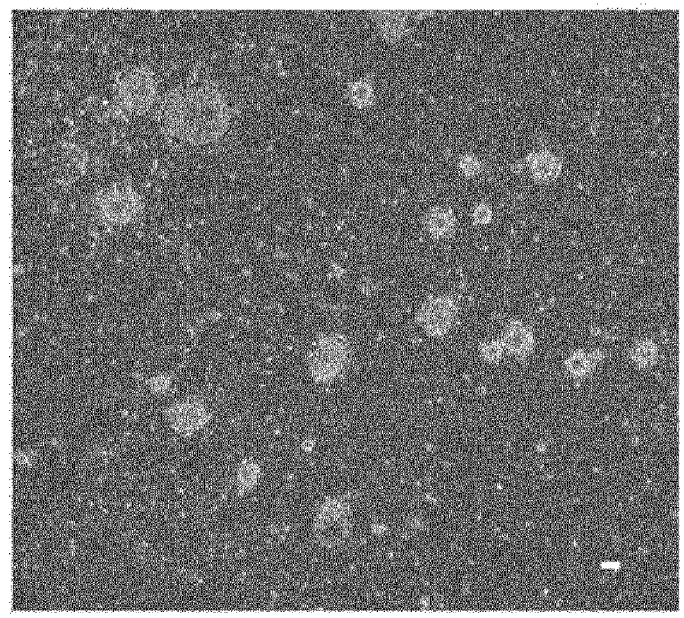
x40 scale bar= 100um
[FIG. 1D]
hDF-iNSC (SOX2)
PAX6/NESTIN/DAPI
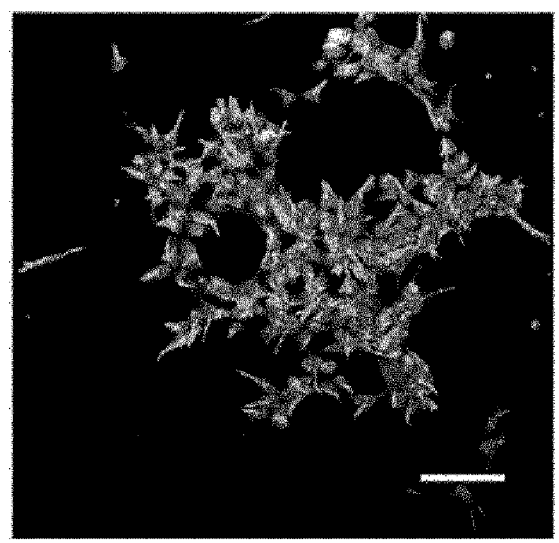
x200 scale bar= 100um

[FIG. 1E]
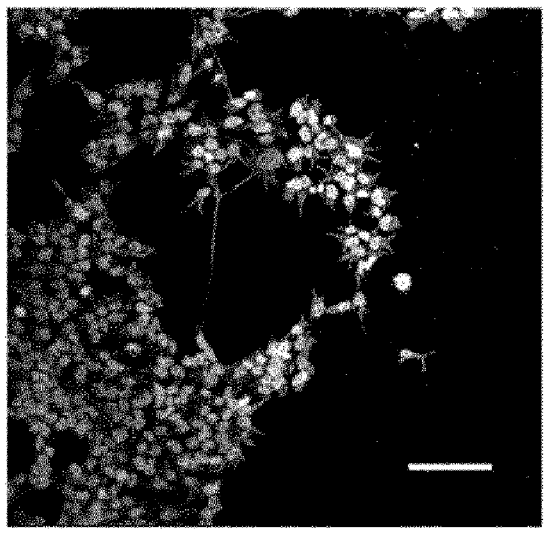

[FIG. 1F]
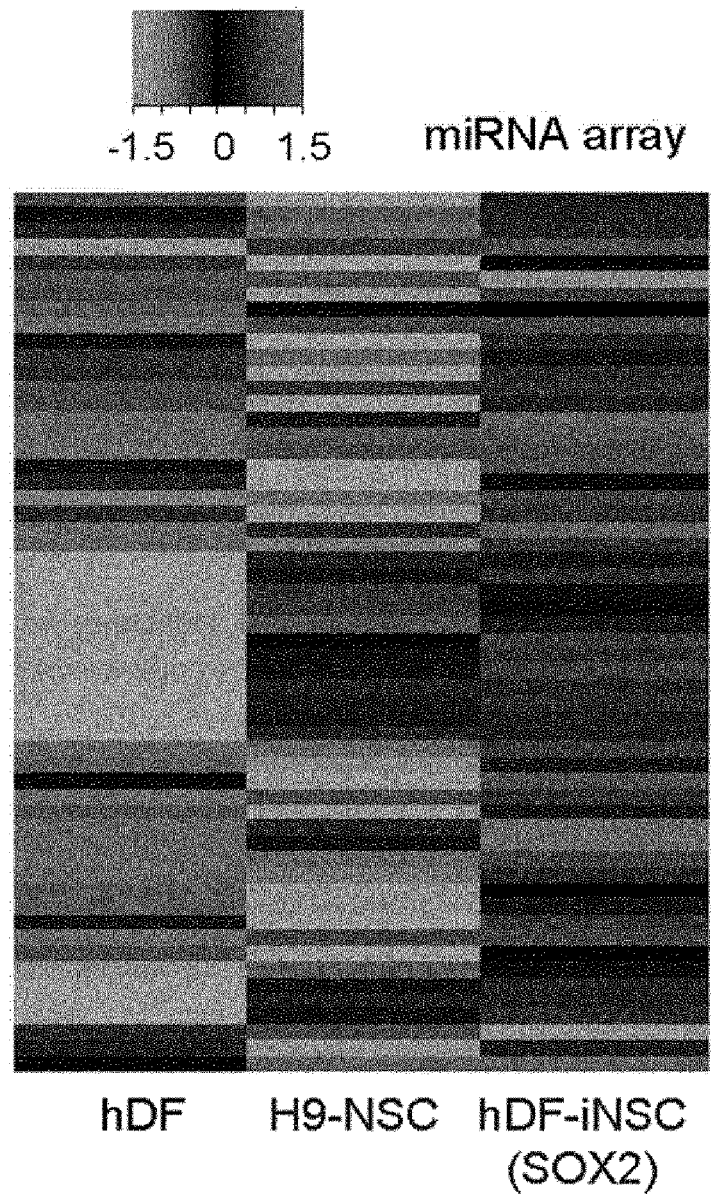

[FIG. 1G]
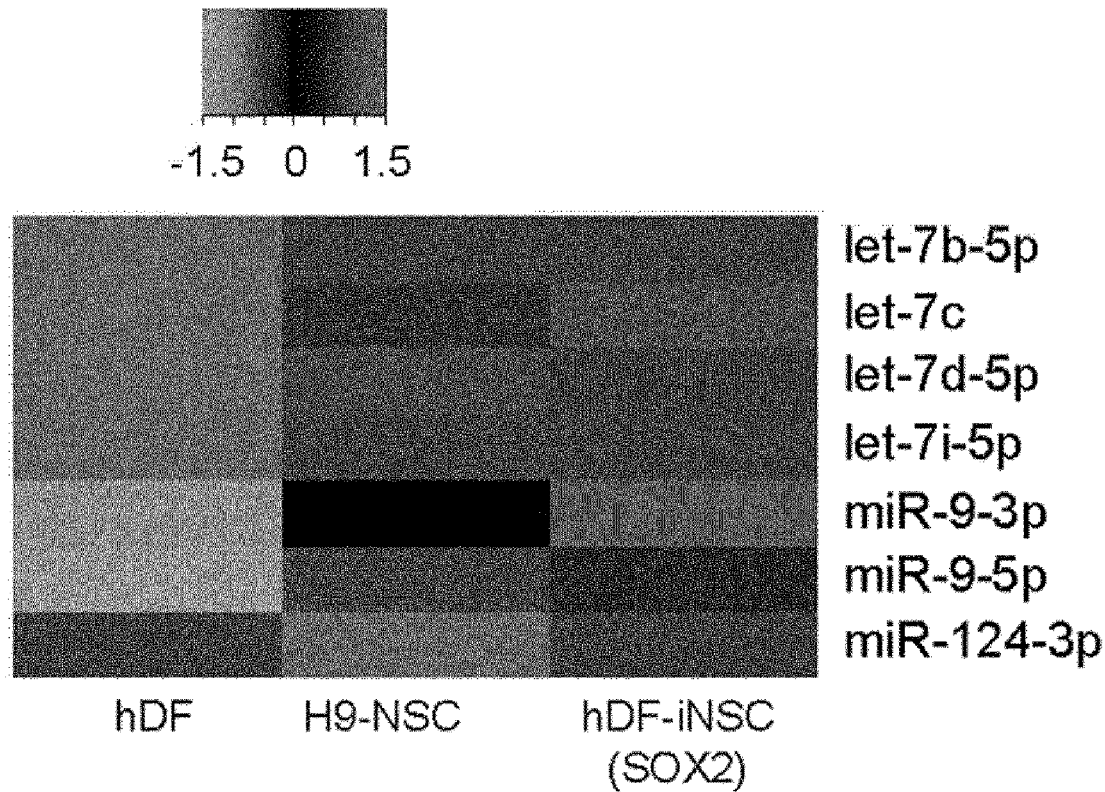
[FIG. 1H]
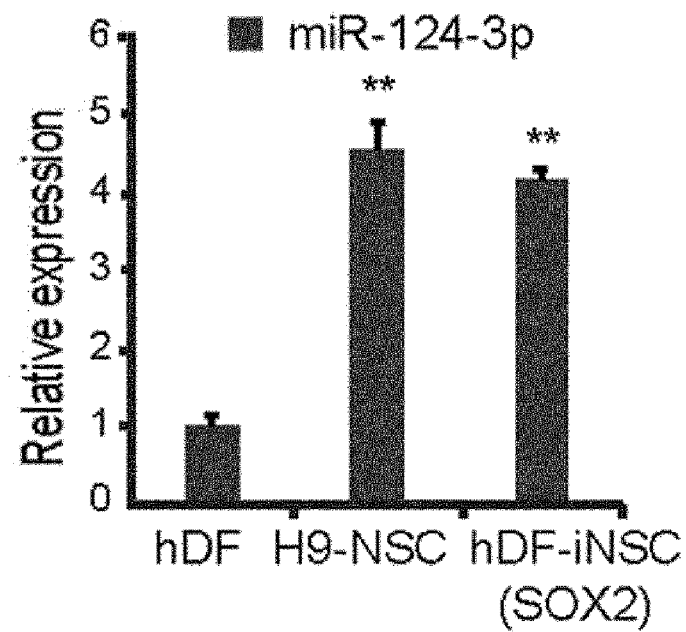

[FIG. 1I]
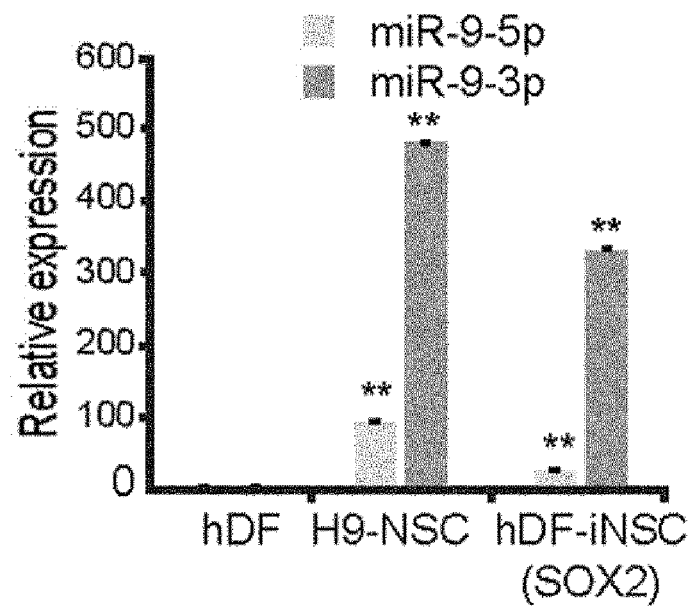

[FIG. 1J]
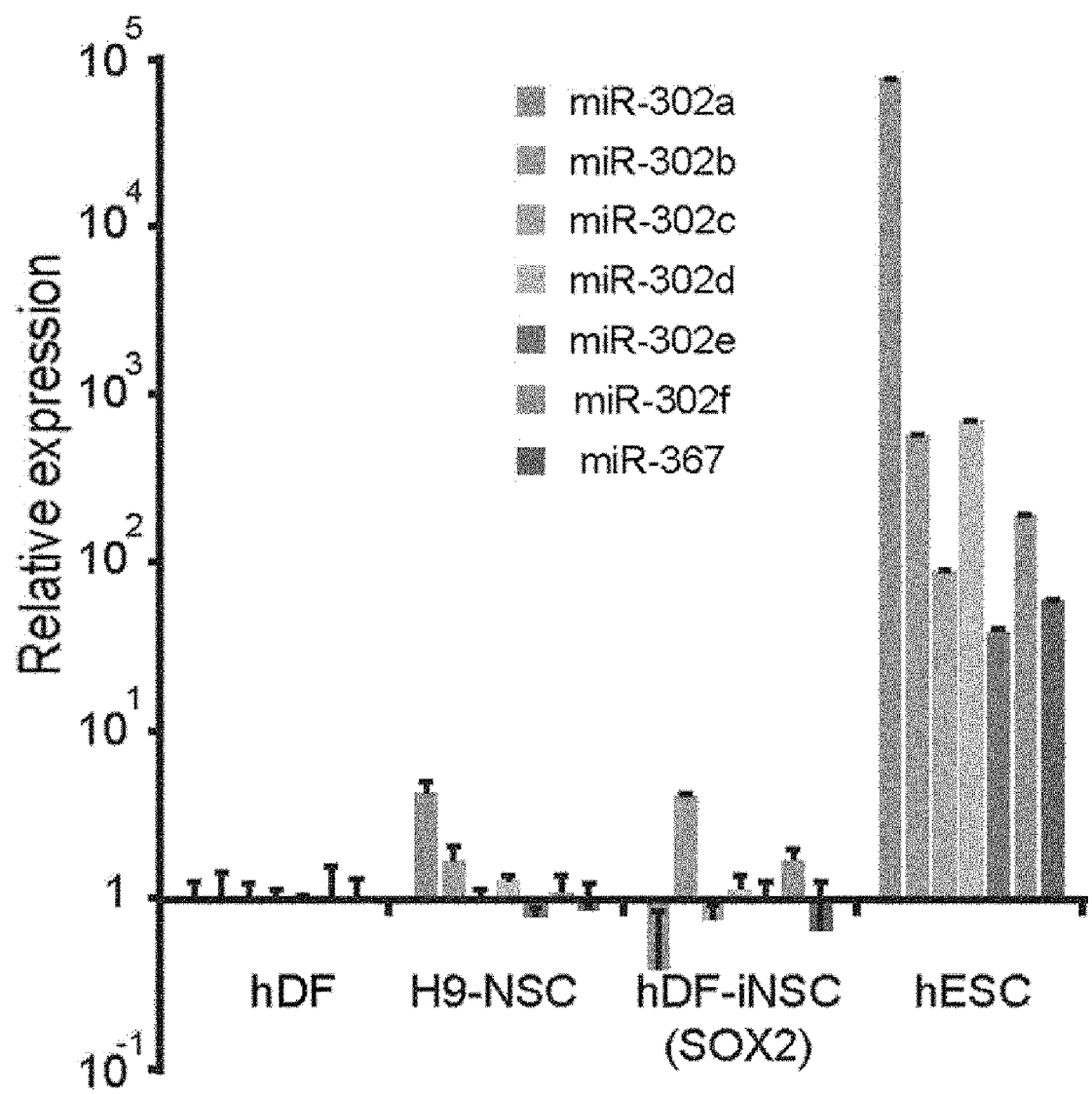

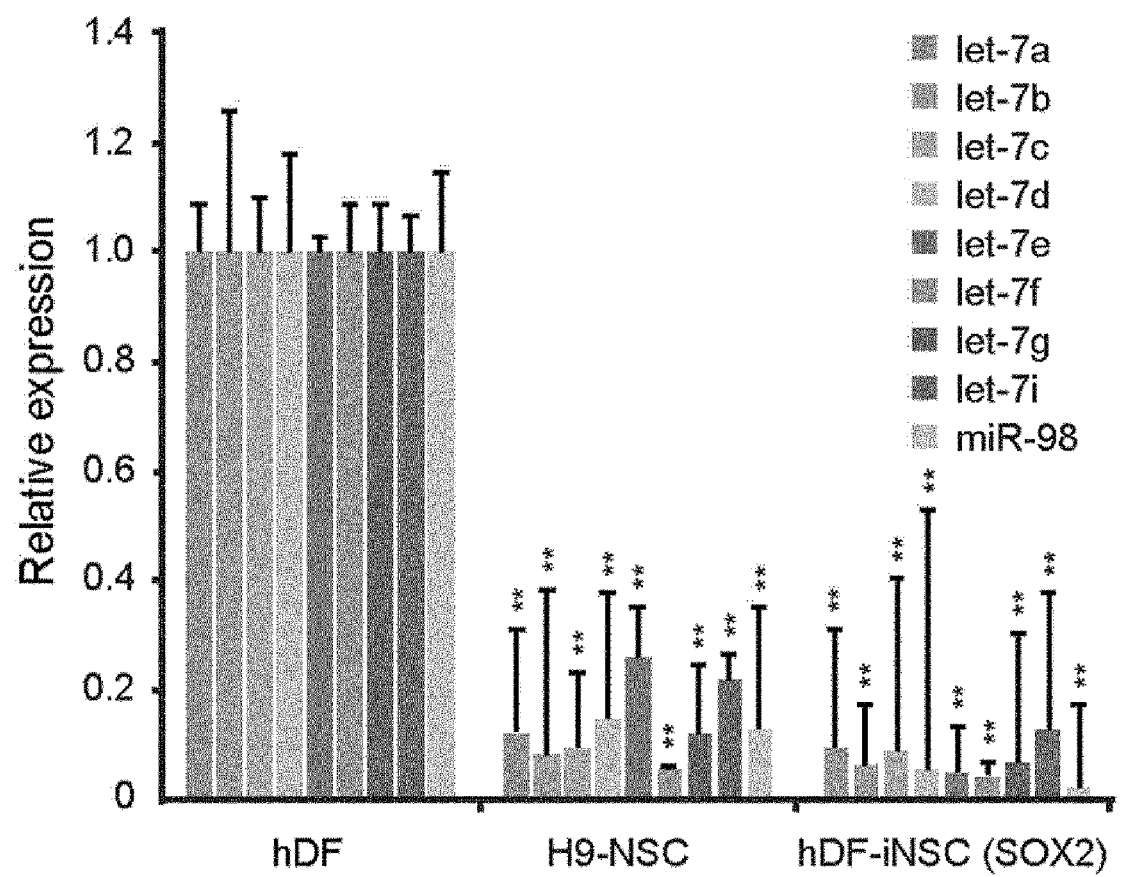
[FIG. 1K]

[FIG. 1L]
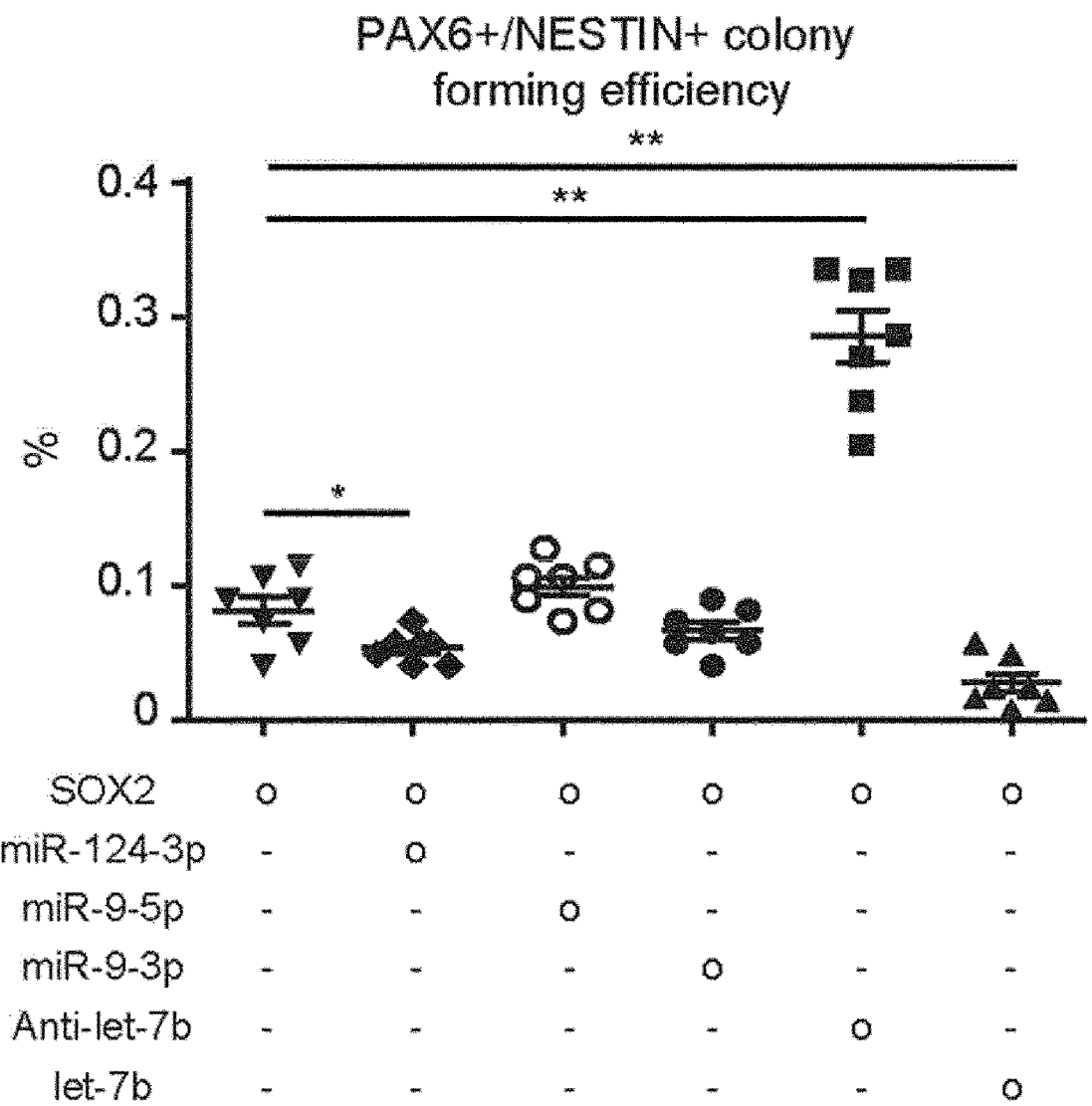

[FIG. 2A]
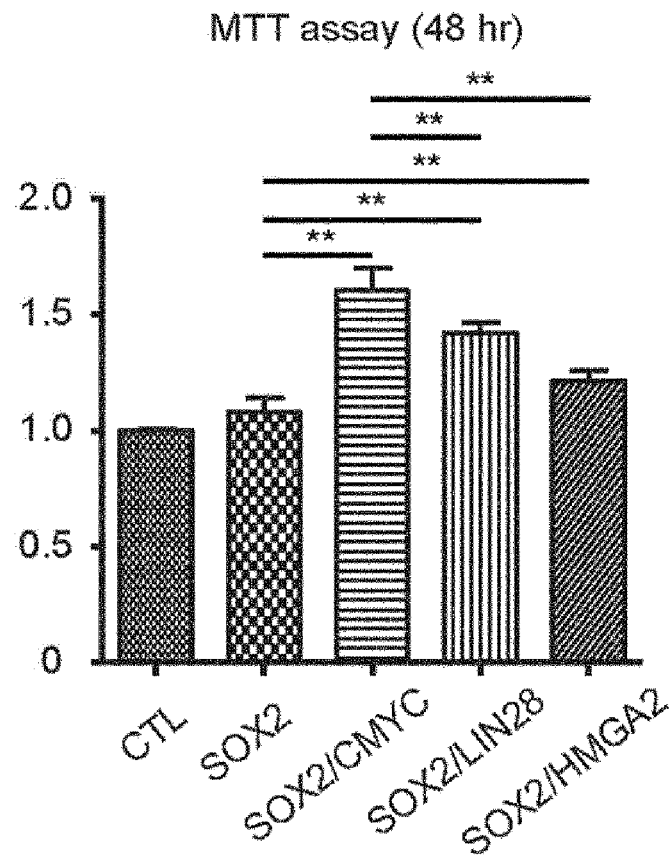
[FIG. 2B]
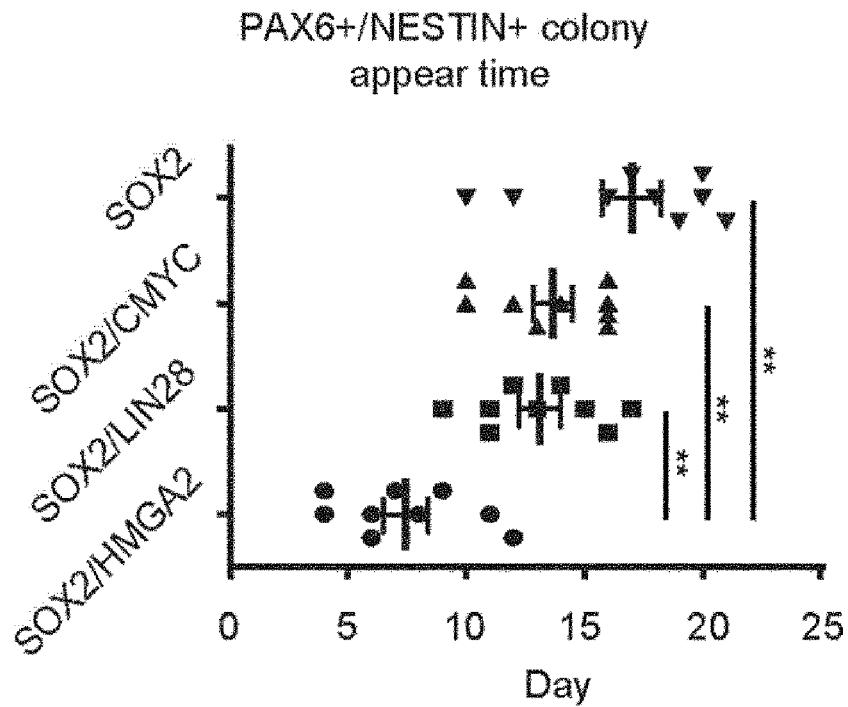

[FIG. 2C]
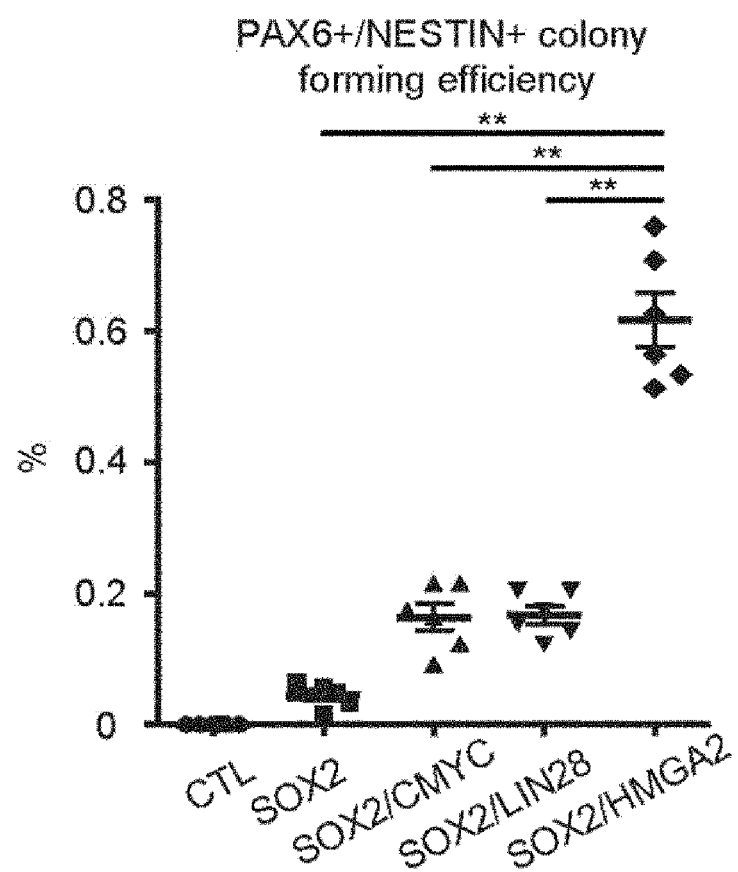

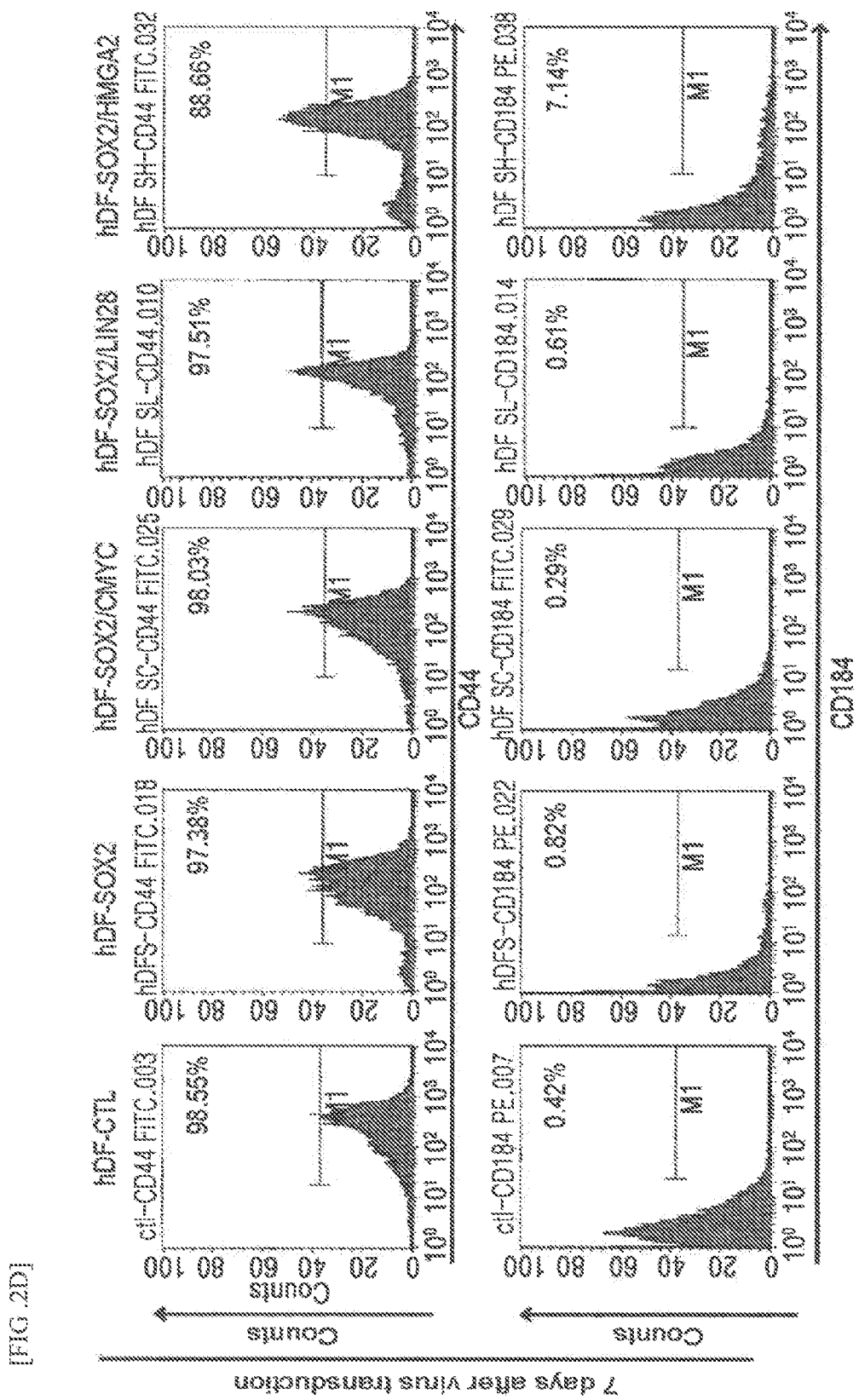
[FIG. 2D]

[FIG. 2E]
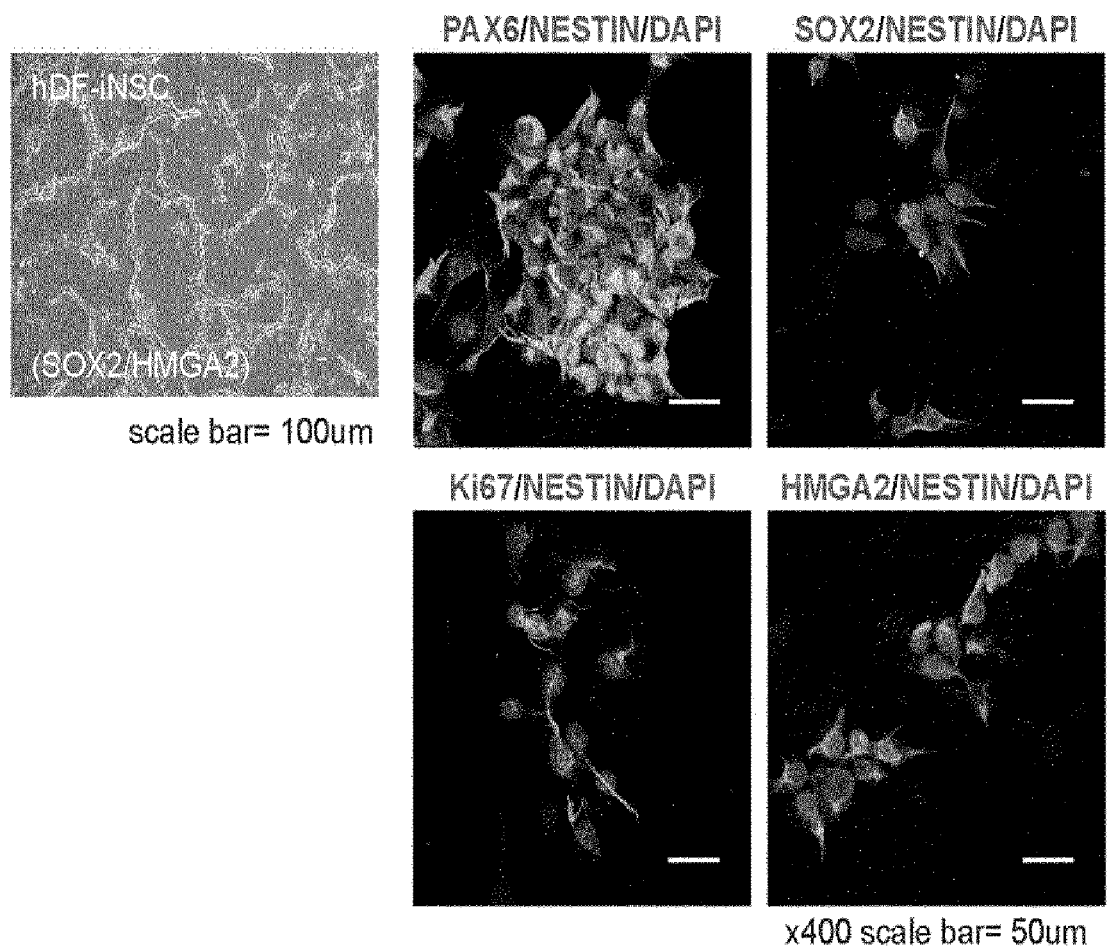

[FIG. 2F]
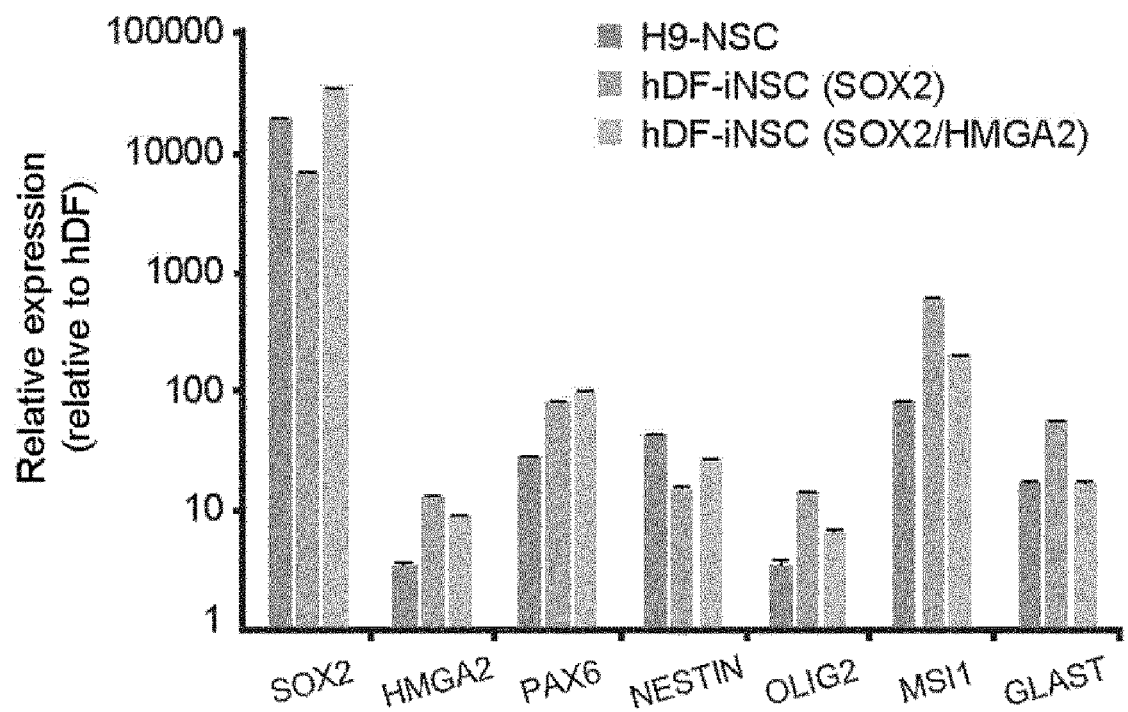

[FIG. 2G]
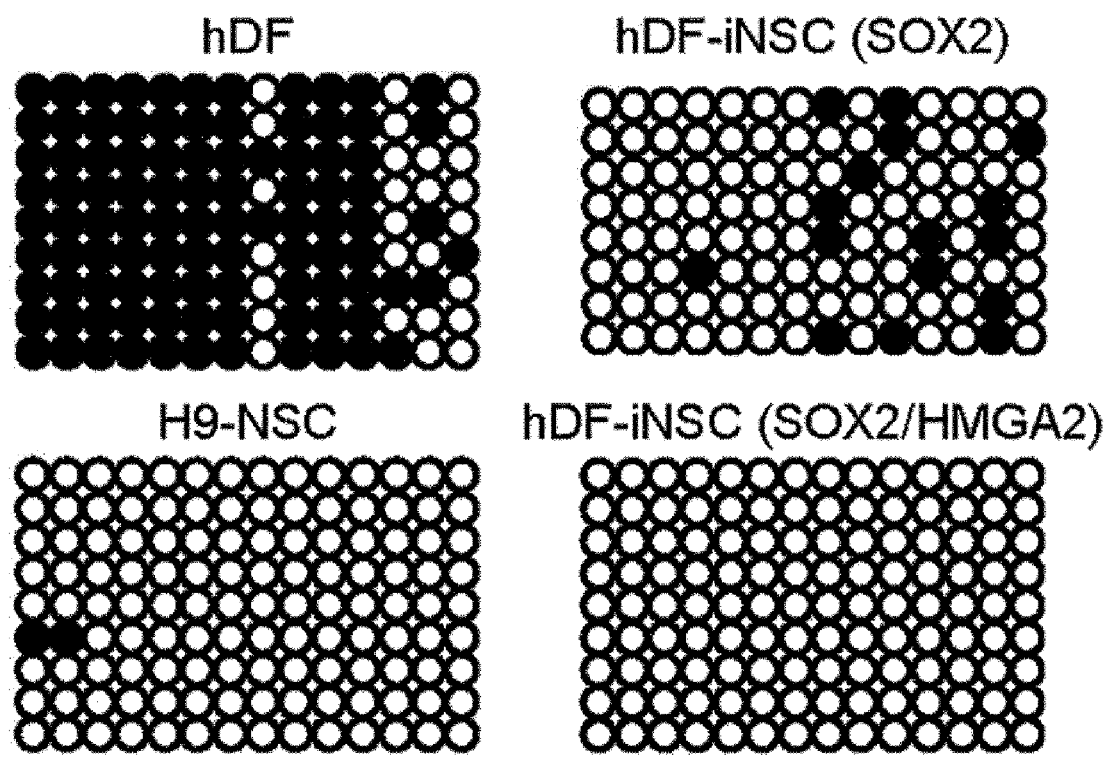

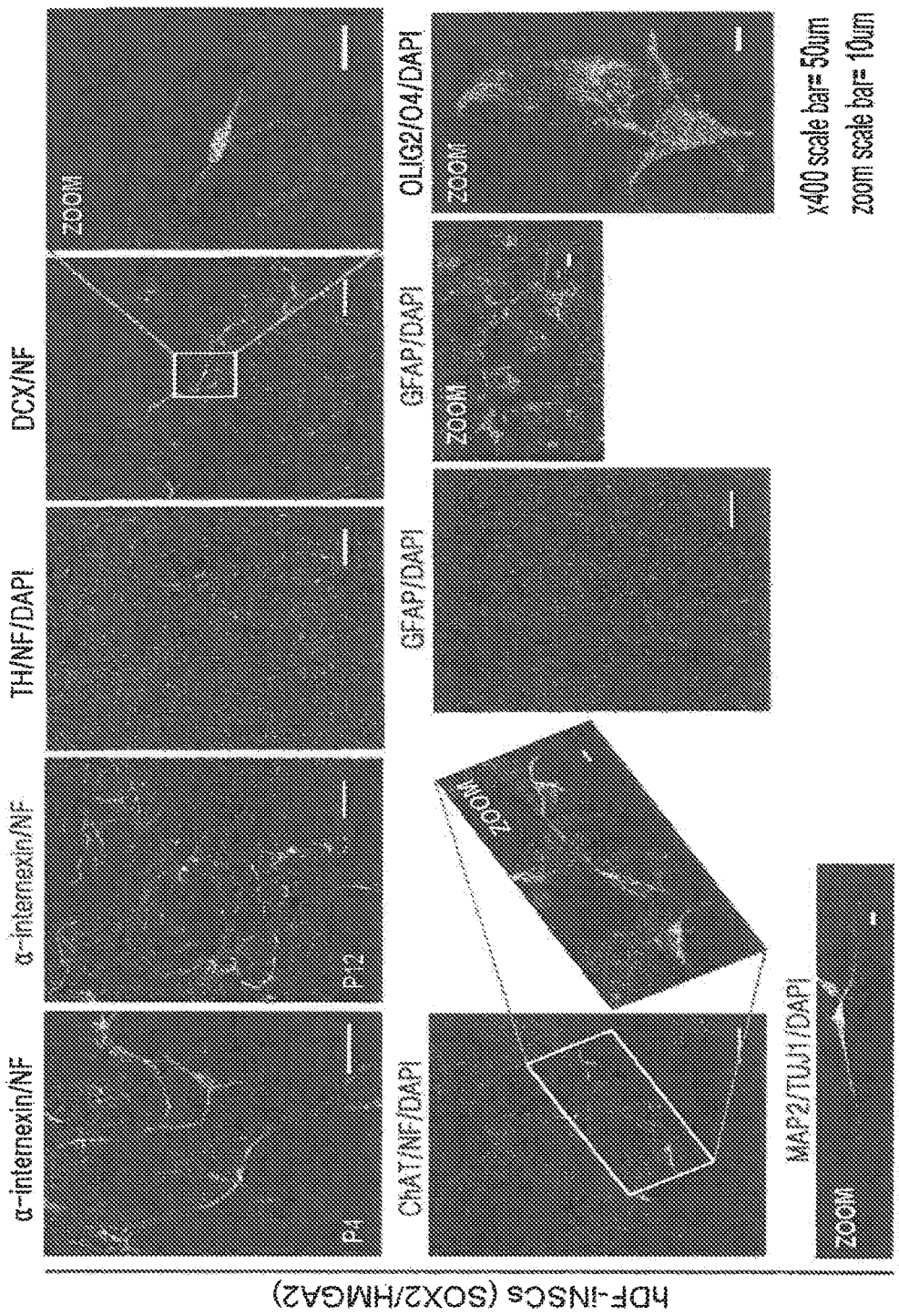
[FIG. 3A]

[FIG. 3B]
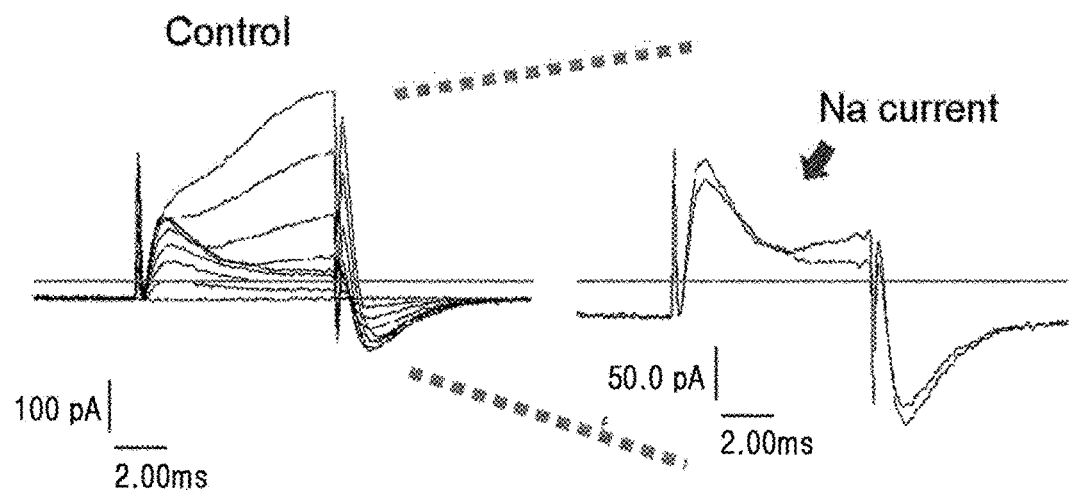
[FIG. 3C]
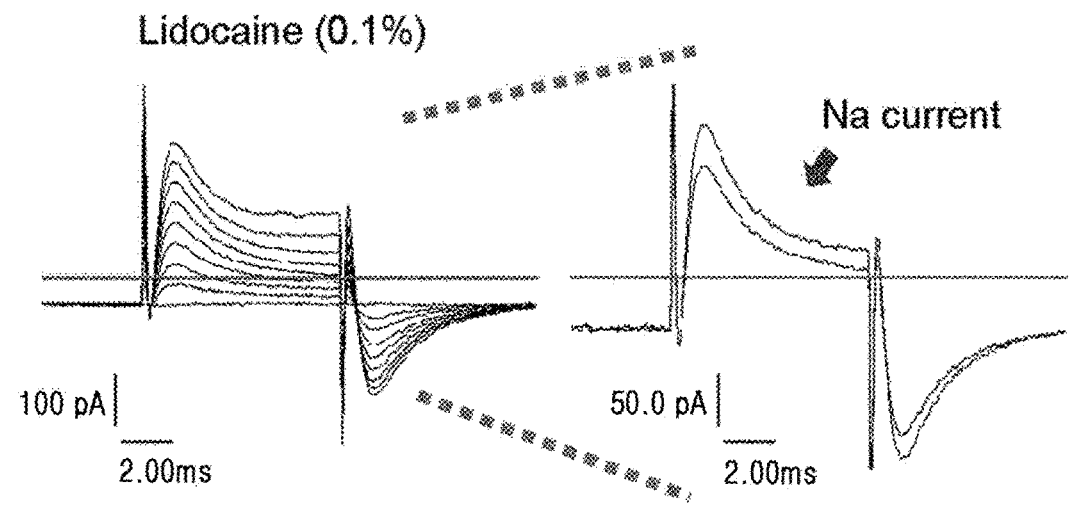

[FIG. 3D]
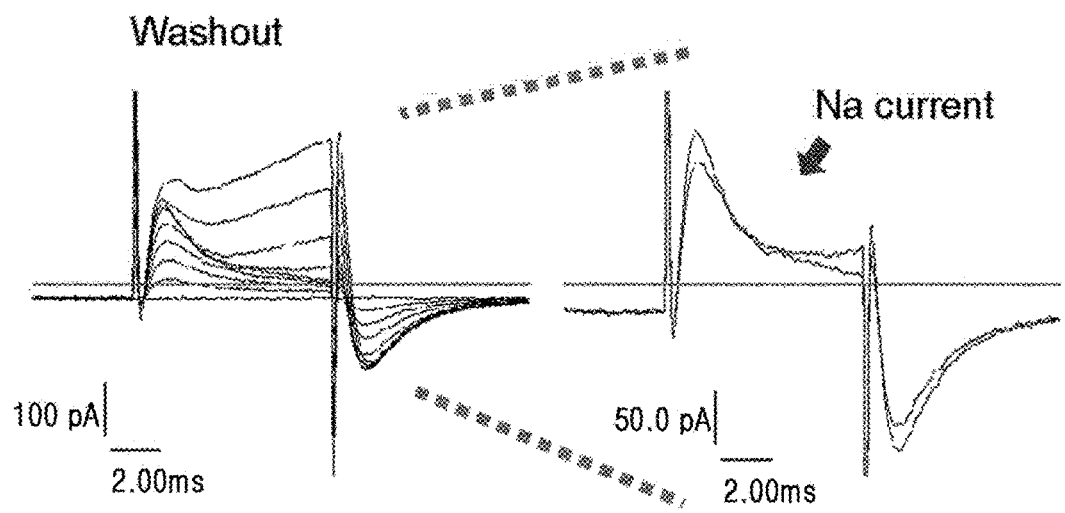

[FIG. 3E]
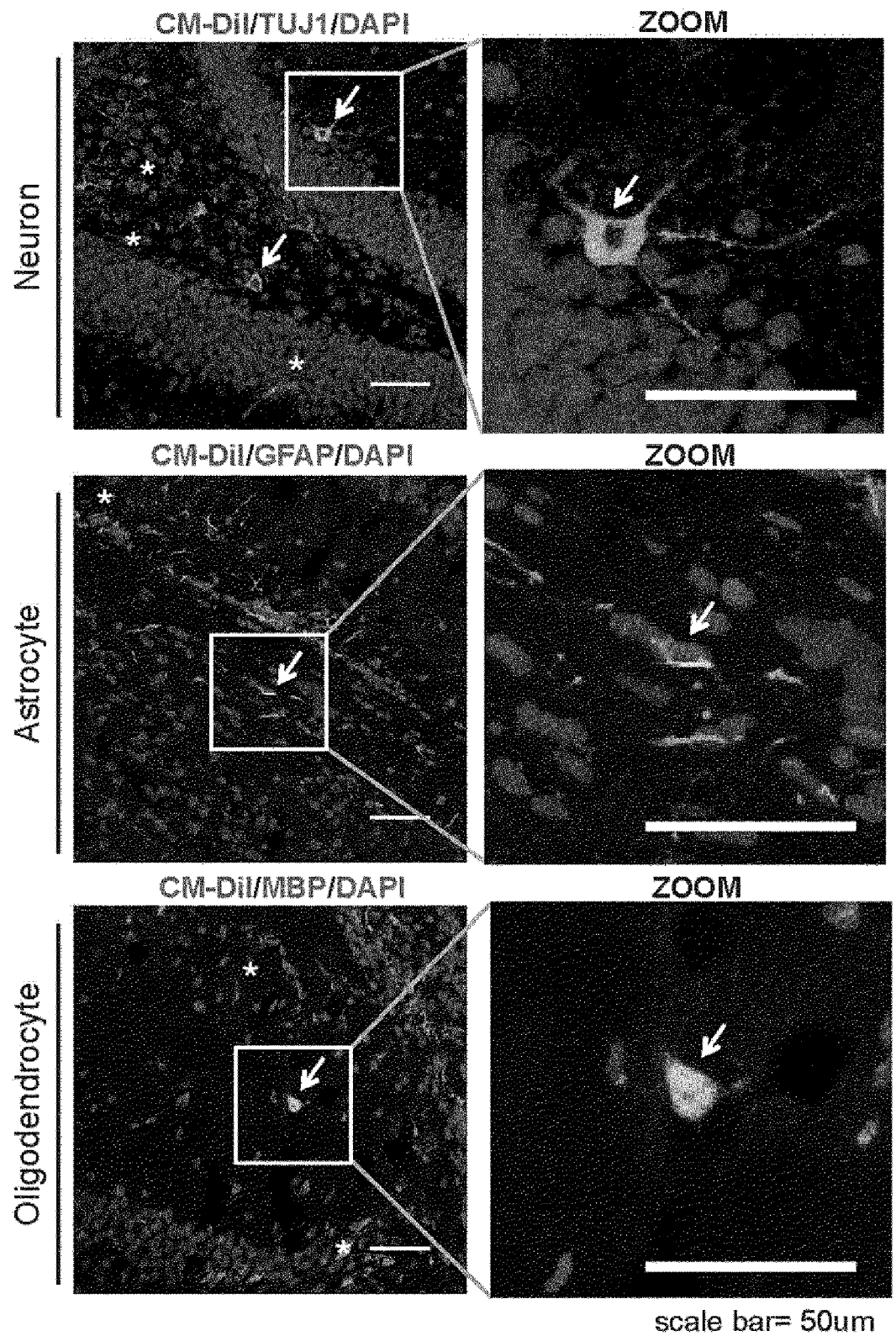

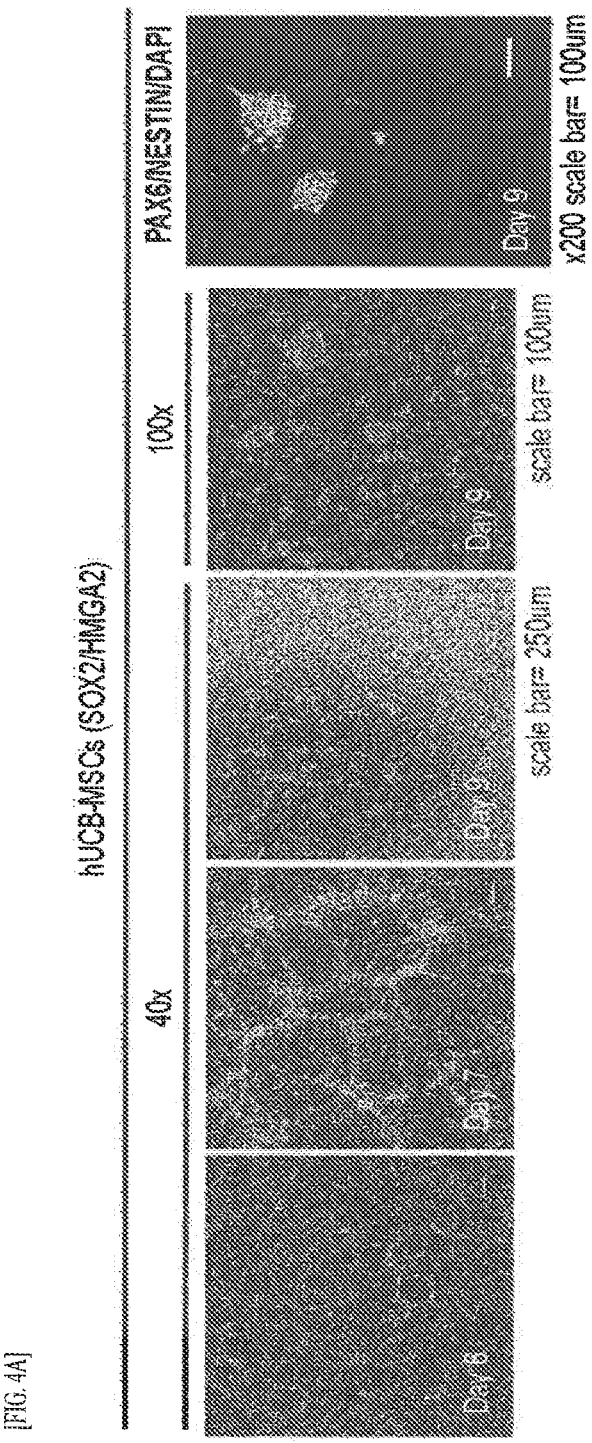
[FIG. 4A]

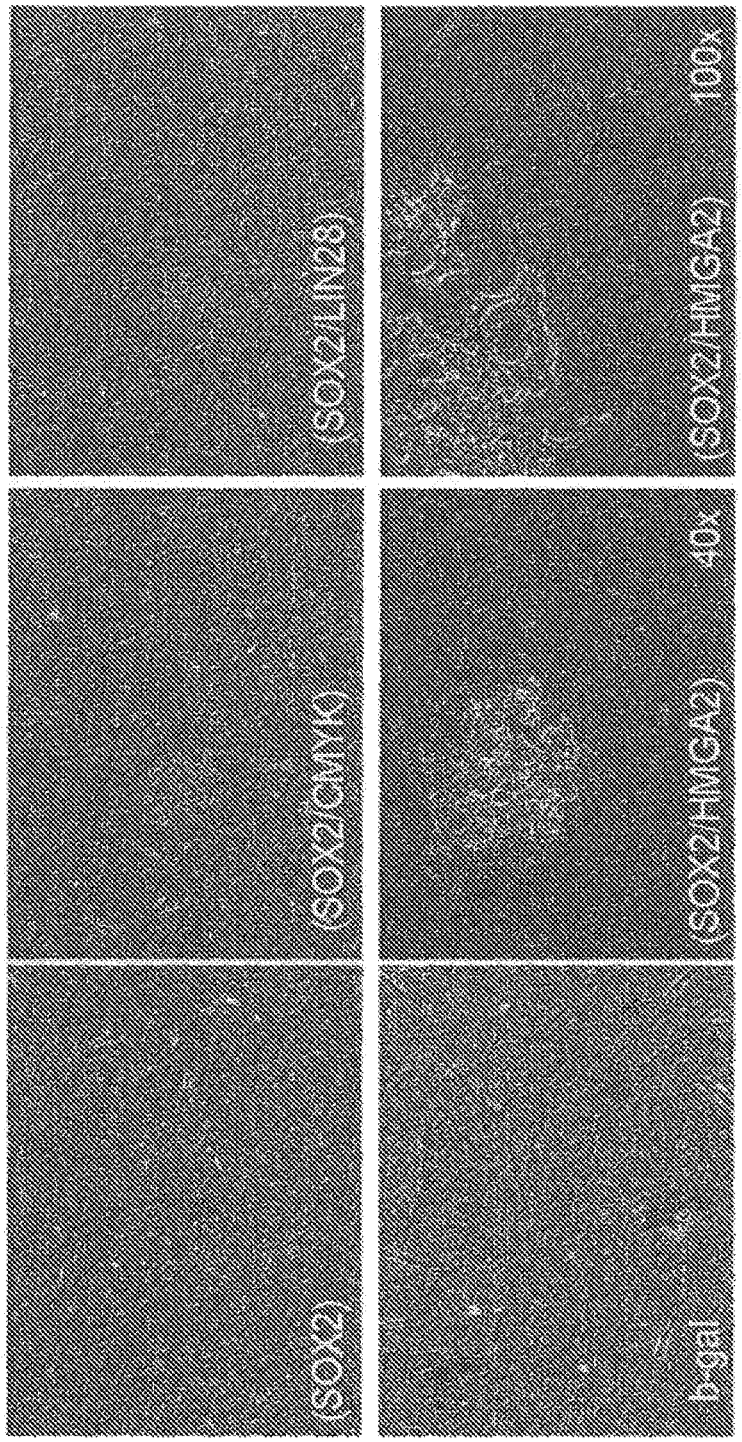
[FIG. 4B]

[FIG. 4C]
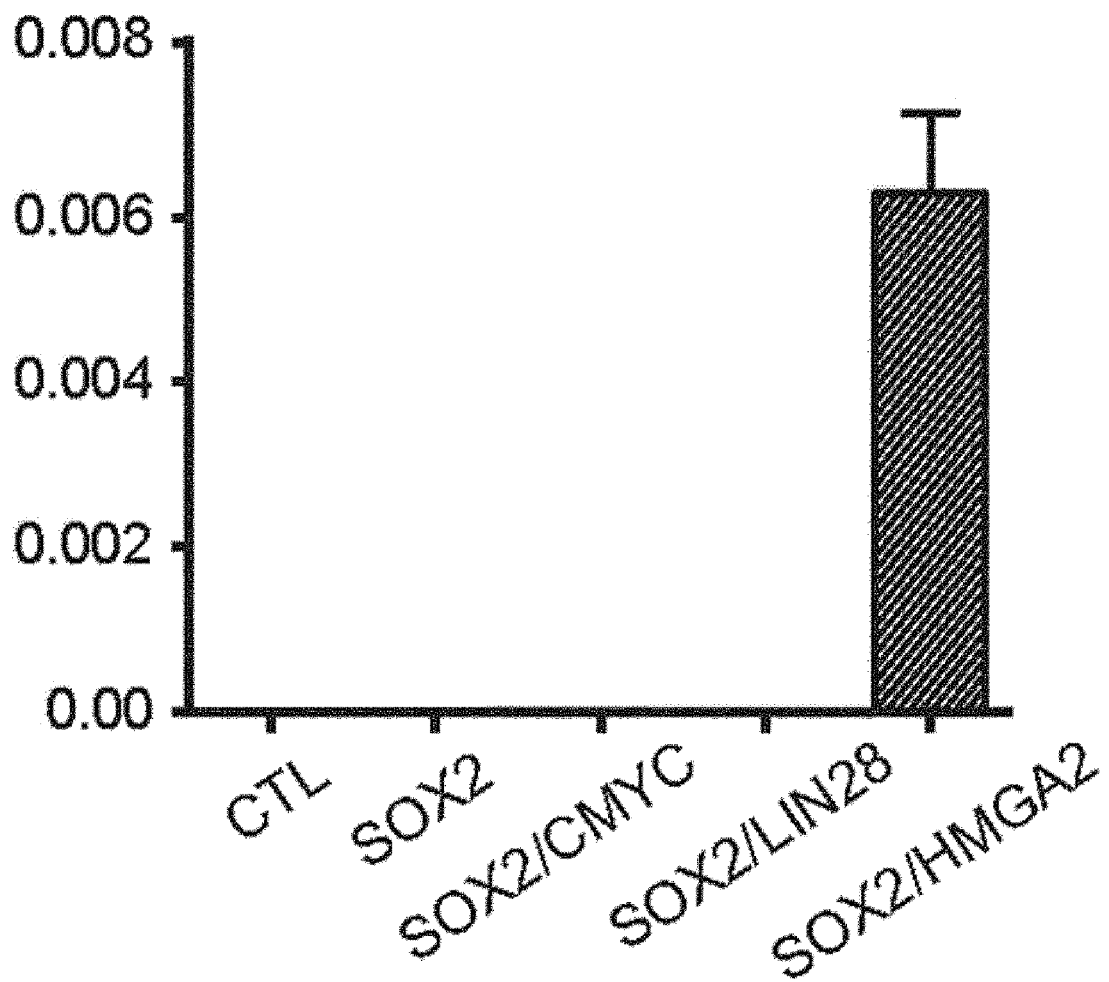

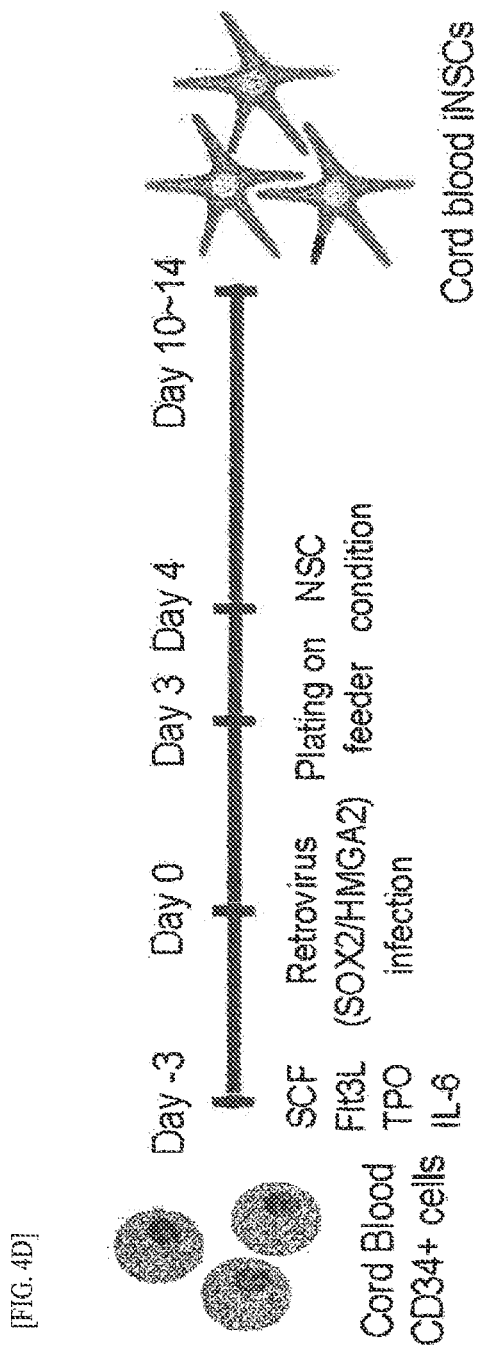
[FIG. 4D]

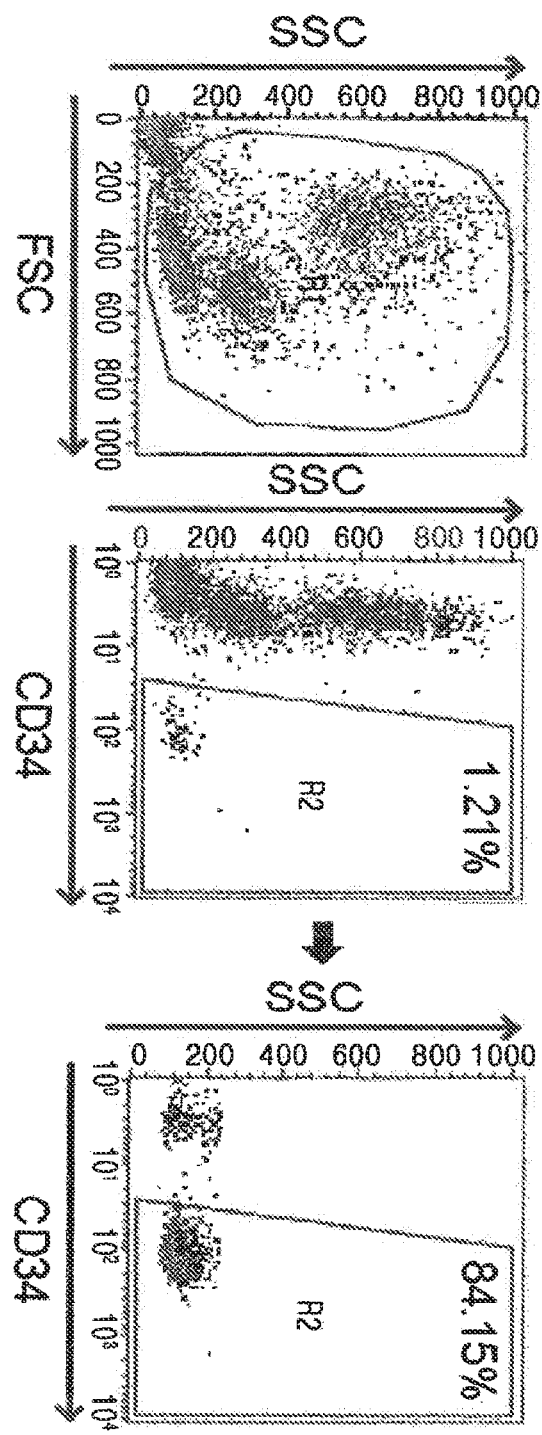
[FIG. 4E]

[FIG. 4F]
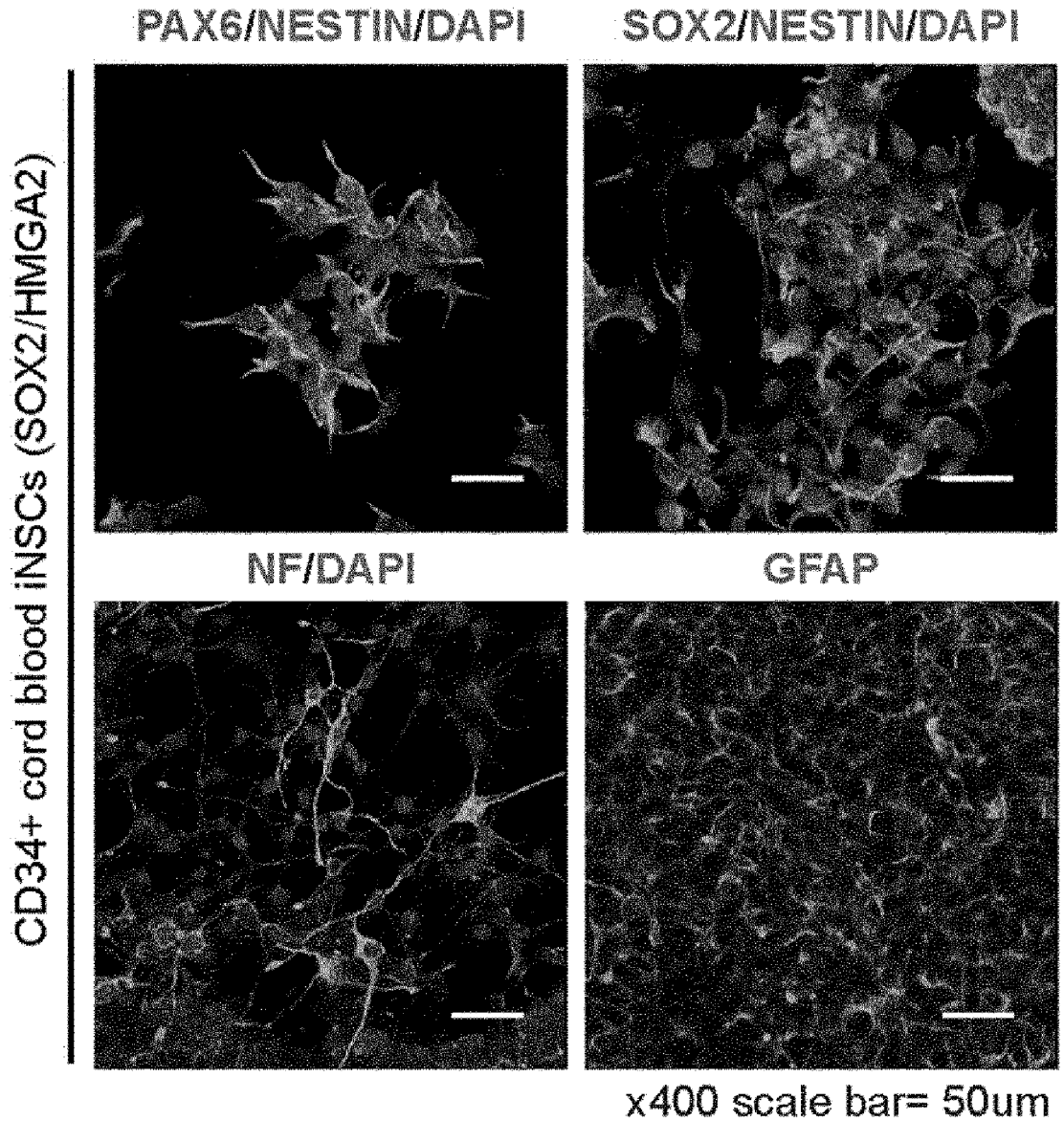

[FIG. 5]
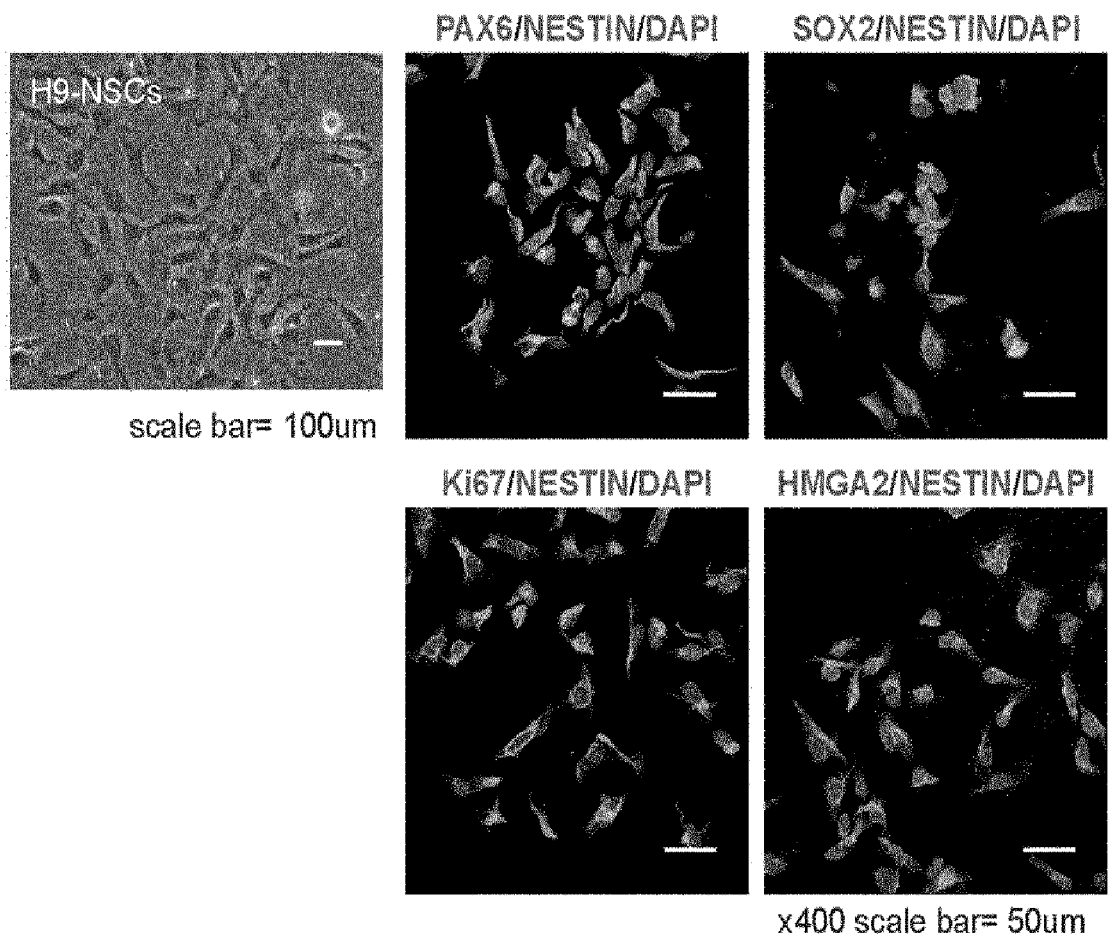

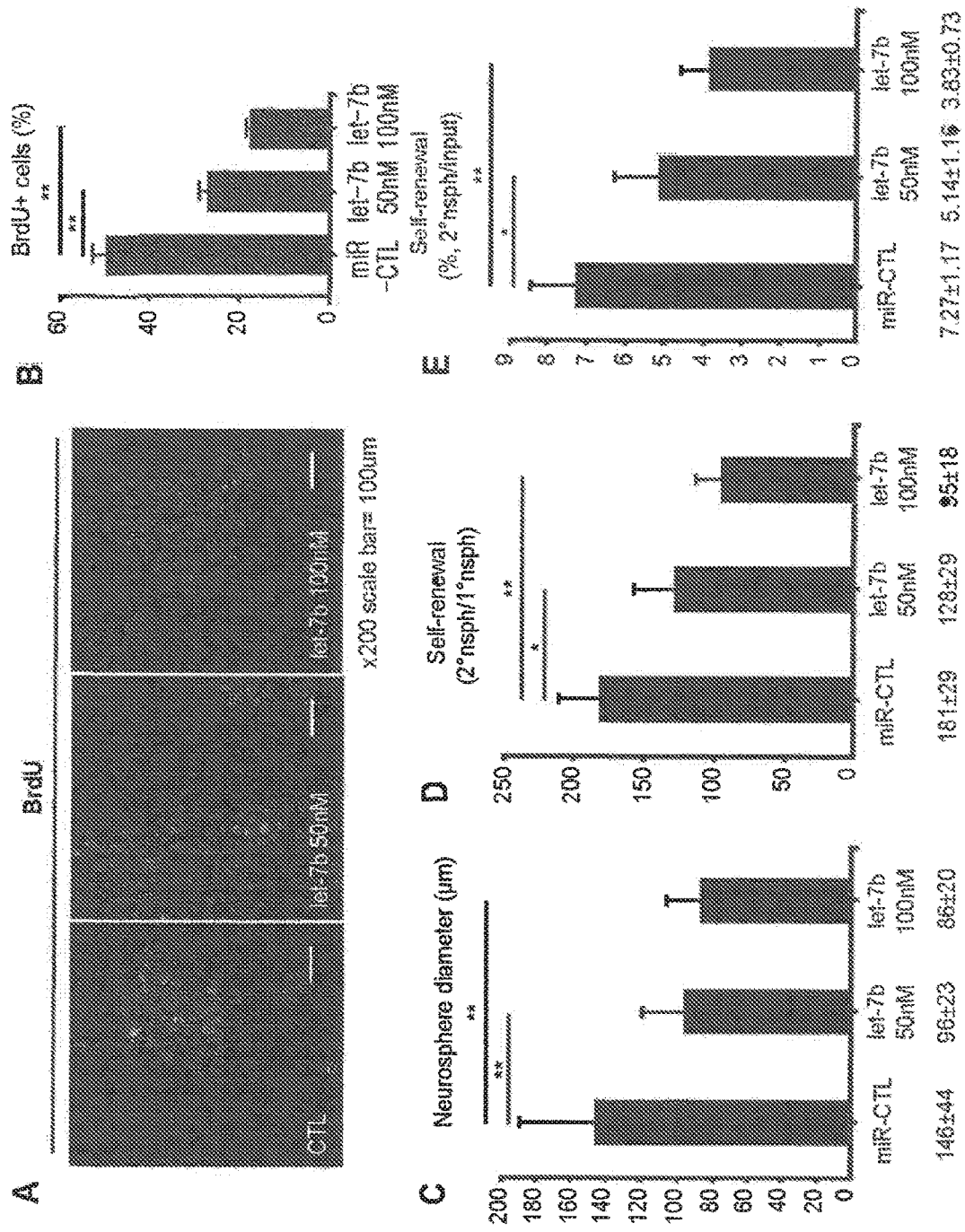
[FIG. 6]

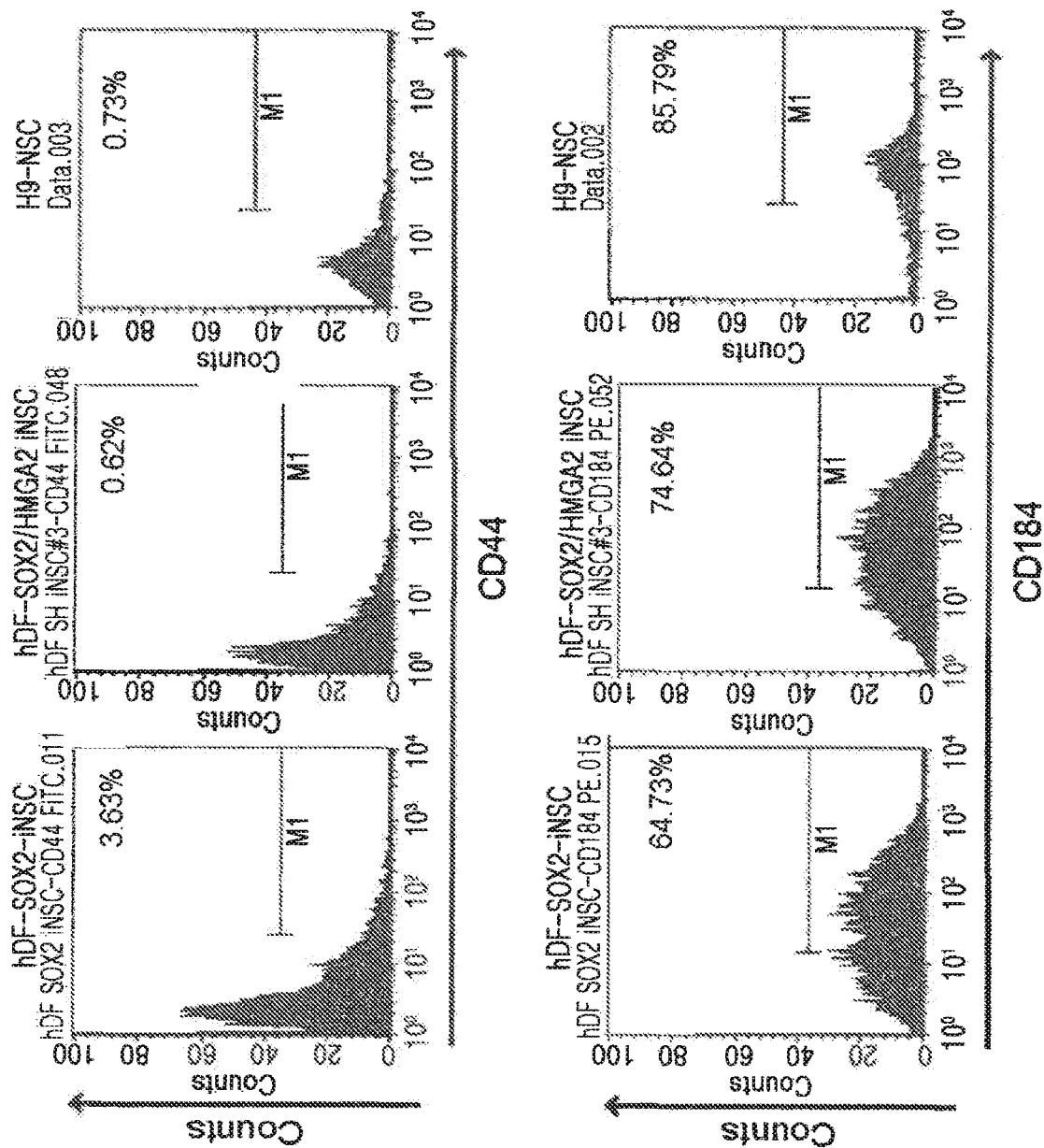
[FIG. 7A]

[FIG. 7B]
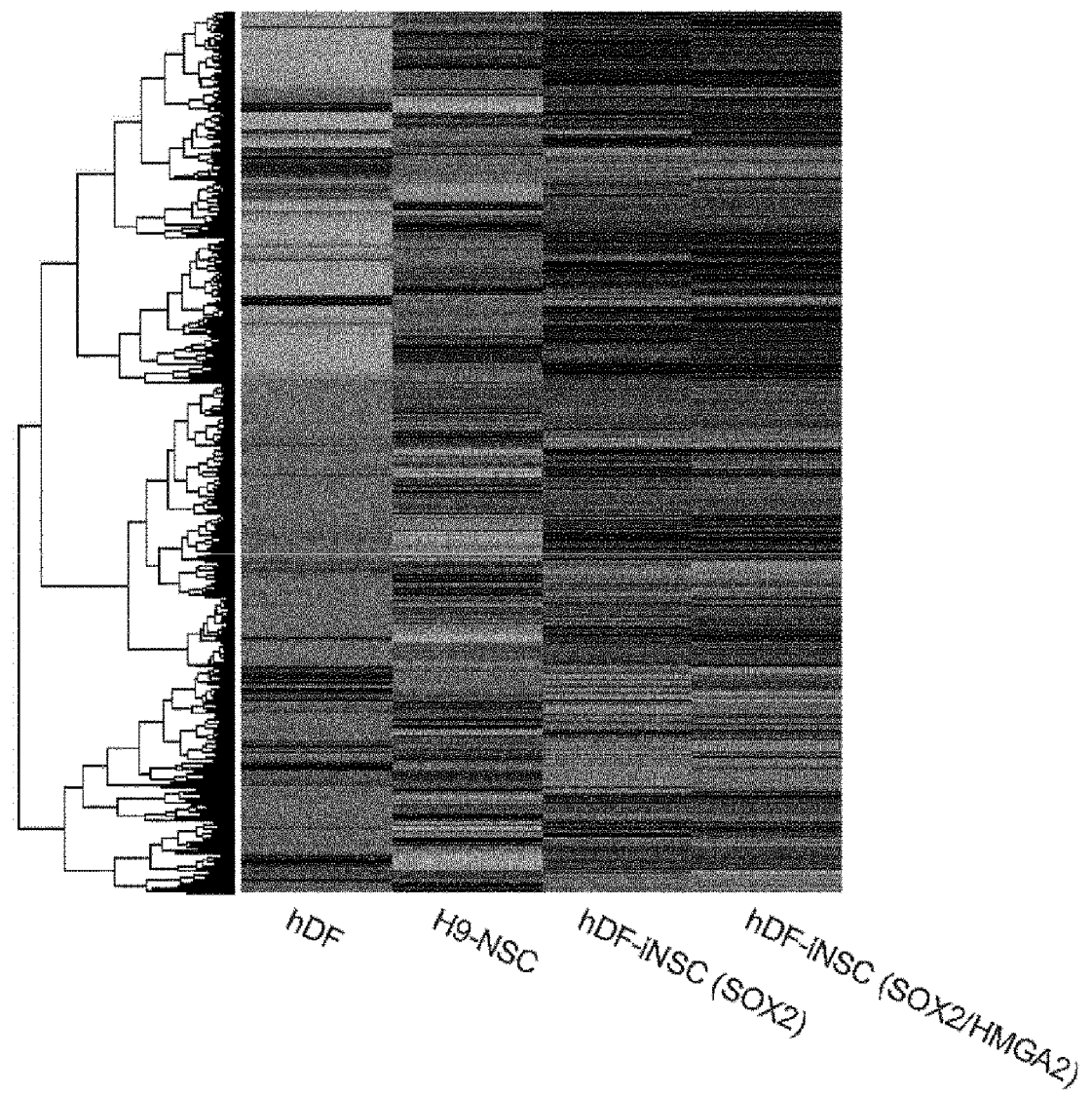

[FIG. 7C]
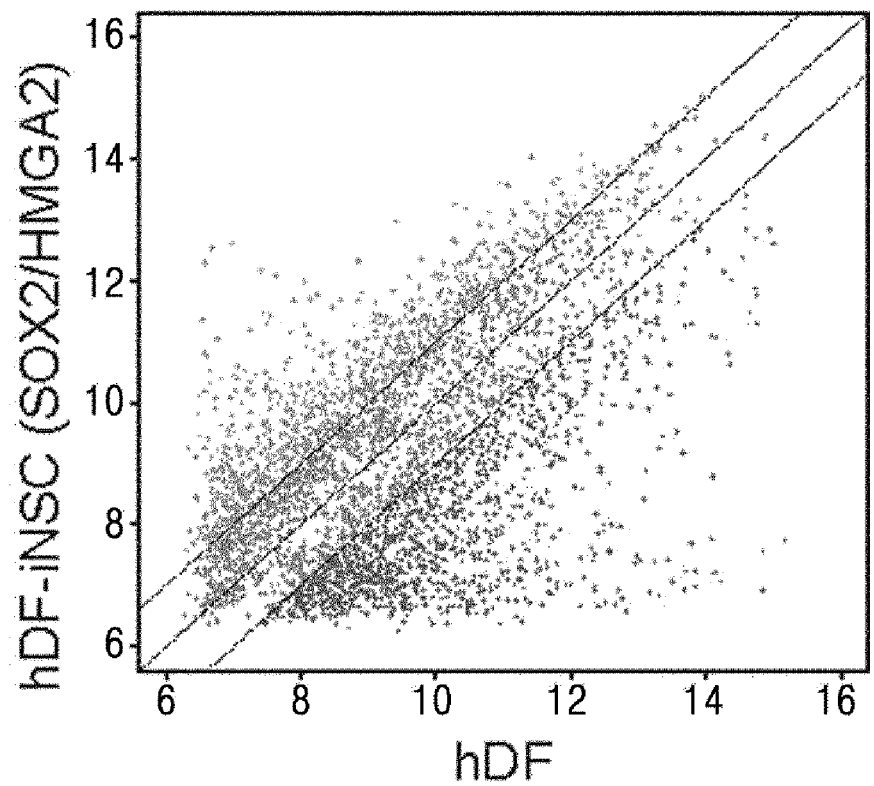
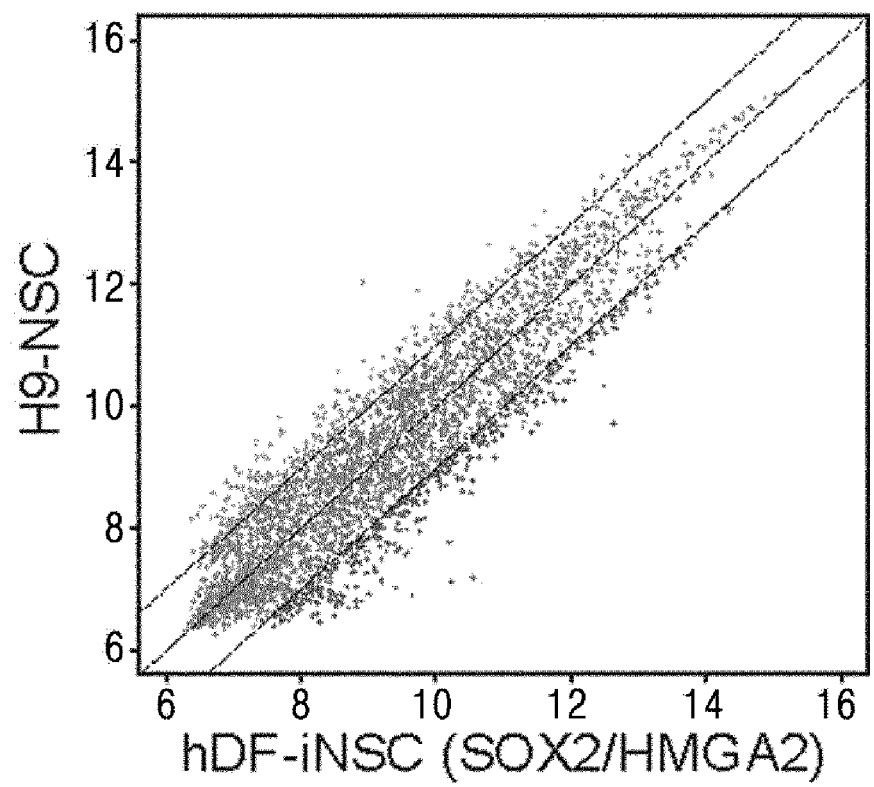

[FIG. 8]
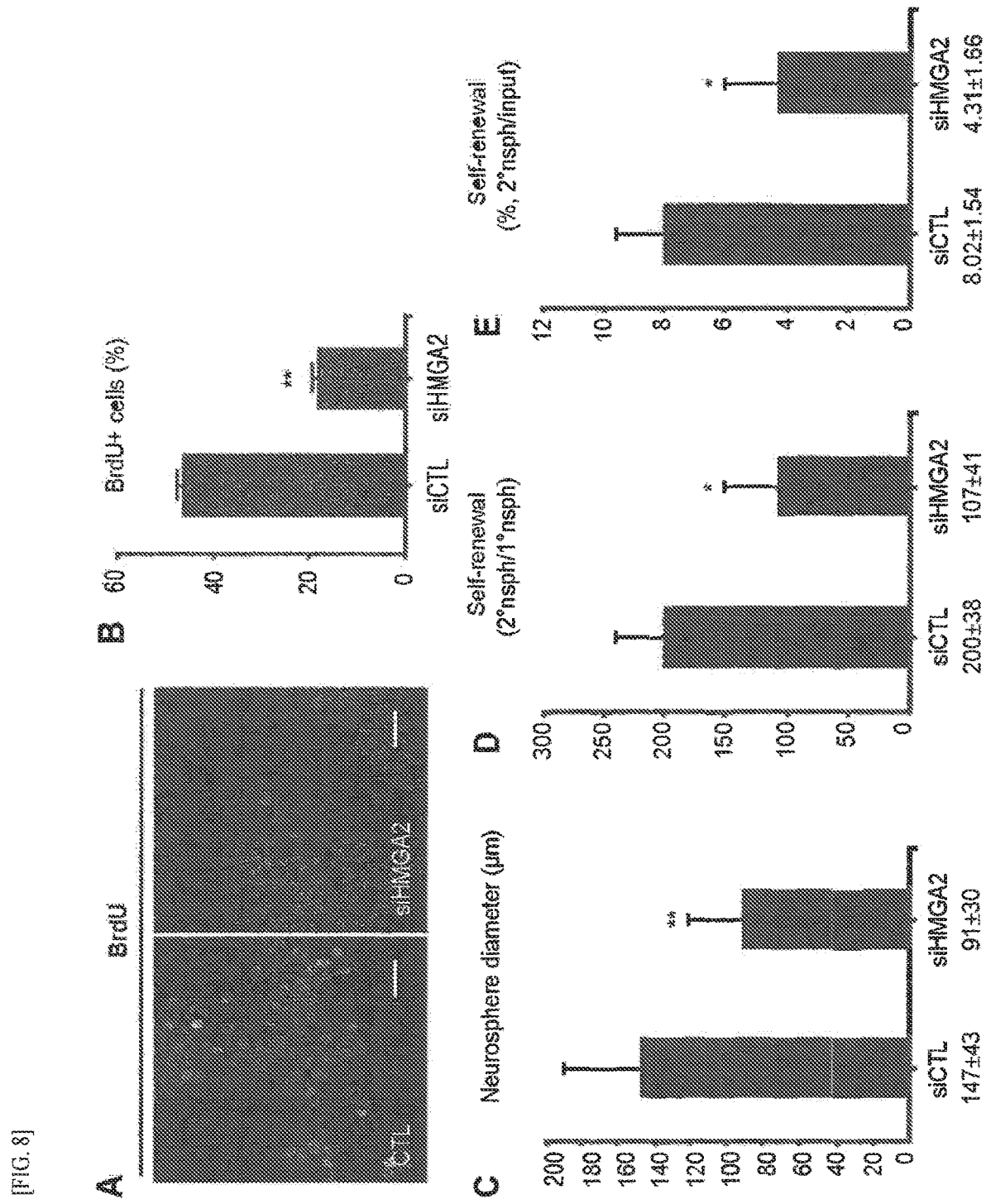

[FIG. 9A]
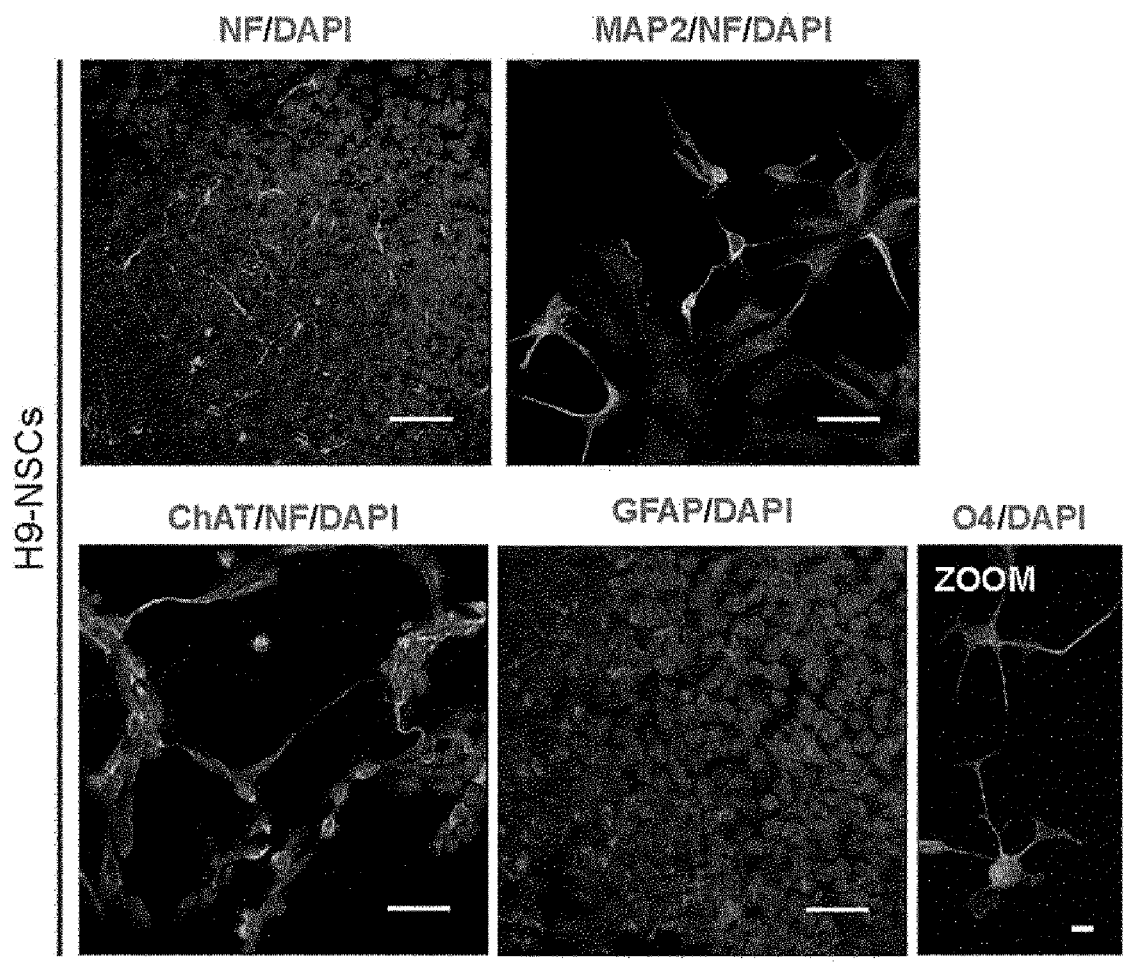
[FIG. 9B]
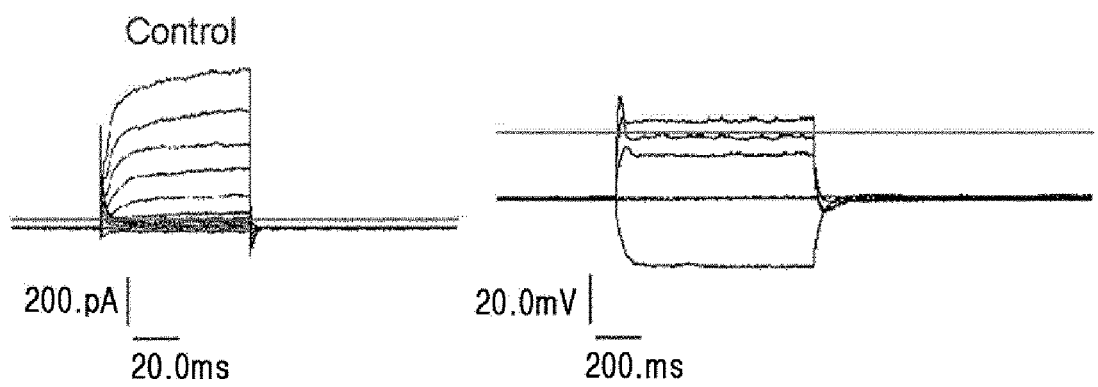

[FIG. 9C]
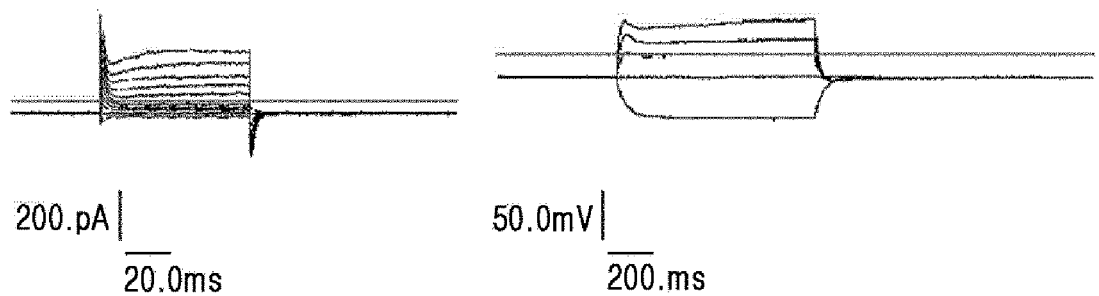
[FIG. 9D]
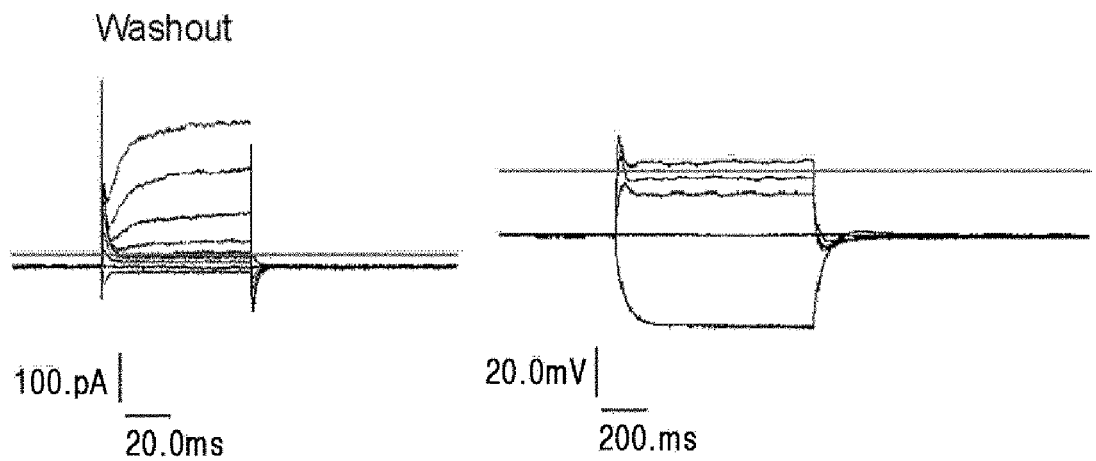

[FIG. 9E]
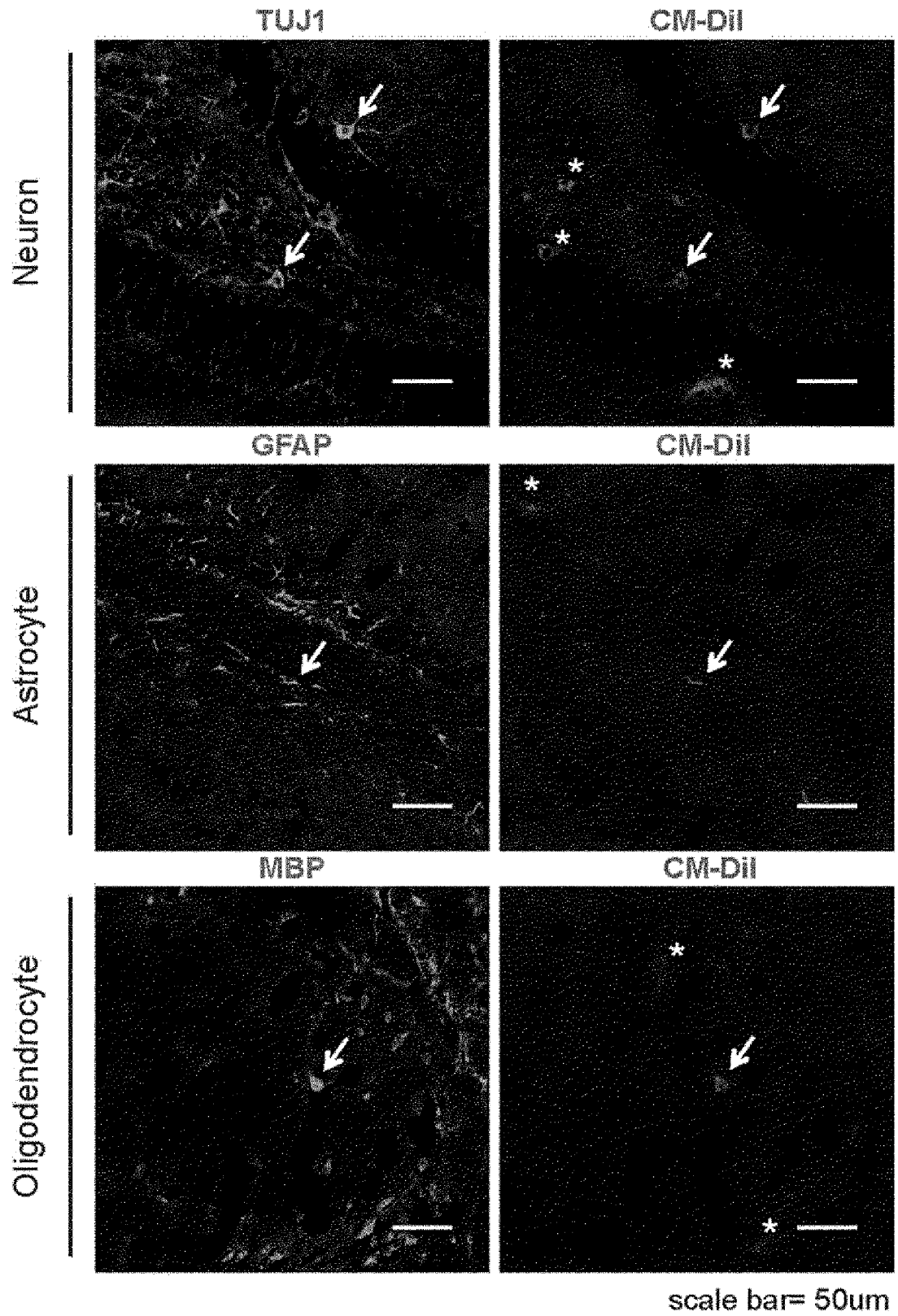

[FIG. 10A]
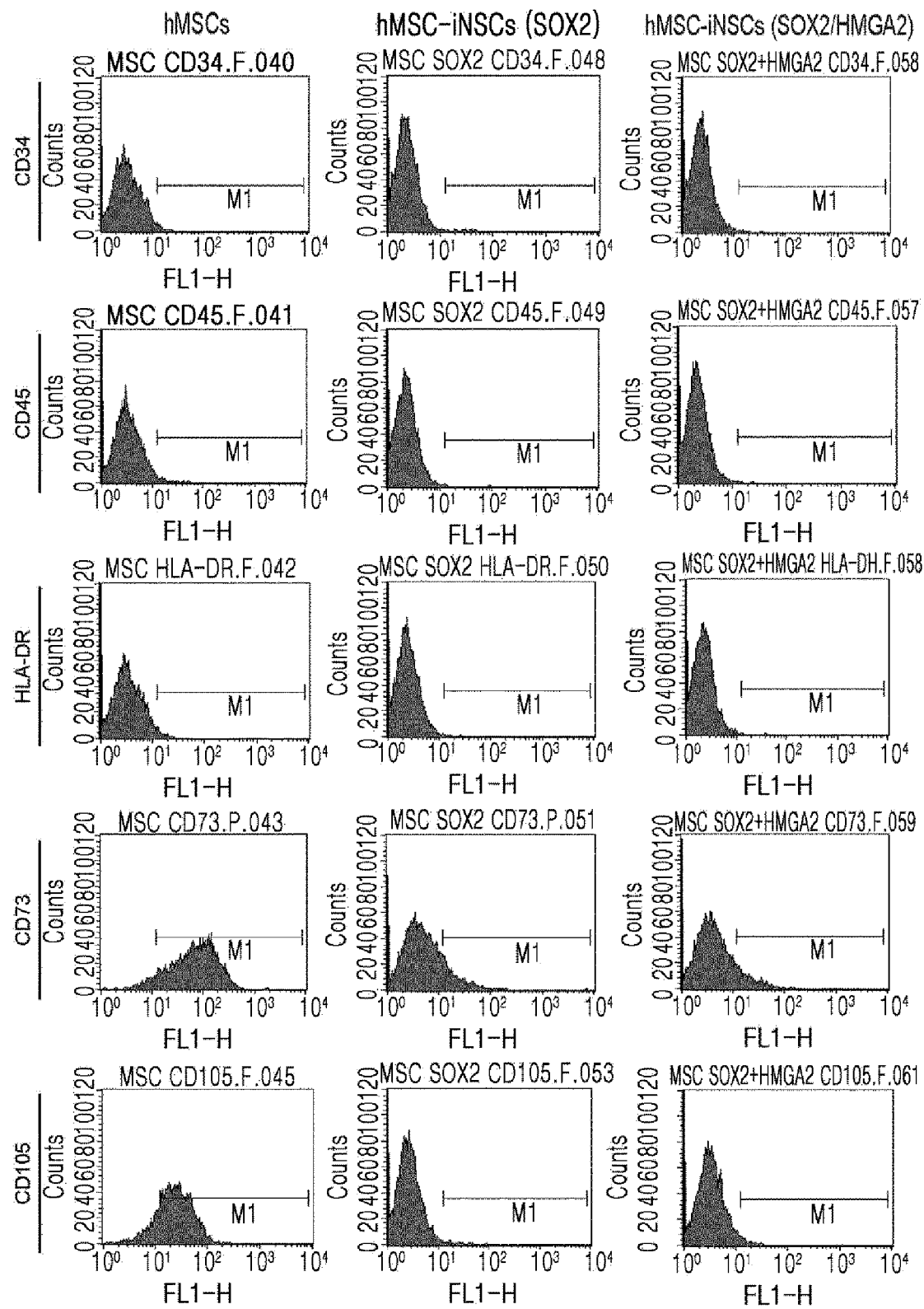

[FIG. 10B]
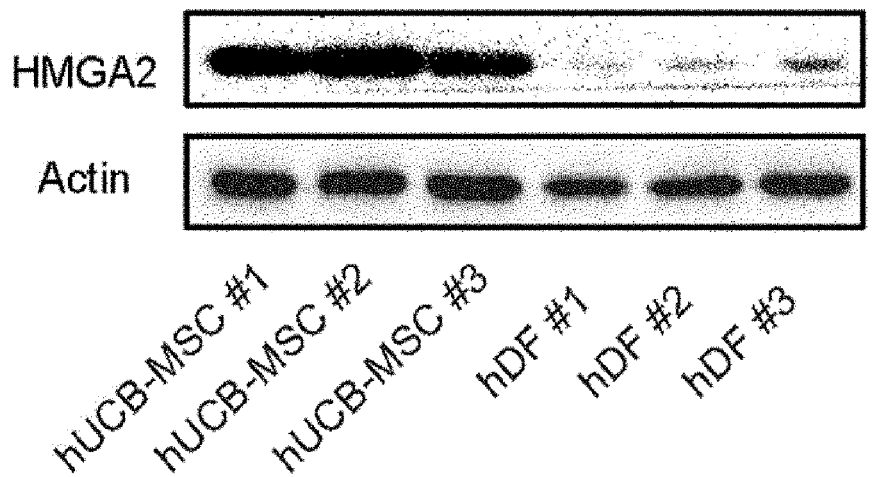
[FIG. 10C]
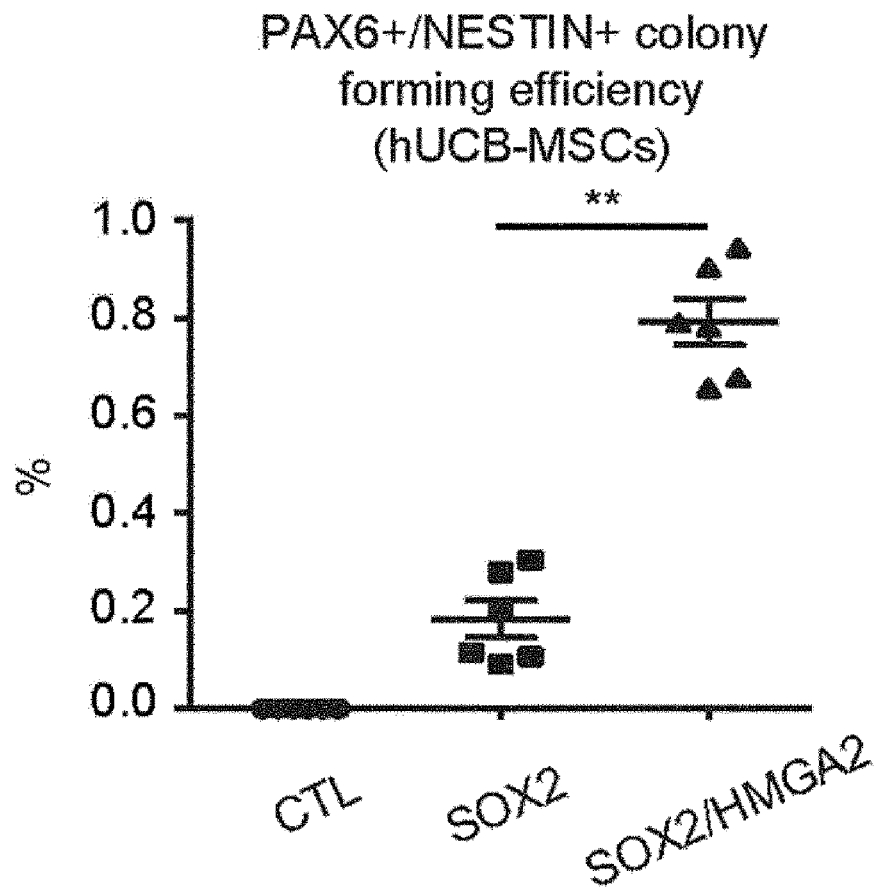

[FIG. 10D]
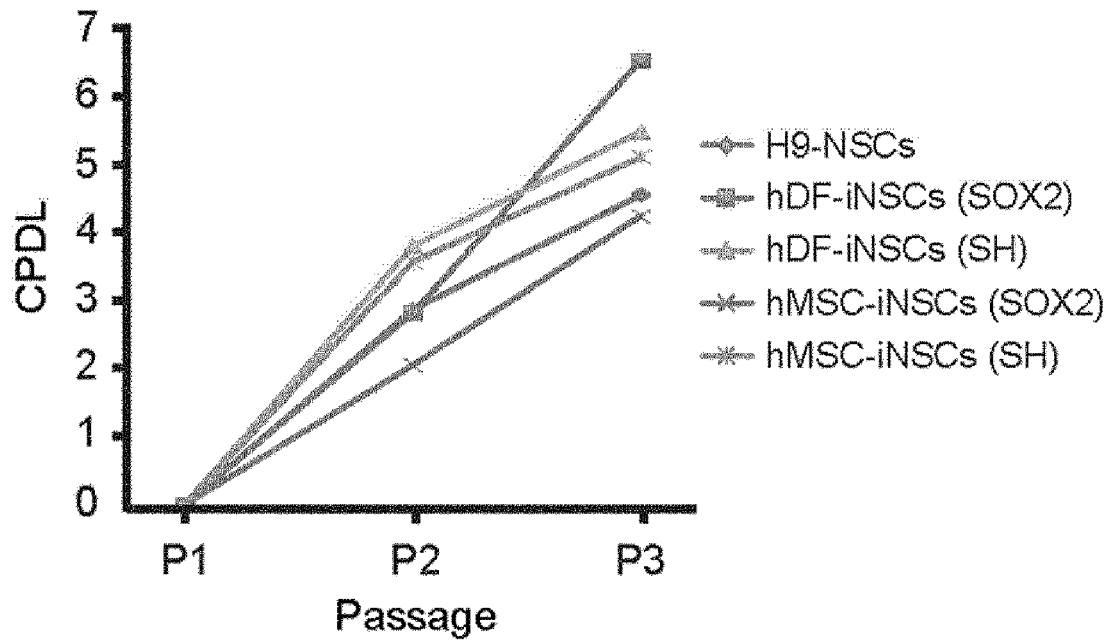
[FIG. 10E]
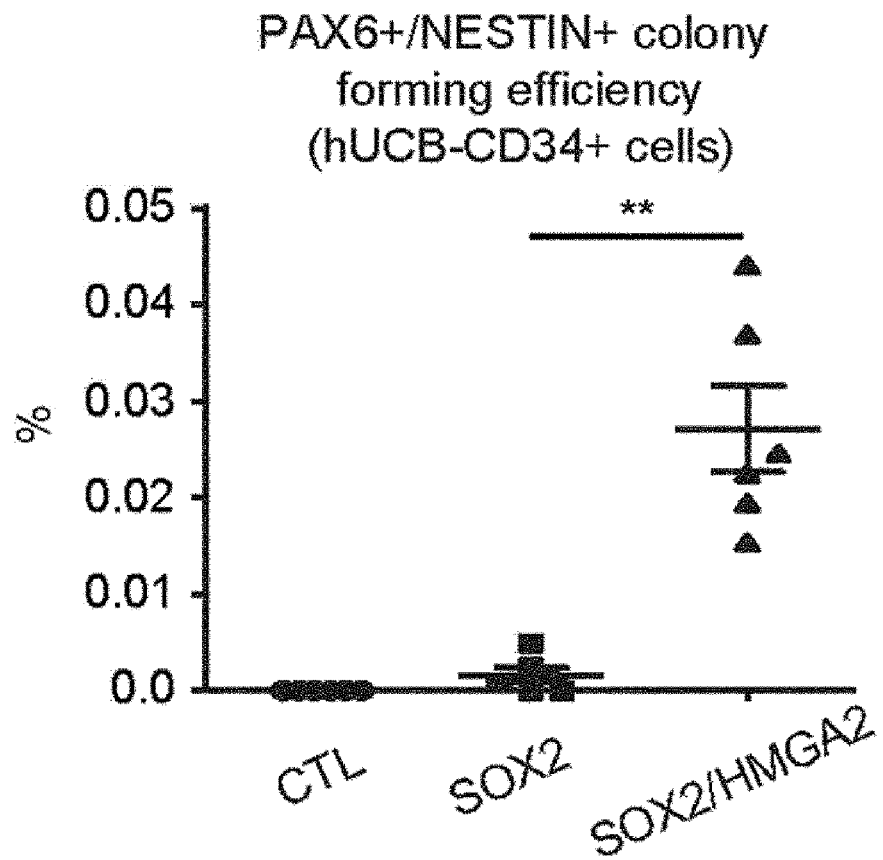

[FIG. 11]
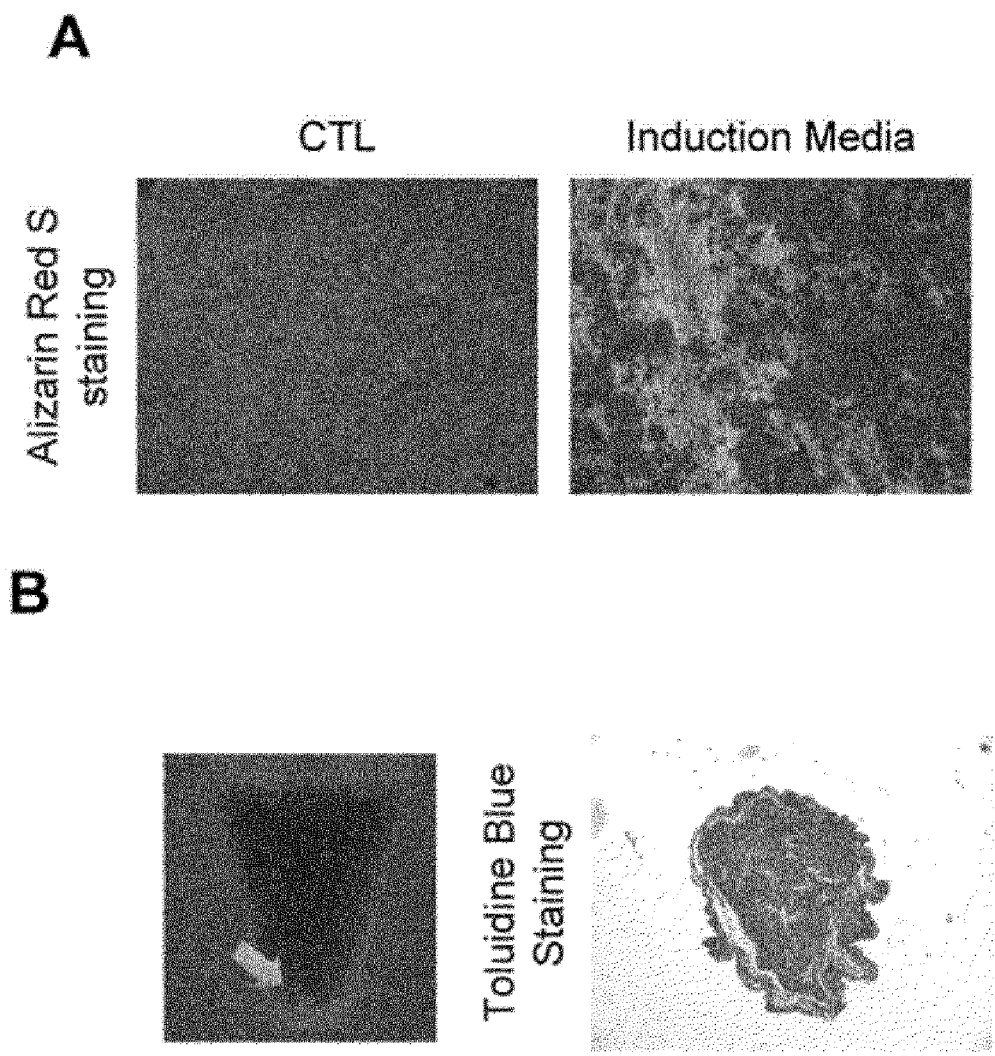

[FIG. 12]
Phase Contrast 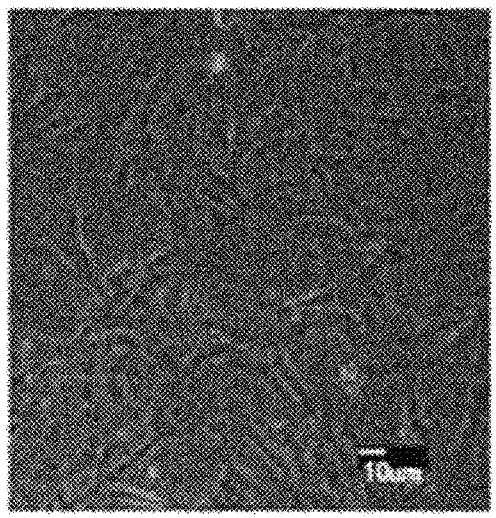 GFP 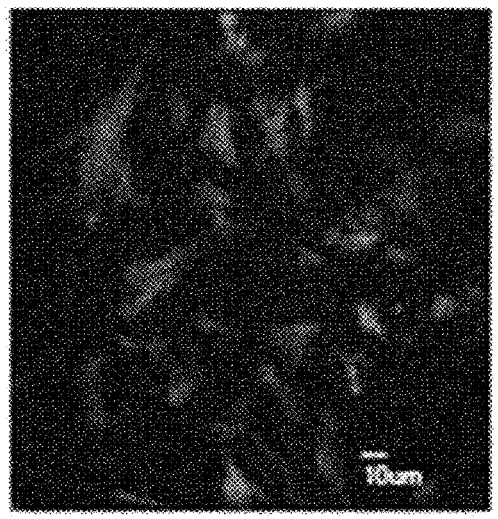

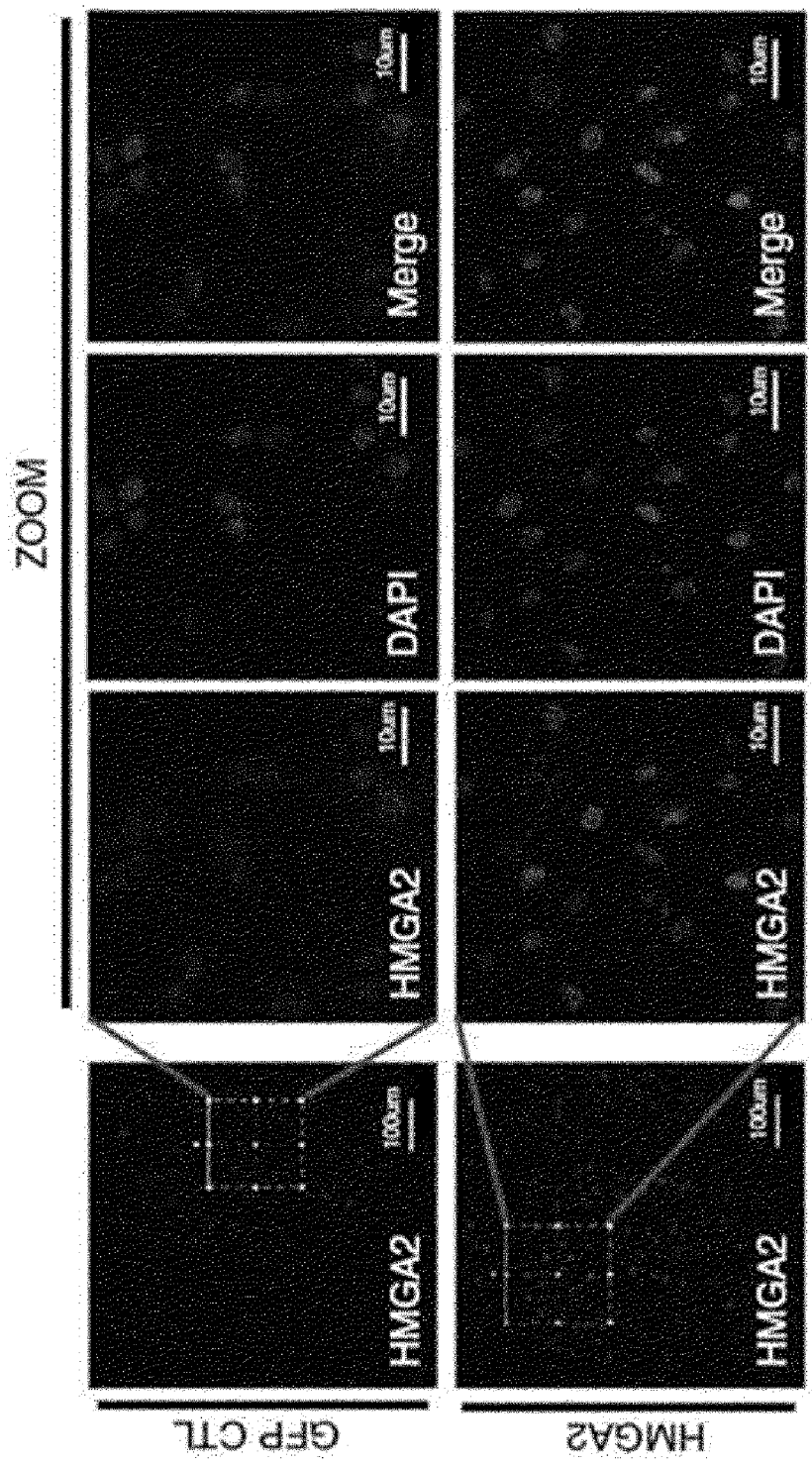
[FIG. 13]

[FIG. 14]
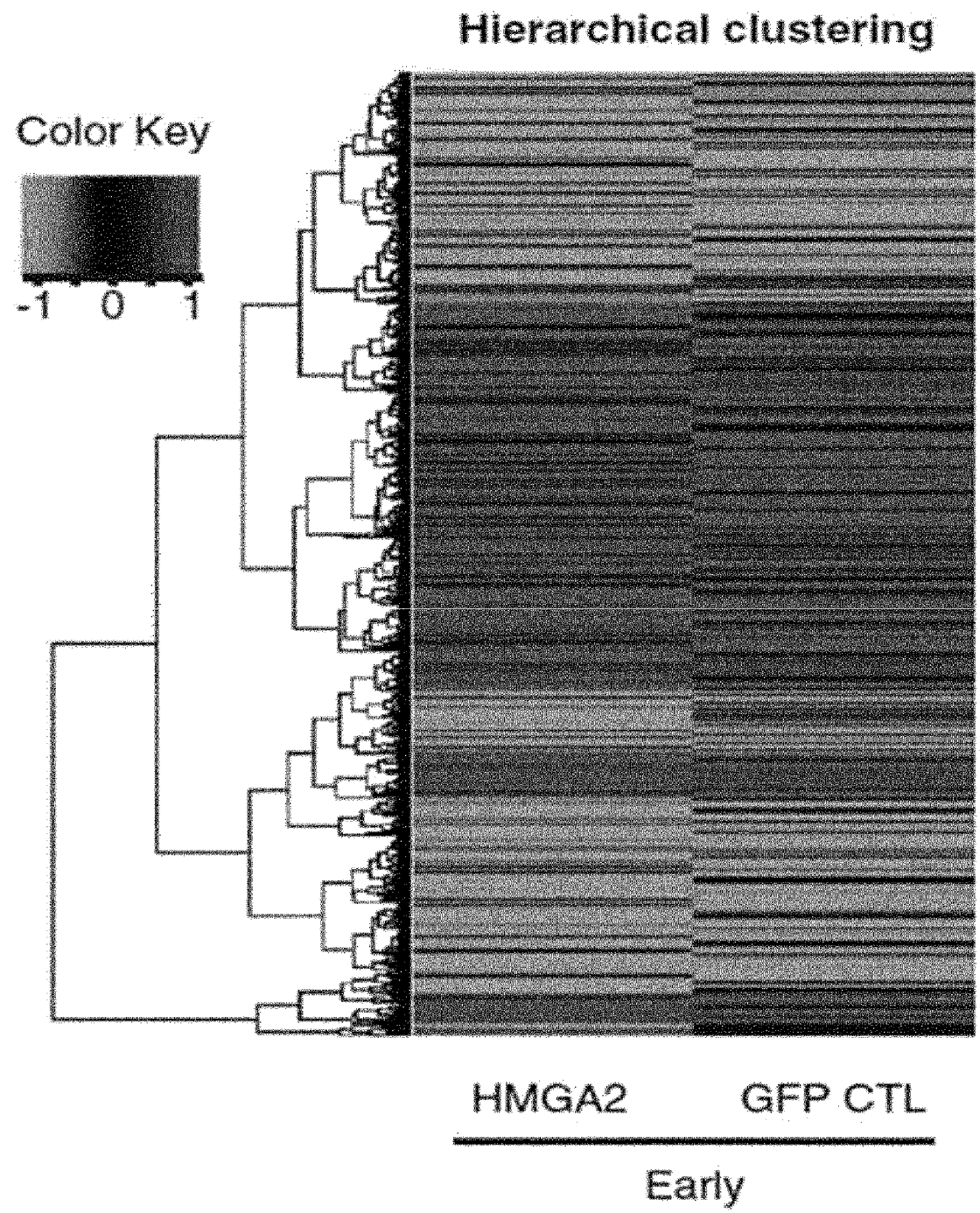

[FIG. 15]
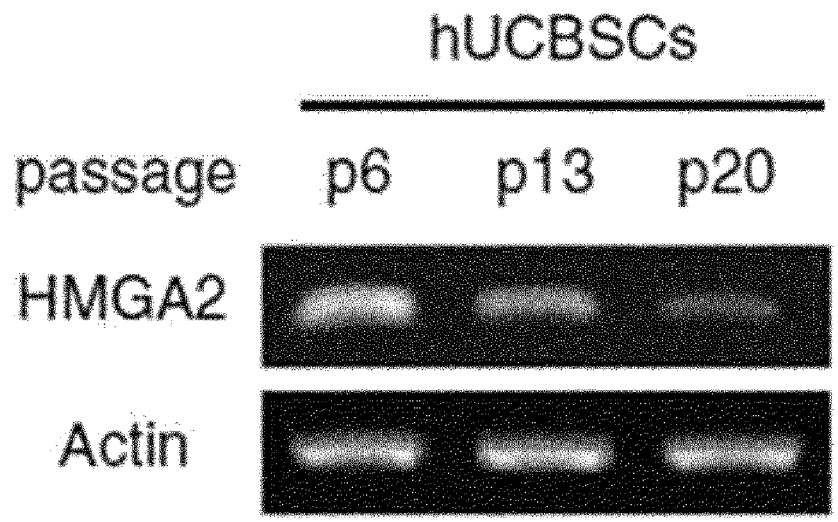
[FIG. 16]
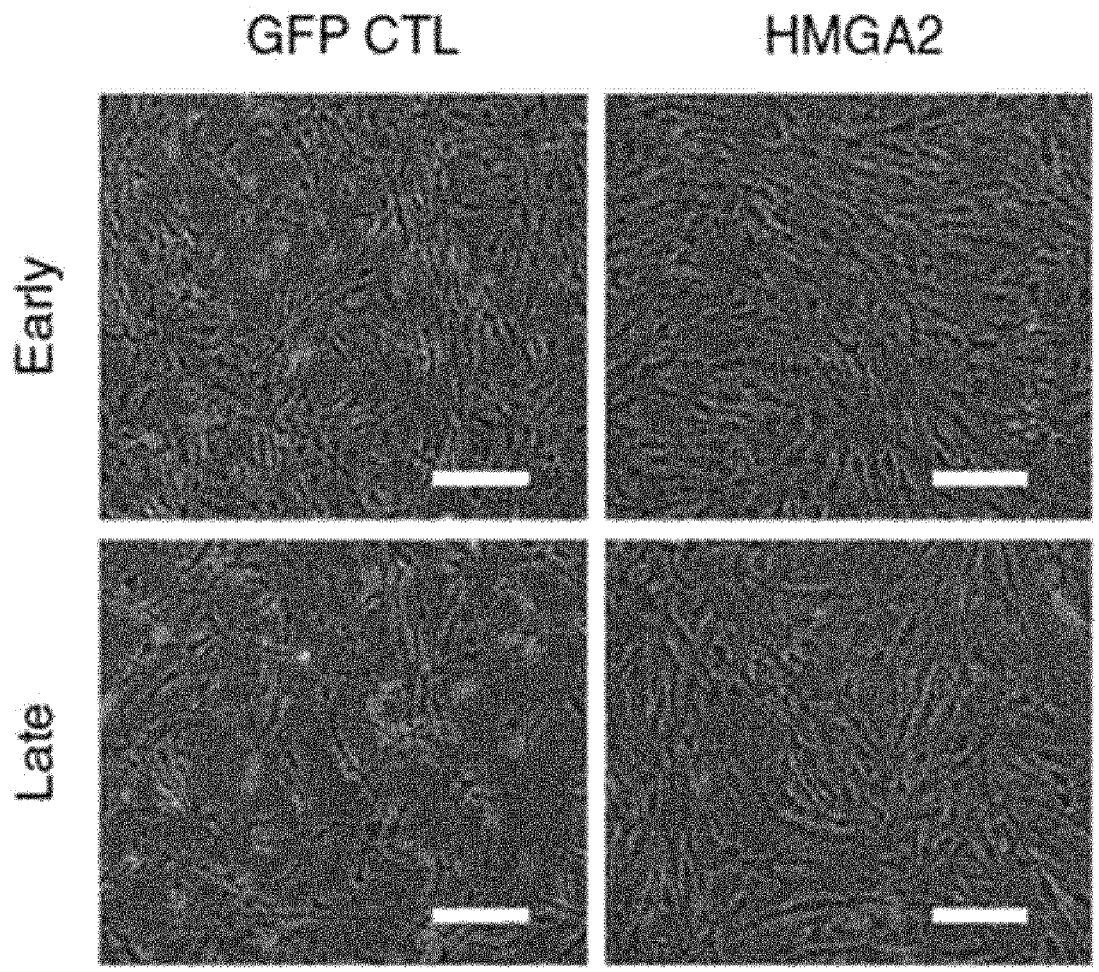

[FIG. 17]
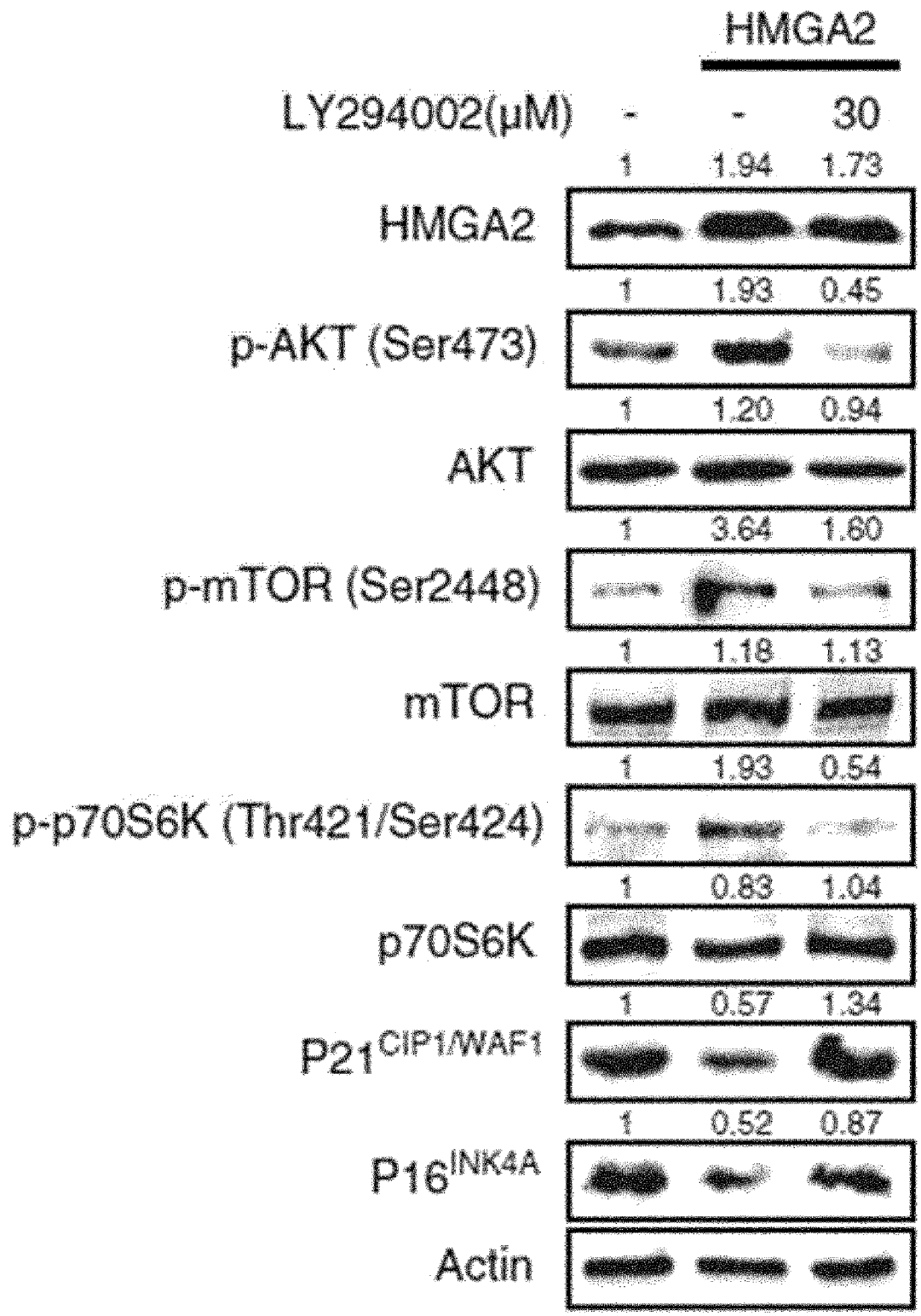

[FIG. 18]
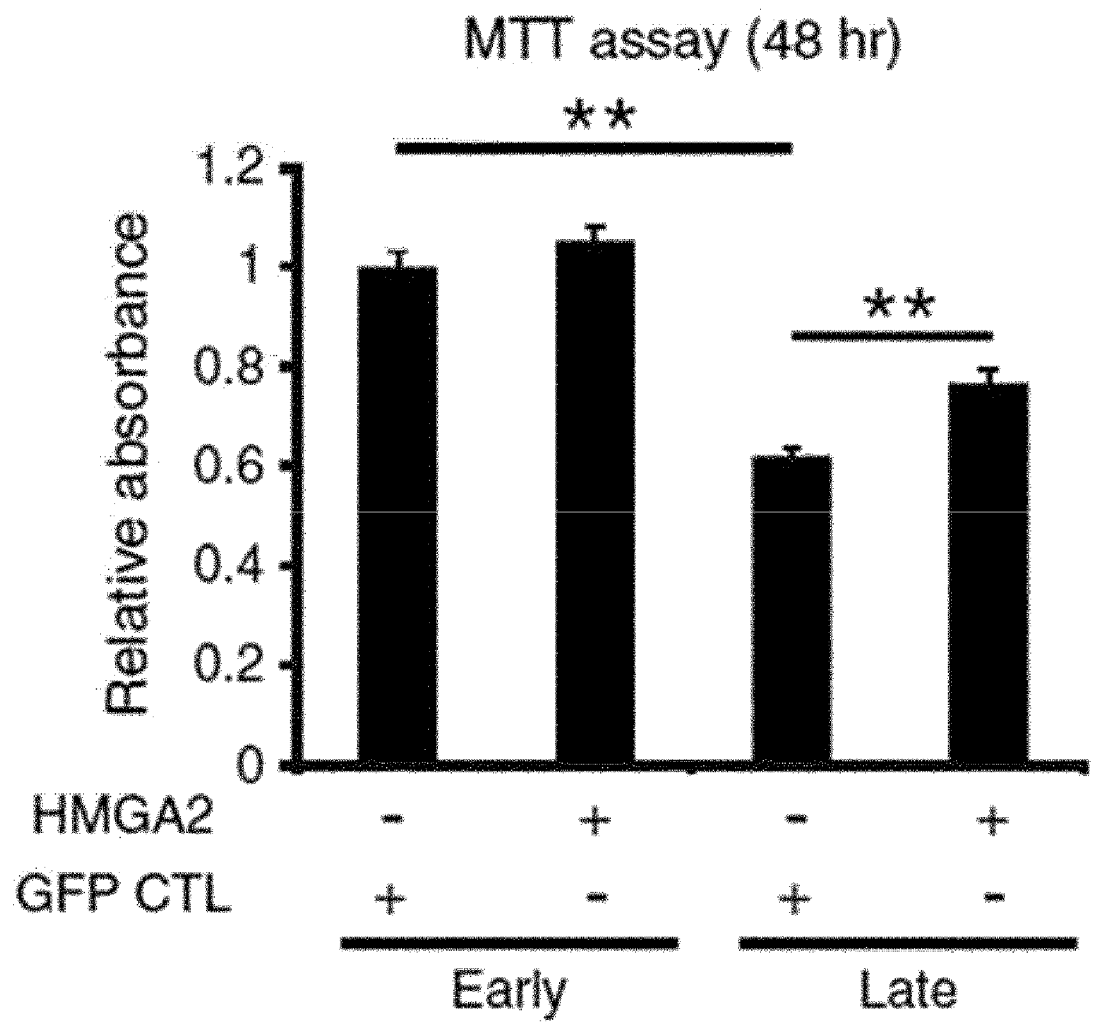

[FIG. 19]
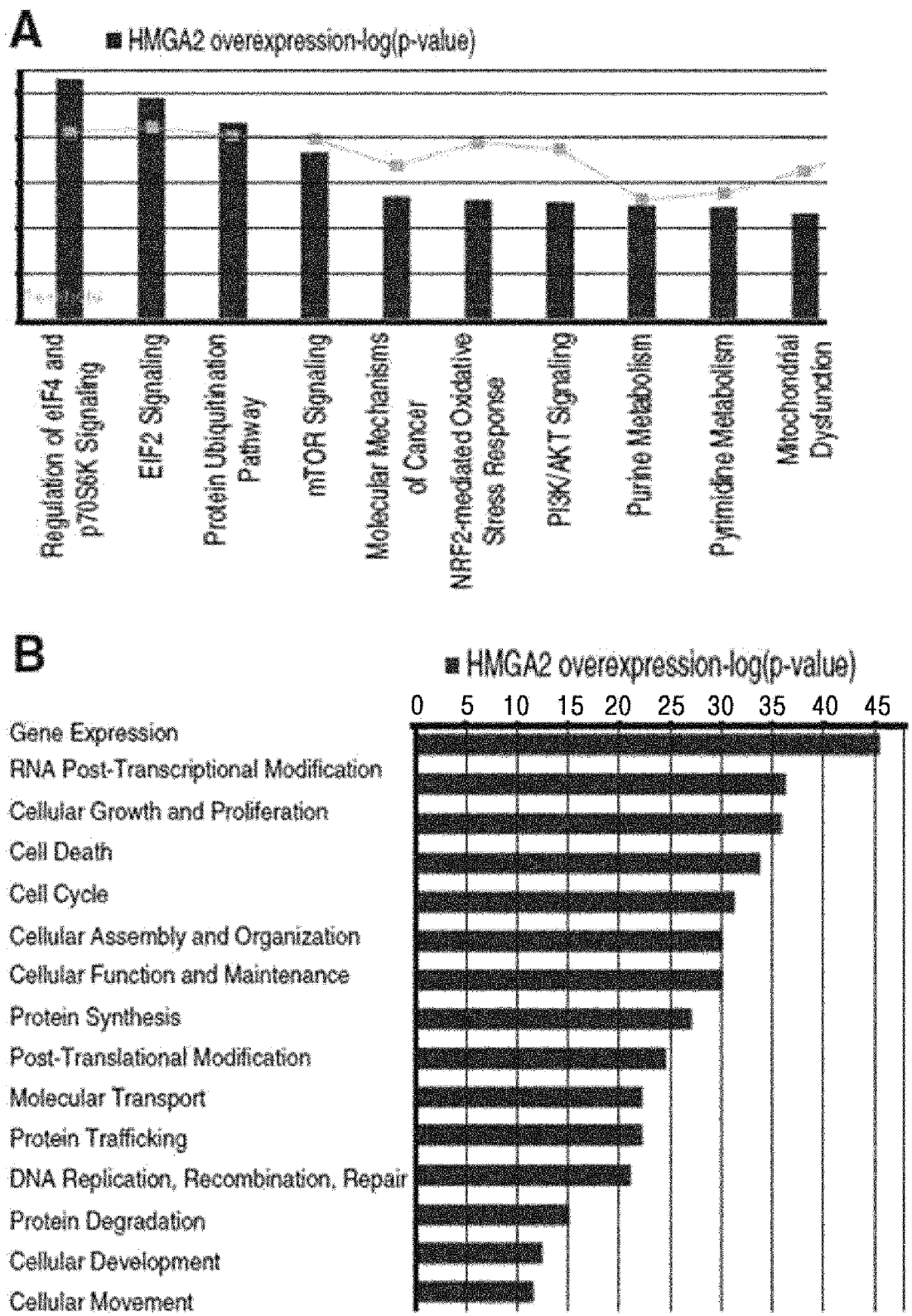

[FIG. 20]
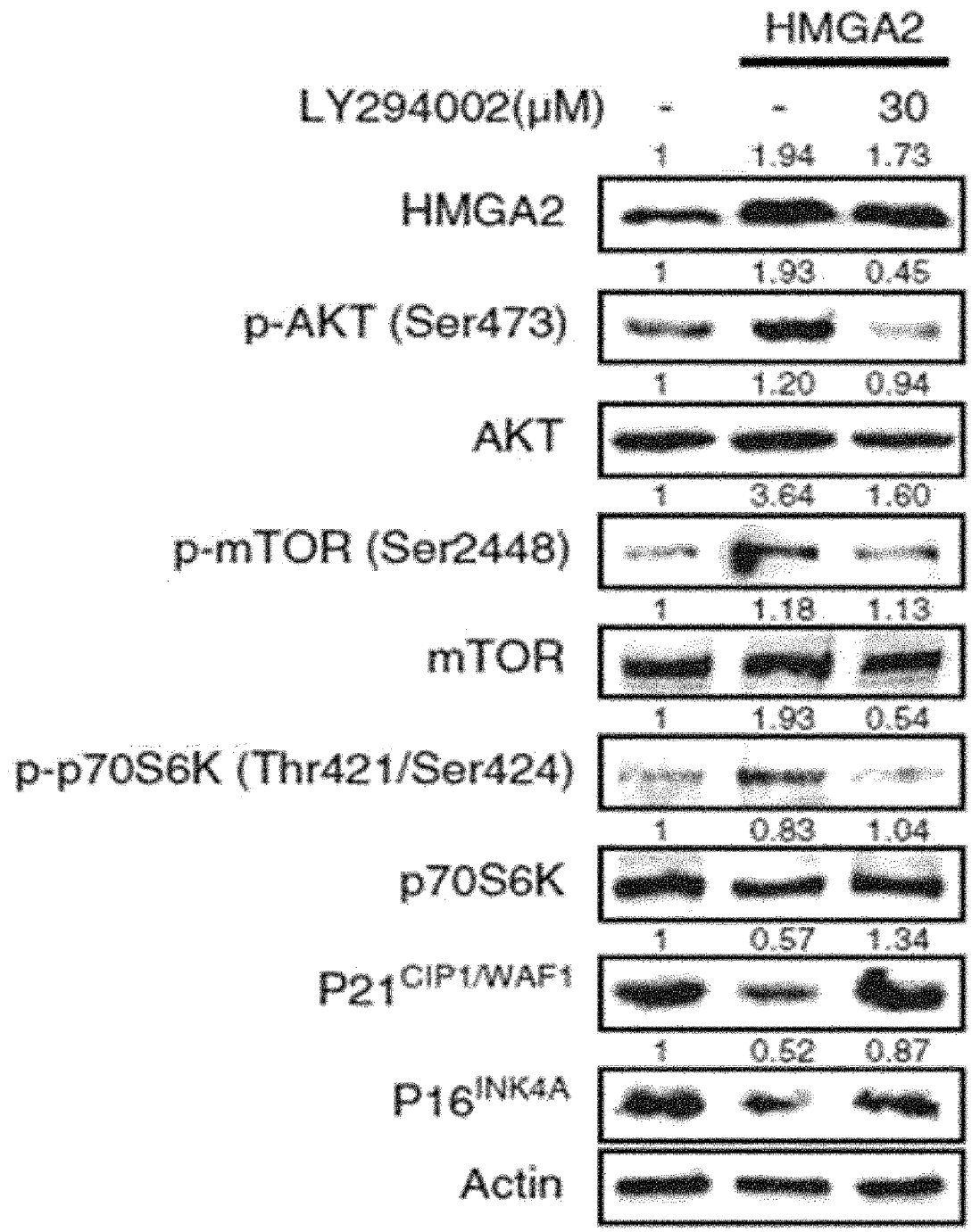

[FIG. 21]
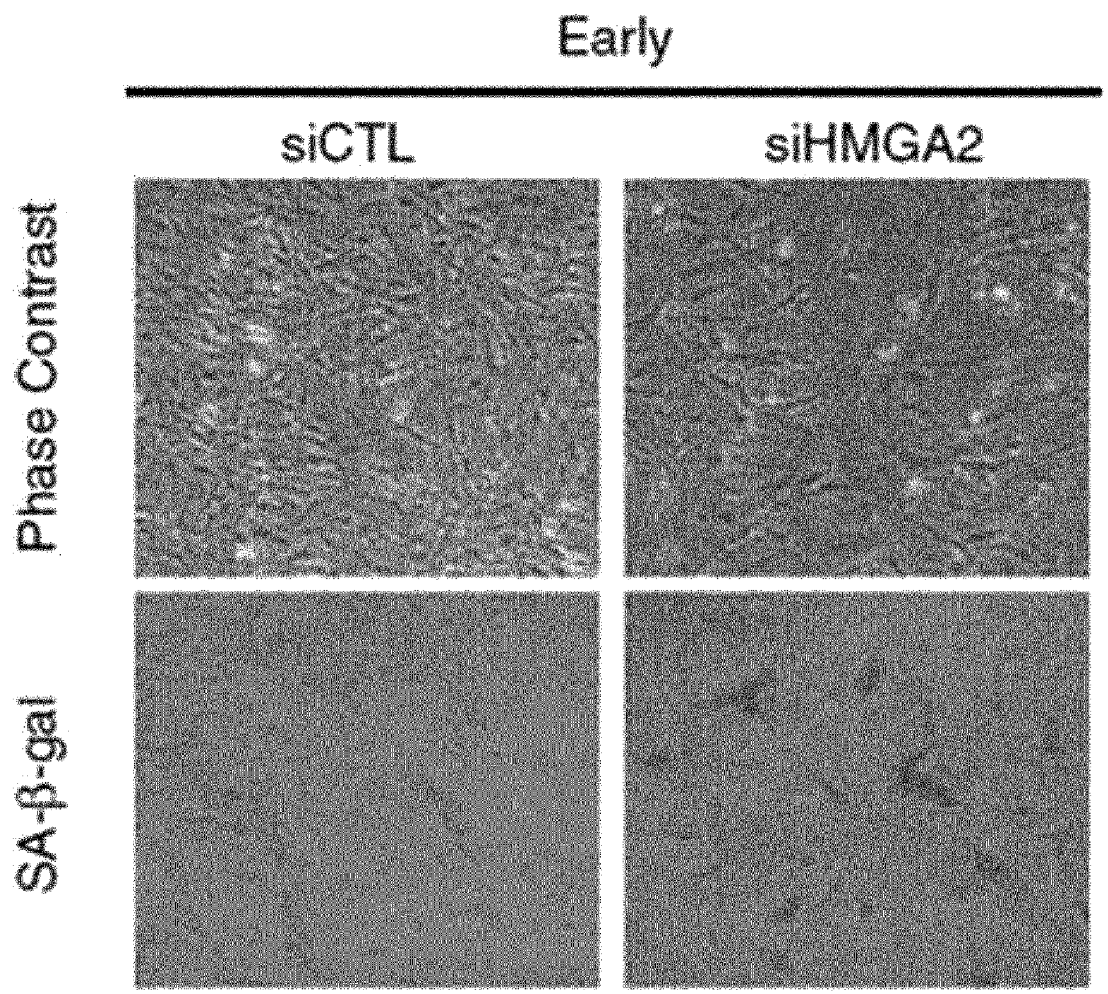

[FIG. 22]
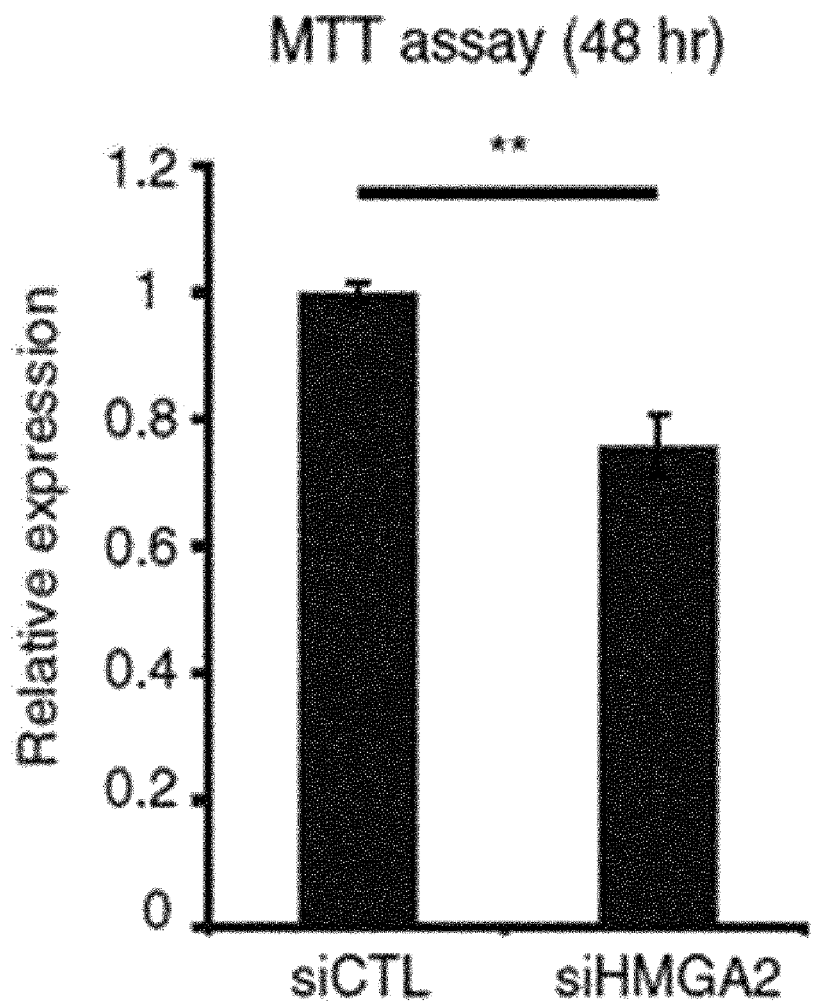

[FIG. 23]
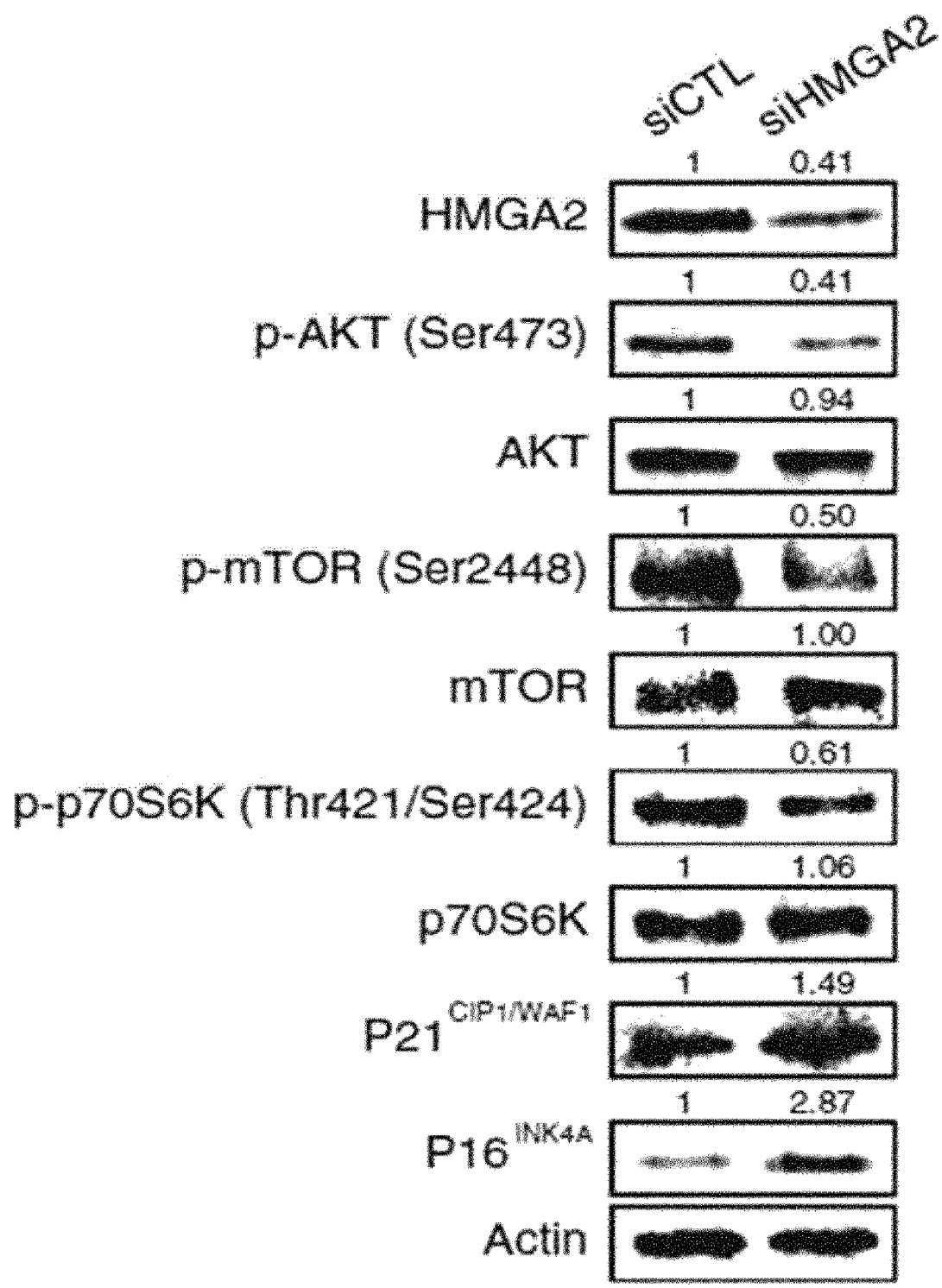

[FIG. 24]
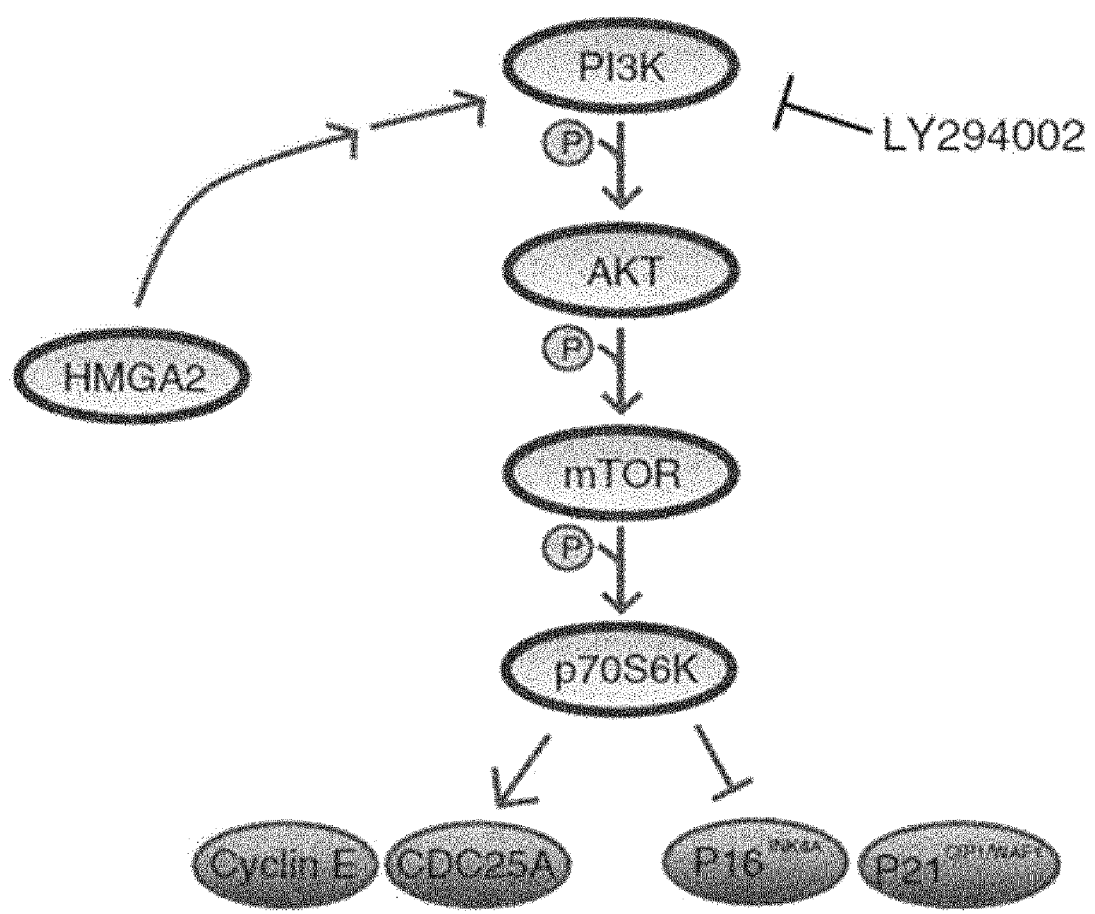

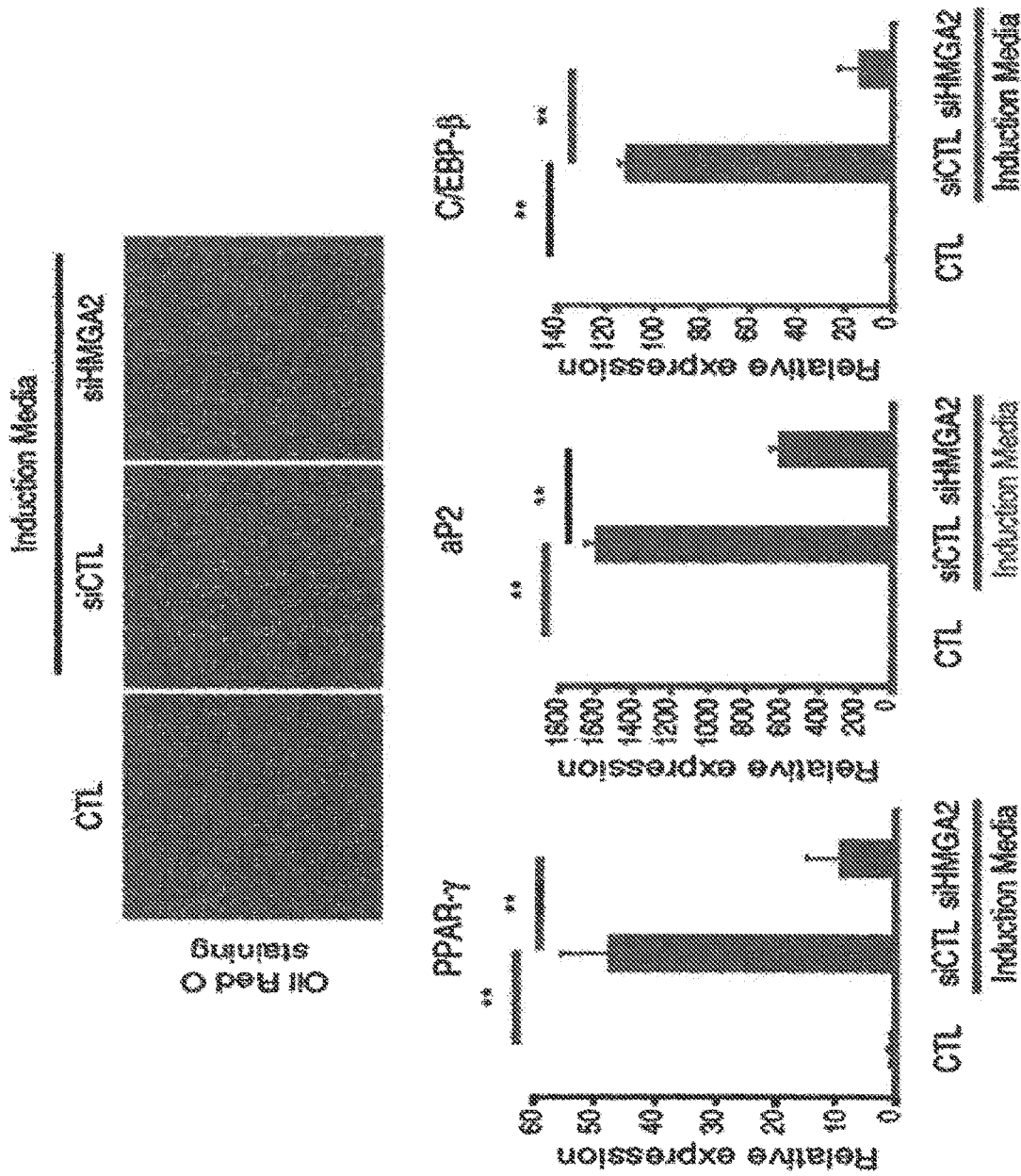
[FIG. 25]

[FIG. 26]
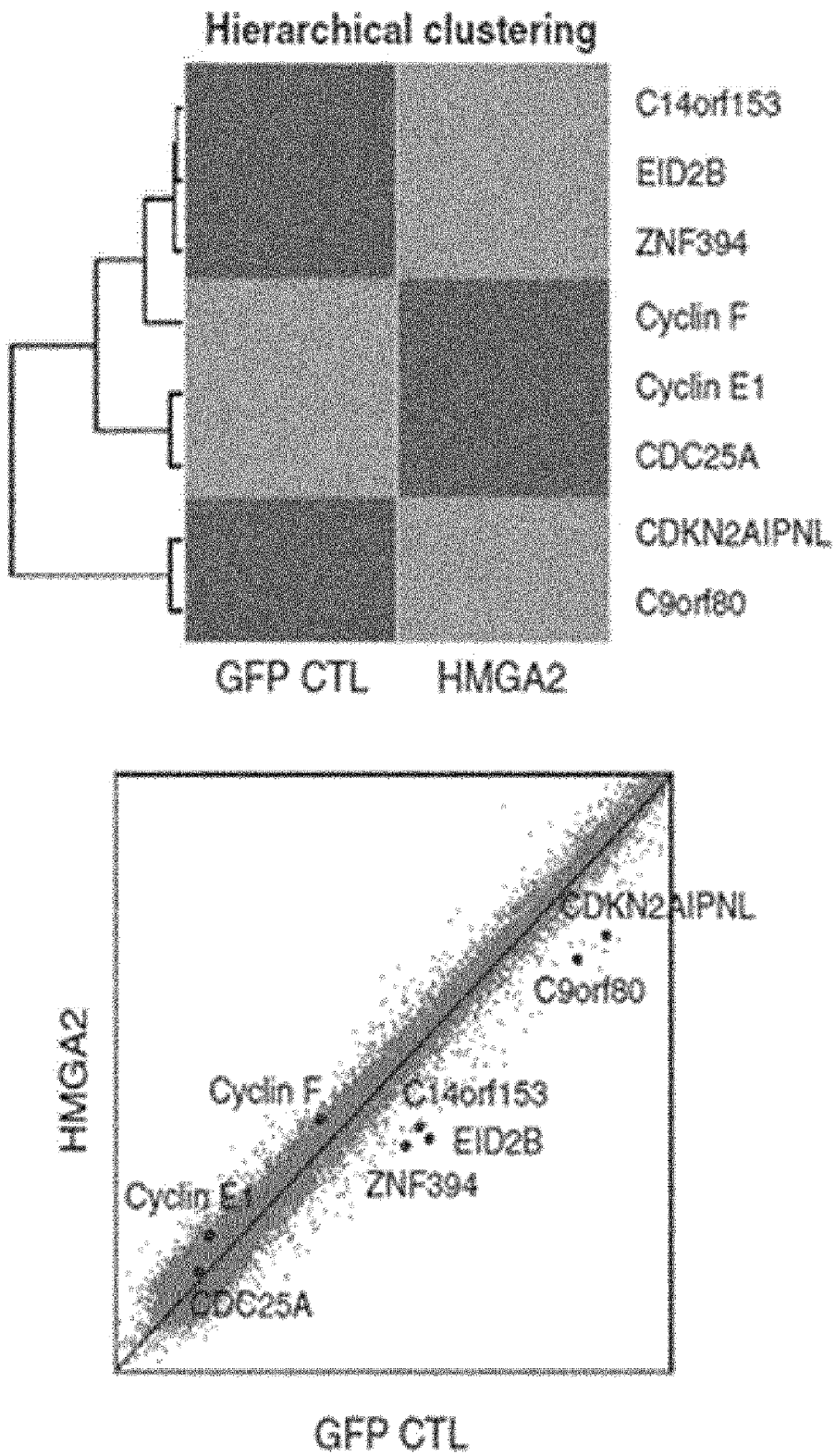

[FIG. 27]
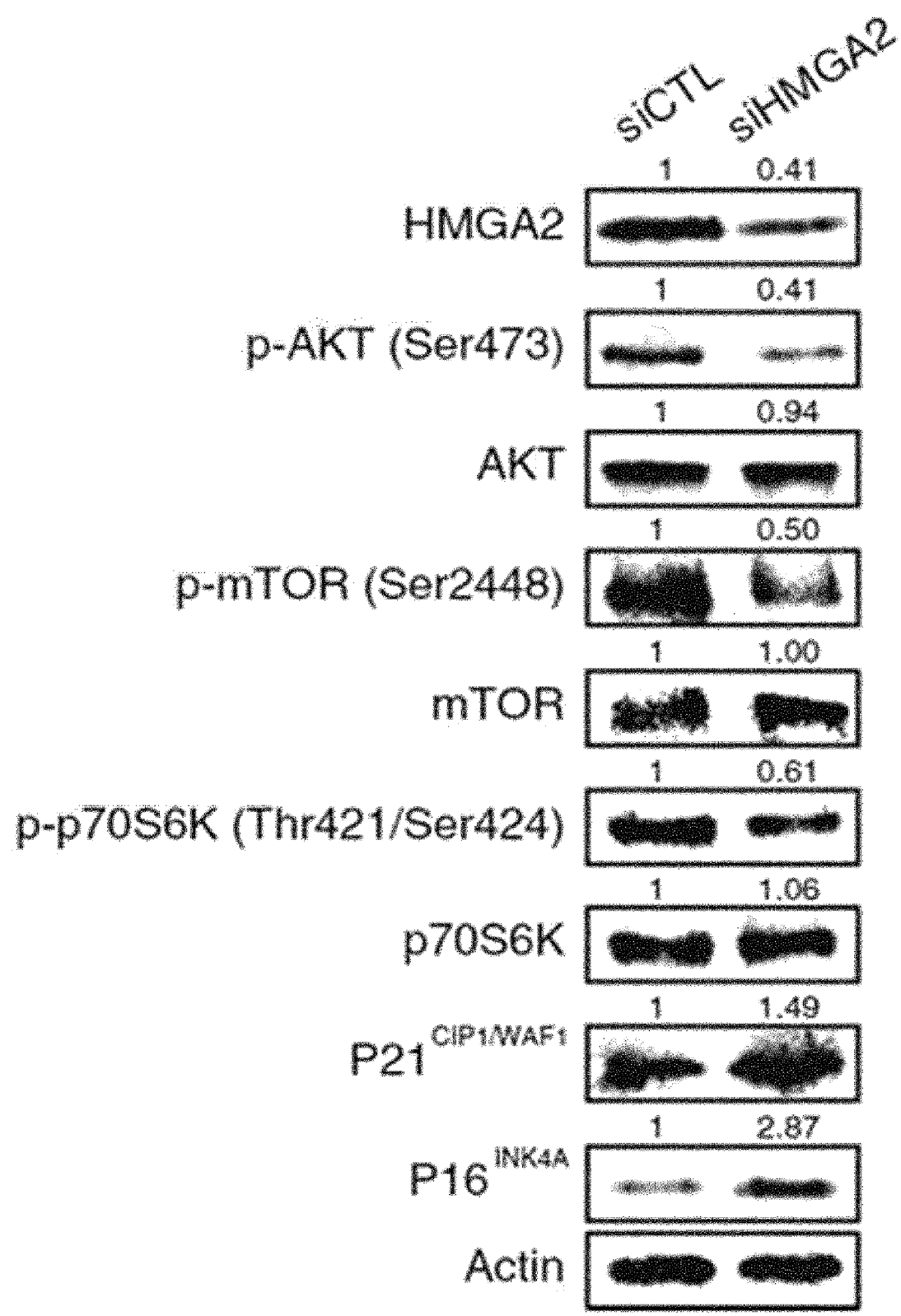

[FIG. 28]
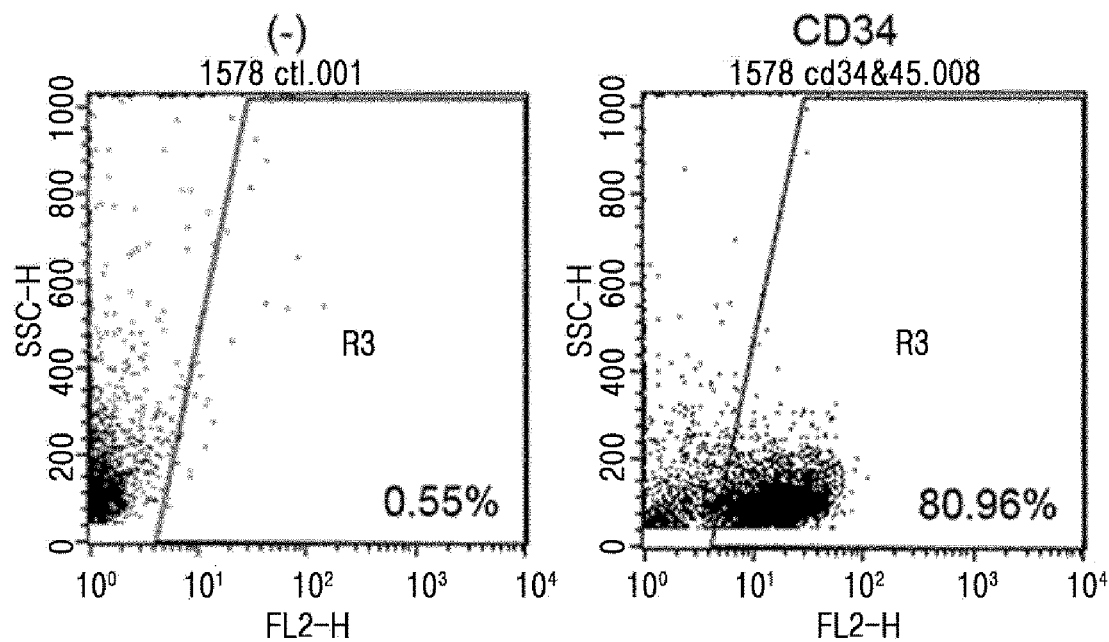
[FIG. 29]
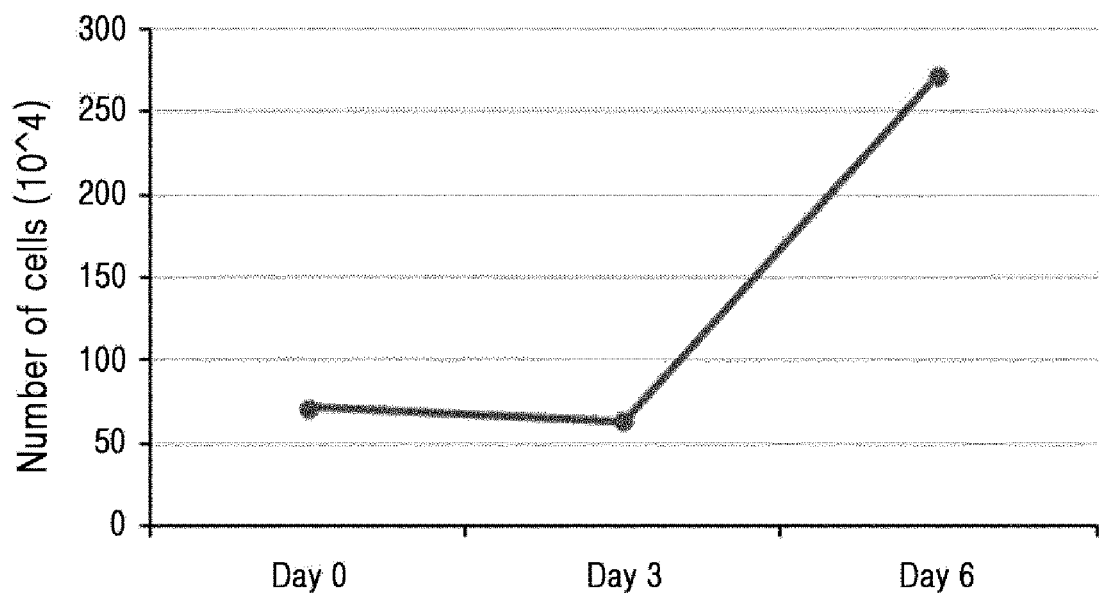

[FIG. 30]
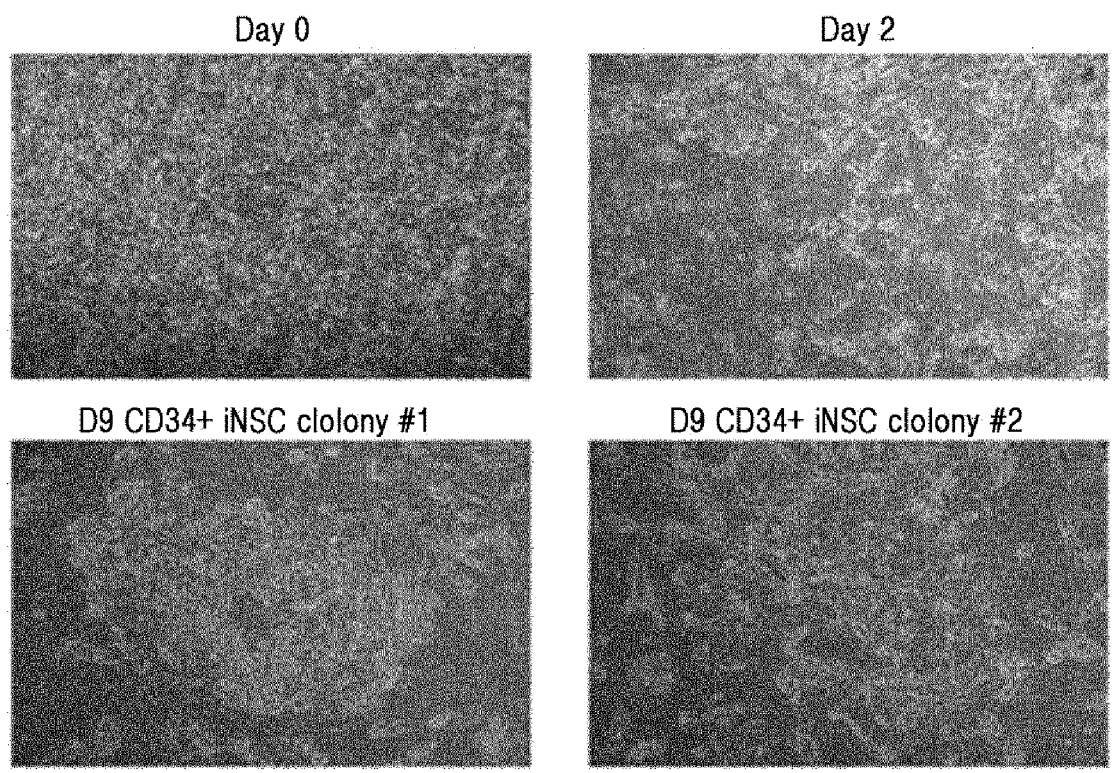

SEQUENCE LISTING

```
<160> NUMBER OF SEQ ID NOS: 3

<210> SEQ ID NO 1
<211> LENGTH: 25
<212> TYPE: DNA
<213> ORGANISM: Artificial Sequence
<220> FEATURE:
<223> OTHER INFORMATION: Synthetic primer

<400> SEQUENCE: 1
gggatatgat tagtatgtat ttttt                                    25

<210> SEQ ID NO 2
<211> LENGTH: 30
<212> TYPE: DNA
<213> ORGANISM: Artificial Sequence
<220> FEATURE:
<223> OTHER INFORMATION: Synthetic primer

<400> SEQUENCE: 2
aattttctcc atactatttc ttactctcct                               30

<210> SEQ ID NO 3
<211> LENGTH: 24
<212> TYPE: DNA
<213> ORGANISM: Artificial Sequence
<220> FEATURE:
<223> OTHER INFORMATION: Synthetic primer

<400> SEQUENCE: 3
agcggataac aatttcacac agga                                     24
```

METHOD OF PREPARING INDUCED NEURAL STEM CELLS REPROGRAMMED FROM NON-NEURONAL CELLS USING HMGA2

CROSS-REFERENCE TO RELATED APPLICATIONS

This application is the National Stage of International Application No. PCT/KR2014/002918, filed on 4 Apr. 2014 claiming the priority of KR 10-2013-0037790 filed on 6 Apr. 2013 and KR 10-2013-0087020 filed on 23 Jul. 2013, the content of each of which is incorporated by reference herein.

BACKGROUND OF THE INVENTION

1. Field of the Invention

The present invention relates to a method of preparing induced stem cells reprogrammed from non-neuronal cells using HMGA2.

2. Description of the Related Art

Stem cells are generally classified into totipotent stem cells and pluripotent stem cells. Totipotent stem cells have differentiation potential to give rise to all cells. Totipotent stem cells produce all different kinds of cells in the body, for example, fertilized egg cells. Pluripotent stem cells produce arbitrary cell types in the body, which are derived from the three major germ layers or embryos themselves.

Pluripotent stem cells, such as embryonic stem cells (ESC), proliferate rapidly while maintaining the capability to be differentiated into various cell types, i.e., pluripotency. Embryonic stem cells are a promising source of supply for cell transplantation therapy.

Until recently, pluripotent stem cells have been mainly produced by nuclear transplantation and cell fusion (Shinya Yamanaka, Pluripotency and Nuclear Reprogramming, Philos Trans R Soc Lond B Biol Sci. 363(1500): 2079-2087 (Jun. 27, 2008)). However, both methods employ embryonic stem cells, and thus there is an ethical dilemma.

However, due to the recent discovery of induced pluripotent stem cells (iPSC), it has become possible to overcome the problems associated with the use of embryonic stem cells. "Induced pluripotent stem cells (iPSC)" are cells which exhibit properties similar to those of embryonic stem cells (ESC). The induced pluripotent stem cells were first produced by increasing the expression of defined factors in mouse fibroblasts in 2006 (Takahashi, Y. and S. Yamanaka, Induction of Pluripotent Stem Cells from Mouse Embryonic and Adult Fibroblast Cultures by Defined Factors, Cell 126: 663-676 (2006)) and human fibroblasts in 2007 (Yu Junying et al., Induced Pluripotent Stem Cell Lines Derived from Human Somatic cells, Science 318: 1917-1920 (2007), Takahashi, K. et al., Induction of Pluripotent Stem Cell From Adult Human Fibroblasts by Defined Factors, Cell 131: 861-872 (2007)).

These studies, for the initiation of reprogramming of mature somatic cells into iPSCs, included Oct-3/4, Sox2, Klf4, and c-Myc (Takahashi, Cell 126: 663-676; Takahashi, Cell 131:861-872) and used Oct4, Sox2, Nanog, and Lin28 (Junying, Cell 318: 1917-1920). However, iPSCs have limitations in that they cannot be converted into desired cells in vivo because they can cause the occurrence of teratoma as in embryonic stem cells, and at the same time, cannot adequately control differentiation at the time of in vivo transplantation.

Accordingly, in order to overcome these limitations, a technology for differentiation into cells of a particular lineage via direct conversion/reprogramming has recently been highlighted. This is a technology which can directly induce particular cells without going through a pluripotent state, by introducing a particular lineage-specific gene to a cell which has not completed differentiation, i.e., a fibroblast, and can exclude the risk of teratoma formation by pluripotent cells. In particular, for neuronal cells which, once damaged, may remain damaged permanently, various lines of studies have been actively performed to attempt direction induction. As a result, a research team led by U.S. professor Marius Wernig succeeded in directly inducing neuronal cells [Vierbuchen T, Ostermeier A, Pang Z P, Kokubu Y, Sudhof T C, Wernig M (2010) Direct conversion of fibroblasts to functional neurons by defined factors. Nature 463(7284):1035-1041. doi: 10.1038/nature08797]. However, it is difficult to culture induced neurons without self-renewal capacity in vitro for more than a certain period of time and to thus secure a sufficient amount of cells, and therefore it is not practically possible to obtain a sufficient amount of cells necessary for cell therapies, including a molecular cytological mechanism involved in direct reprogramming.

Later, two German research teams succeeded in preparing induced neural stem cells (iNSC) by introducing a gene to mouse fibroblasts (Thier M. Worsdorfer P, Lakes Y B, Gorris R, Herms S, Opitz T, Seiferling D, Quandel T, Hoffmann P, Nothen M M, Brustle O, Edenhofer F (2012) Direct conversion of fibroblasts into stably expandable neural stem cells. Cell Stem Cell 10(4):473-479. doi:10.1016/j.stem.2012.03.003). Regarding humans, there was a report that the induction of iNSC by introducing a single SOX2 gene to a fibroblast was performed successfully (Thier M, Worsdorfer P, Lakes Y B, Gorris R, Herms S, Opitz T, Seiferling D, Quandel T, Hoffmann P, Nothen M M, Brustle O, Edenhofer F (2012) Direct conversion of fibroblasts into stably expandable neural stem cells. Cell Stem Cell 10(4): 473-479. doi:10.1016/j.stem.2012.03.003).

However, the conventional methods of preparing induced neuronal cells using these factors had limitations in that they had low induction efficiency and were unable to proliferate the neuronal cells, and were thus not useful for therapeutic purposes.

SUMMARY OF THE INVENTION

In order to solve the problems shown in the conventional methods, the present invention aims at providing a novel method for producing induced neural stem cells or neuronal cells from differentiated cells, and the induced neural stem cells or neuronal cells produced thereof by the method.

An object of the present invention is to provide a kit for inducing reprogramming of a non-neuronal cell into a neural stem cell (NSC), including (a) an SRY (sex determining region Y)-box 2 (SOX2) protein or a nucleic acid molecule encoding the SOX2 protein; and (b) a high mobility group at-hook 2 (HMGA2) protein or a nucleic acid molecule encoding the HMGA2 protein.

Another object of the present invention is to provide a method for preparing an induced neural stem cell, which was reprogrammed from a non-neuronal cell, or a neuronal cell differentiated therefrom, including (a) delivering to a non-neuronal cell a SOX2 protein or a nucleic acid molecule encoding the SOX2 protein, and an HMGA2 protein or a nucleic acid molecule encoding the HMGA2 protein, or increasing the expression of the SOX2 protein and the HMGA2 protein in a non-neuronal cell; and (b) culturing the cells in step (a).

Still another object of the present invention is to provide an induced neural stem cell prepared by the above method; or a neuronal cell differentiated from the induced neural stem cell.

Still another object of the present invention is to provide a cell therapy product for neuronal cell regeneration including the induced neural stem cell; or the neuronal cell differentiated from the induced neural stem cell, as an active ingredient.

Still another object of the present invention is to provide a pharmaceutical composition for preventing or treating neuronal cell damage-associated diseases, including a SOX2 protein or a nucleic acid molecule encoding the SOX2 protein; and an HMGA2 protein or a nucleic acid molecule encoding the HMGA2 protein, as active ingredients.

Still another object of the present invention is to provide a method of screening a regeneration promoter or a regeneration inhibitor for a neural stem cell or neuronal cell, including: 1) preparing an isolated non-neuronal cell; 2) inducing the production of an induced neural stem cell by delivering, to a non-neuronal cell, a SOX2 protein or a nucleic acid molecule encoding the SOX2 protein; and an HMGA2 protein or a nucleic acid molecule encoding the HMGA2 protein, or increasing the expression of the SOX2 protein and the HMGA2 protein in a non-neuronal cell; 3) optionally, differentiating the induced neural stem cell produced in step 2) into a neuronal cell; and 4) confirming the production of the induced neural stem cell or the neuronal cell according to the presence of treatment of a candidate material, by treating with the candidate material after step 1 or step 2.

Still another object of the present invention is to provide a method of screening a personal customized neuronal cell therapy product, including: 1) preparing an isolated non-neuronal cell; 2) inducing the production of an induced neural stem cell by delivering, to a non-neuronal cell, a SOX2 protein or a nucleic acid molecule encoding the SOX2 protein; and an HMGA2 protein or a nucleic acid molecule encoding the HMGA2 protein, or increasing the expression of the SOX2 protein and the HMGA2 protein in a non-neuronal cell; 3) differentiating the induced neural stem cell produced in step 2) into a neuronal cell; and 4) confirming the neuronal cell therapy product customized to a subject from which the non-neuronal cell is derived, by treating the non-neuronal cell formed in step 3 with the candidate material.

Still another object of the present invention is to provide a composition for promoting reprogramming of non-neuronal cells into neural stem cells (NSC) including an HMGA2 protein or a nucleic acid encoding the HMGA2 protein as an active ingredient.

Still another object of the present invention is to provide a composition for cell proliferation including an HMGA2 protein or a nucleic acid encoding the HMGA2 protein as an active ingredient.

Still another object of the present invention is to provide a composition for inhibiting cellular senescence including an HMGA2 protein or a nucleic acid encoding the HMGA2 protein as an active ingredient.

Advantageous Effect of the Invention

The method of the producing the induced neural stem cells according to the present invention enables preparation of the induced neural stem cells from non-neuronal cells when using only two inducing factors of SOX2 and HMGA2. Therefore, the method of the present invention can prepare induced neural stem cells in a more efficient manner than the conventional methods using four or five inducing factors. Additionally, the method of the present invention shows significantly higher inducing efficiency and proliferation capacity than when SOX2 is used alone, thus increasing its potency to be used for therapeutic purposes.

In the present invention, Oct4 was not used in the combination of reprogramming factors during the reprogramming process into the neural stem cells, and thus the differentiated cells were directly reprogrammed into neural stem cells, without going through the dedifferentiation process. The thus-prepared induced neural stem cells can not only retain self-renewal capacity and proliferation capacity when transplanted with mouse brain tissues but can also be sufficiently differentiated into nerve related cells such as neurons, astrocytes, oligodendrocytes, etc., and are thus expected to be used for therapeutic purposes.

BRIEF DESCRIPTION OF THE DRAWINGS

FIG. 1A shows the morphology of human neonatal dermal fibroblasts (hDFs) observed under a bright-field microscope.

FIG. 1B shows the iNSC induced from SOX2-transduced hDF observed under a bright-field microscope.

FIG. 1C shows the image of early neurosphere-like colonies formed by SOX2-transduction observed under a bright-field microscope.

FIG. 1D shows the result of immunocytochemical analysis of NSC-specific marker proteins of hDF-iNSC using antibodies against PAX6 and NESTIN.

FIG. 1E shows the result of immunocytochemical analysis of NSC-specific marker proteins of hDF-iNSC using antibodies against VIMENTIN and SOX2.

FIG. 1F shows the Heat map of global miRNA expression profiles in hDF, H9-NSC, and hDF-iNSC (SOX2).

FIG. 1G shows the heat maps of nervous system-specific miRNA in hDF, H9-NSC, and hDF-iNSC (SOX2).

FIG. 1H shows the results of quantitative real time PCR of miR-124-3p in hDF, H9-NSC, and hDF-iNSC (SOX2).

FIG. 1I shows the results of quantitative real time PCR of miR-9-5p/-3p in hDF, H9-NSC, and hDF-iNSC (SOX2).

FIG. 1J shows the relative expression levels of embryonic stem cell-specific miR-302/367 family in hDF, H9-NSC, hDF-iNSC (SOX2), and hESC, measured via quantitative real time PCR.

FIG. 1K shows the relative expression levels of let-7/miR-98 family in hDF, H9-NSC, and hDF-iNSC (SOX2), measured via quantitative real time PCR.

FIG. 1L shows the PAX6- and NESTIN-positive colony forming efficiencies of miR-124-3p, miR-9-5p, miR-9-3p, anti-let-7b, and let-7b, measured after their transfection into SOX2-transduced hDFs.

FIG. 2A shows the results of MTT cell proliferation assay performed in hDF control group, SOX2-, SOX2/CMYC-, SOX2/LIN28-, and SOX2/HMGA2-transduced hDF groups.

FIG. 2B shows the colony-forming time measured in SOX2-, SOX2/CMYC-, SOX2/LIN28-, and SOX2/HMGA2-transduced hDF groups.

FIG. 2C shows the PAX6- and NESTIN-positive colony forming efficiency measured in SOX2-, SOX2/CMYC-, SOX2/LIN28-, and SOX2/HMGA2-transduced hDF groups.

FIG. 2D shows the results of flow cytometry analysis of hDF control group, SOX2-, SOX2/CMYC-, SOX2/LIN28-, and SOX2/HMGA2-transduced hDF groups, performed 7 days after virus transduction using the NSC cell surface marker (CD44) and positive marker (CD184) thereof.

Figure 31:
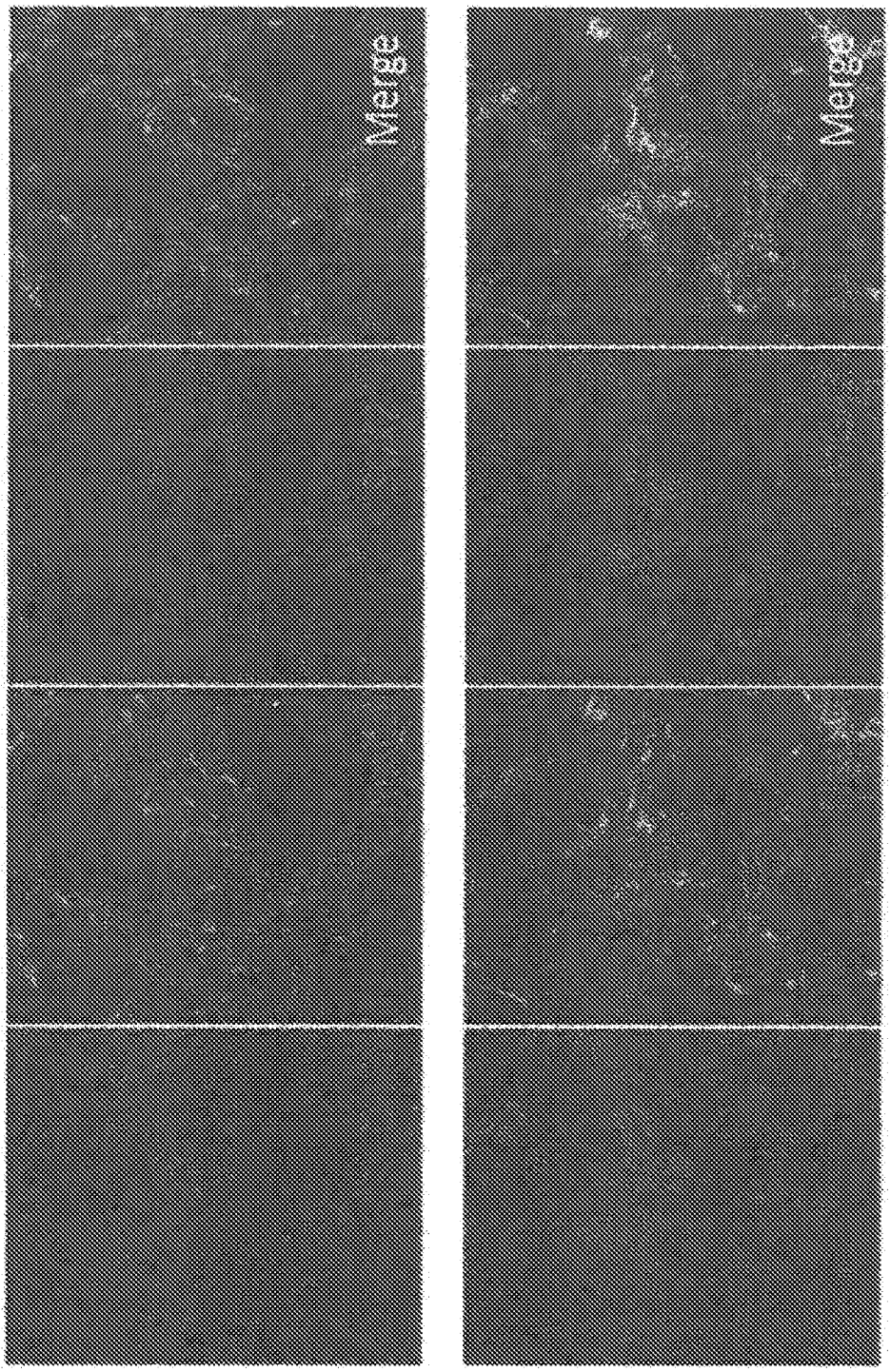

FIG. 2E shows the morphology of hDF-iNSCs (SOX2/HMGA2) and the results of the immunocytochemical analysis of the expressions of PAX6, NESTIN, Ki67, and HMGA2, observed under a bright-field microscope.

FIG. 2F shows the results of quantitative real time PCR of the expression of NSC-specific miRNA in H9-NSC, hDF-iNSC (SOX2), and hDF-iNSC (SOX2/HMGA2), compared to the expression level of hDF.

FIG. 2G shows the analysis results of methylation patterns of SOX2 gene promoters by bisulfide treatment of DNA derived from hDF, H9-NSC, hDF-iNSC (SOX2), and hDF-iNSC (SOX2/HMGA2).

FIG. 3A shows the immunocytochemical analysis of hDF-iNSC (SOX2/HMGA2) after their differentiation into three major cell types, i.e., neurons ($\alpha$-internexin, TH, DCX, ChAT, NF, MAP2, and TUJ1), astrocytes (GFAP), and oligodendrocytes (OLIG2 and O4).

FIG. 3B shows the sodium current and the action potential of the neurons derived from human induced neural stem cells (hiNSCs), recorded by voltage-clamp measurement.

FIG. 3C shows the sodium current and the action potential of the hiNSCs-derived neurons, after block of sodium current by lidocaine, recorded by voltage-clamp measurement.

FIG. 3D shows the sodium current and the action potential of the hiNSCs-derived neurons, after recovery of sodium current by washout, recorded by voltage-clamp measurement.

FIG. 3E shows that, after the transplantation of CM-DiI labeled hiNSCs into the hippocampal gyms region of a 4-week-old mouse, the hiNSCs were differentiated into neurons (TUJ1), astrocytes (GFAP), and oligodendrocytes (MBP), and were co-localized with CM-DiI.

FIG. 4A shows the procedure of producing iNCS from mesenchymal stem cells derived from human umbilical cord blood using SOX2/HMGA2. FIG. 4A confirms that neurosphere-like colonies were formed 7 days after virus transduction and that hUCB-MSC-derived hiNSCs were immunostained with PAX6 (red), NESTIN (green), and DAPI (blue).

FIG. 4B shows the morphology of senescent hUCB-MSCs which were transduced with SOX2, SOX2/CMYC, SOX2/LIN28, and SOX2/HMGA2 (a 21 day pass). The senescent hUCB-MSCs were evaluated by $\beta$-galactosidase activity, and the initial iNSC cluster was produced by SOX2/HMGA2 transduction alone.

FIG. 4C shows the quantitated results of PAX6- and NESTIN-positive colonies in control group, the senescent hUCB-MSCs transduced with SOX2, SOX2/CMYC, SOX2/LIN28, and SOX2/HMGA2.

FIG. 4D shows a schematic diagram for an experiment illustrating the strategy for reprogramming hiNSCs from hUCB-derived CD34$^+$ cells.

FIG. 4E shows the purity of CD34$^+$ cells by flow cytometry analysis via dot plot. The CD34$^+$ cells isolated from mononuclear cells were shown to have a purity of 84.15%.

FIG. 4F shows the images illustrating the characteristics of hUCB-CD34$^+$ iNSCs by immunochemical assay, wherein the cells were stained with NSC-specific markers (PAX6, NESTIN, and SOX2), a neuron marker (NF), and an astrocyte marker (GFAP).

FIG. 5 shows the images of H9-NSCs immunostained with PAX6, NESTIN, SOX2, Ki67, and HMGA2, observed under a microscope.

FIG. 6A shows the hDF-iNSCs (SOX2) transfected with miR-CTL, or 50 nM or 100 nM of let-7b, which were immunostained with BrdU-specific antibodies (green) and DAPI (blue) after the treatment with BrdU for 2.5 hours.

FIG. 6B shows the quantitated results of BrdU-positive cells in hDF-iNSCs (SOX2), which were transfected with miR-CTL, or 50 nM or 100 nM of let-7b.

FIG. 6C shows the diameter of neurospheres of the cells transfected with miR-CTL, or 50 nM or 100 nM of let-7b.

FIG. 6D shows the absolute number of the cells transfected with miR-CTL, or 50 nM or 100 nM of let-7b.

FIG. 6E shows the rate of primary neurosphere of the cells transfected with miR-CTL, or 50 nM or 100 nM of let-7b.

FIG. 7A shows the results of flow cytometry analysis of a negative cell surface marker (CD44) and a positive cell surface marker (CD184) in hDF-iNSC (SOX2), hDF-iNSC (SOX2/HMGA2), and H9-NSC.

FIG. 7B shows the heat maps of global genomes for hDF, H9-NSC, hDF-iNSC (SOX2), and hDF-iNSC (SOX2/HMGA2).

FIG. 7C shows the dot plots for comparing between hDF-iNSC (SOX2/HMGA2) and hDF; and between hDF-iNSC (SOX2/HMGA2) and H9-NSC.

FIG. 8A shows the results of hDF-iNSCs (SOX2) transfected with siCTL or 50 nM siHMGA2, which were immunostained with BrdU-specific antibodies (green) and DAPI (blue) after the treatment with BrdU for 2.5 hours.

FIG. 8B shows the quantitated results of BrdU-positive cells in hDF-iNSCs (SOX2), which were transfected with siCTL or 50 nM siHMGA2.

FIG. 8C shows the diameter of neurospheres of the cells transfected with siCTL or 50 nM siHMGA2.

FIG. 8D shows the absolute number of the cells transfected with siCTL or 50 nM siHMGA2.

FIG. 8E shows the rate of primary neurosphere of the cells transfected with siCTL or 50 nM siHMGA2.

FIG. 9A shows the immunocytochemical analysis of H9-NSCs after their differentiation into three major cell types, i.e., neurons (ChAT, NF, and MAP2), astrocytes (GFAP), and oligodendrocytes (O4).

FIG. 9B shows the sodium current and the action potential of the neurons derived from hiNSC, recorded by voltage-clamp measurement.

FIG. 9C shows the sodium current and the action potential of the neurons derived from hiNSC, after block of sodium current by lidocaine (0.1%), recorded by voltage-clamp measurement.

FIG. 9D shows the sodium current and the action potential of the neurons derived from hiNSC, after recovery of sodium current by washout, recorded by voltage-clamp measurement.

FIG. 9E shows the immunohistochemical results of transplanted CM-DiI-labeled hiNSCs.

FIG. 10A shows the results of flow cytometry analysis of hMSC surface markers (negative markers: CD34, CD45, and HLA-DR; positive markers: CD73 and CD105) and a positive cell surface marker (CD184) in hMSCs and hMSC derived iNSCs.

FIG. 10B shows the results of Western blot analysis regarding the expression levels in three different lines of HMGA2 and hUCB-MSC, respectively.

FIG. 10C shows the PAX6- and NESTIN-positive colony forming efficiencies, measured after the transduction of SOX2 or SOX2/HMGA2 in hUCB-MSCs.

FIG. 10D shows the proliferation rates of H9-NSC, hDF-iNSC, and hMSC-iNSC determined by cumulative population doubling level (CPDL) analysis.

FIG. 10E shows the PAX6- and NESTIN-positive colony forming efficiencies, measured in hUCB-CD34$^+$ cells transduced with SOX2 or SOX2/HMGA2.

FIG. 11 shows the results of confirming the differentiation potential of human umbilical cord blood-derived stromal cells (hUCBSCs).

FIG. 12 shows the measurement results of the transduction efficiency of hUCBSCs into HMGA2.

FIG. 13 shows the results of expression level of HMGA2 in early stages of HMGA2-transduced hUCBSCs for generations of 8 or less, measured by immunocytochemical analysis.

FIG. 14 shows the results of expression level of HMGA2 in early stages of HMGA2-transduced hUCBSCs for generations of 8 or less, measured by microarray.

FIG. 15 shows the results of expression level of HMGA2 according to the progress of generations in HMGA2-transduced hUCBSCs, measured by PCR.

FIG. 16 shows the measurement results of cell morphology according to the progress of generations in HMGA2-transduced hUCBSCs, measured by phase contrast image.

FIG. 17 shows results of expression level of senescence associated beta-galactosidase (SA-β-gal) according to the progress of generations in HMGA2-transduced hUCBSCs, measured by β-gal staining.

FIG. 18 shows the results of cell proliferation according to the progress of generations in HMGA2-transduced hUCBSCs, measured by MTT assay.

FIG. 19 shows the results of expression levels of genes associated with HMGA2 overexpression-related signal pathway and genes associated with molecular cellular functions in HMGA2-transduced hUCBSCs, measured by Ingenuity Pathway Analysis (IPA) software.

FIG. 20 shows the results of Western blot analysis for evaluation of the effect of HMGA2 overexpression on PI3K/AKT pathway and mTOR/p70s6K in HMGA2-transduced hUCBSCs.

FIG. 21 shows the results of cell morphology according to the progress of generations in HMGA2-transduced hUCBSCs measured by phase contrast image, and the results of expression level of senescence associated beta-galactosidase (SA-β-gal) according to the progress of generations for evaluation of the level of senescence of HMGA2-inhibited hUCBSCs measured by β-gal staining.

FIG. 22 shows the results of cell proliferation in HMGA2-inhibited hUCBSCs, measured by MTT assay.

FIG. 23 shows the results of Western blot analysis for evaluation of the effect of HMGA2 inhibition on PI3K/AKT pathway and mTOR/p70s6K in HMGA2-transduced hUCBSCs.

FIG. 24 shows the measurement results of differentiation potential of HMGA2-inhibited hUCBSCs into fat tissues.

FIG. 25 shows the comparison results between the gene expression of HMGA2-overexpressing hUCBSCs and the gene expression of HMGA2-inhibited hUCBSCs.

FIG. 26 shows the results of PCR performed on 8 genes, which were selected by comparison of the gene expression of HMGA2-overexpressing hUCBSCs and the gene expression of HMGA2-inhibited hUCBSCs.

FIG. 27 shows the results of PCR performed on the selected genes, whose expressions are increased when HMGA2 is overexpressed and decreased when HMGA2 is inhibited in hUCBSCs, and on those genes whose expressions are decreased when HMGA2 is overexpressed and increased when HMGA2 is inhibited in hUCBSCs.

FIG. 28 shows the results of flow cytometry analysis of CD34$^+$ cells isolated from umbilical cord blood-derived mononuclear cells.

FIG. 29 shows the fluctuation in the number of CD34$^+$ cells according to days of culture in a CD34$^+$-specific medium.

FIG. 30 shows the progress of morphological change from CD34$^+$ cells to induced neural stem cells.

FIG. 31 shows the expression features of CD34$^+$ iNSCs immunostained with DAPI, NESTIN, HMGA2, and SOX2.

DETAILED DESCRIPTION OF THE PREFERRED EMBODIMENTS

In one aspect, the present invention provides a kit for inducing reprogramming of a non-neuronal cell into a neural stem cell (NSC), including (a) an SRY (sex determining region Y)-box 2 (SOX2) protein or a nucleic acid molecule encoding the SOX2 protein; and (b) a high mobility group at-hook 2 (HMGA2) protein or a nucleic acid molecule encoding the HMGA2 protein.

The present invention relates to producing induced neural stem cells from target cells by increasing the expression of two factors of SOX2 and HMGA2, the conventionally well-known neuronal differentiation transcription factors, within the target cells such as non-neuronal cells, etc. The method of producing induced neural stem cells of the present invention can prepare the induced neural stem cells from non-neuronal cells by simply using two inducing factors of SOX2 and HMGA2, and thus can prepare the induced neural stem cells in a more efficient manner than the conventional methods which use four or five inducing factors. Additionally, the method of the present invention can significantly reduce the time required for reprogramming and provide significantly higher reprogramming-inducing efficiency and proliferation capacity than when only a single SOX2 gene is used, thus increasing its potency to be used for therapeutic purposes.

SOX2 proteins are proteins expressed by sex determining region Y-box2 (Sox2) genes, and are known to be expressed on the central nervous system at prenatal stage and involved in self-replication of neural stem cells, but are also known to be frequently expressed in malignant glioma.

High-mobility group at-hook 2 (HMGA2) proteins are known to serve as a factor to modify chromatin structures by binding to DNA, and as a result, can induce a change in gene transcription.

In the present invention, SOX2 proteins and HMGA2 proteins or nucleic acid molecules encoding these proteins may include all SOX2 and HMGA2 derived from animals including humans, mice, etc., and preferably the SOX2 and HMGA2 derived from humans. Additionally, the SOX2 and HMGA2 proteins of the present invention may not only include those proteins having wild type amino acid sequences of these proteins but also their variants. Herein, the variants of the SOX2 and HMGA2 proteins include proteins having sequences different from the natural amino acid sequences of SOX2 and HMGA2, due to deletion, insertion, conservative or non-conservative substitution, or a combination thereof in at least one amino acid residue. The variants may be functional equivalents which exhibit the same biological activities to those of natural proteins, or those where the physicochemical properties of the proteins are modified by necessity with improved structural stability or physiological activities to the physicochemical environments.

As used herein, the term "a nucleic acid molecule encoding SOX2 or HMGA2 protein" refers to a nucleotide sequence encoding the wild type of the SOX2 or HMGA2 protein, or the variant type of the SOX2 or HMGA2 protein as described above, wherein at least one nucleotide may be modified by substitution, deletion, insertion, or a combination thereof, and may be prepared by isolation from natural sources or by chemical synthesis.

The nucleic acid molecule encoding the SOX2 protein or the nucleic acid molecule encoding the HMGA2 proteins may be in a shape where each of the nucleic acid molecules is independently included in an expression vector.

Specifically, the SOX2 protein or the HMGA2 protein may be a protein in the form expressed in vitro from a cell line using an expression vector including the nucleic acid molecules encoding these proteins. As for the expression vector, a baculovirus expression vector, a mammalian expression vector, or a bacterial an expression vector may be used and, as for the cell line, an insect cell line, a mammalian cell line, or a bacterial cell line may be used, but the expression vector and the cell line to be used in the present invention are not limited thereto.

As used herein, the term "an expression vector" may refer to a gene construct including essential regulatory elements, in which a gene insert is operably connected thereto to be expressed, capable of expressing a target protein. The expression vector of the present invention may be used for the purpose of delivering reprogramming-inducing factors to non-neuronal cells. The expression vector of the present invention may not only include expression regulatory elements such as a promoter, an operator, an initiation codon, a termination codon, a polyadenylation signal, and an enhancer, but may also selectively include a signal sequence for membrane targeting or secretion, or a leader sequence, and may be prepared variously according to the intended uses. The promoter of the vector may be constitutional or inducible. Additionally, the expression vector includes a selective marker for selecting a host cell including a vector, and when the expression vector is a replicable expression vector, it includes the origin of replication. The expression vector may self-replicate or may be integrated into the host DNA. The vector may include a plasmid vector, a cosmid vector, an episome vector, a virus vector, etc., and preferably, a virus vector. The virus vector may include vectors derived from retroviruses such as human immunodeficiency virus (HIV), murine leukemia virus (MLV), avian sarcoma/leukosis (ASLV), spleen necrosis virus (SNV), rous sarcoma virus (RSV), mouse mammary tumor virus (MMTV), adenovirus, adeno-associated virus, herpes simplex virus, Sendai virus, etc., but is not limited thereto.

The nucleic acid molecules encoding the SOX2 or HMGA2 protein may be a messenger RNA (mRNA).

As used herein, the term "reprogramming" refers to a process which restores or converts differentiated cells present in a state of various features, for example, cells without differentiation potential or cells with partial differentiation potential, etc., to those with a new type of differentiation potential. The reprogramming mechanism of the cells refers to the establishment of a different set of epigenetic marks after deletion of an epigenetic mark within a nucleus (a state of DNA related to causing a genetic change in functions without a change in a given nucleotide sequence), and different cells and tissues obtain different gene expression programs during the differentiation and growth of a multicellular organism. These different gene expression patterns appear to be substantially controlled by epigenetic modifications, e.g., DNA methylation, histone modification, and other chromatin-binding proteins. Accordingly, the cell types in a multicellular organism are fixed and do not change once the cells are differentiated or escape from cell cycle, but, for a particular period during normal development or during the progress of a particular disease, major epigenetic reprogramming may proceed. The present invention provides a method for preparing cells having the potency of undifferentiated cells by treating the already differentiated subject cells with a particular protein.

As used herein, the term "a reprogramming-inducing factor" refers to a material which can induce a finally differentiated cell or partially differentiated cell to be reprogrammed into an induced neural stem cell having the potential to be differentiated into new cell types, and may include SOX2 proteins, HMGA2 proteins, or nucleic acid molecules encoding these proteins. The reprogramming-inducing factor may include any material capable of inducing reprogramming of differentiated cells without limitation.

As used herein, the HMGA2 proteins or the nucleic acid molecules encoding these proteins may be chromatin modulators. In particular, chromatin is a nucleosome having a basic structure of a complex between DNA and a histone protein. Chromatin modulation is performed such that the expression feature of a corresponding gene changes as the way that DNA surrounds the histone changes by, for example, acetylation of histone, DNA methylation, etc. Accordingly, chromatin can be modulated via methylation/demethylation of DNA, and HMGA2 may act as a chromatin modulator by promoting low methylation on the promoter region of SOX2 gene (Example 4-5).

As used herein, "a non-neuronal cell" refers to all differentiated or undifferentiated cells, other than neuronal cells, that serve as a target cell of the present invention. The non-neuronal cell may be cells derived from various animals including humans, monkeys, pigs, horses, cattle, sheep, dogs, cats, mice, rabbits, etc., and preferably, the cells derived from humans, but the cells to be reprogrammed by the induced neural stem cells are not limited thereto.

The non-neuronal cell may be a somatic cell, an adult stem cell, or a pluripotent stem cell.

As used herein, the term "a somatic cell" refers to cells which constitute an adult having limited differentiation potential and self-renewal capacity, specifically, somatic cells constituting skins, hairs, fats, blood, etc., of humans, and preferably human fibroblasts or human umbilical cord blood cell, but is not limited thereto.

As used herein, "an adult stem cell" refers to stem cells present in bones, fats, bone marrow stroma, muscles, nerves, etc., and preferably mesenchymal stem cells, but is not limited thereto.

As used herein, "an induced neural stem cell" refers to cells prepared in such a manner as in establishing undifferentiated stem cells having pluripotency, which is similar to or the same as that of neural stem cells, by applying the reprogramming technology on differentiated cells. The induced neural stem cell has characteristics the same as or similar to those of the neural stem cell, specifically, has a similar cell morphology, similar gene and protein expression patterns, and can have pluripotency both in vivo and in vitro. Accordingly, the induced neural stem cell of the present invention may be one that can be differentiated into a nerve cell (neuron), an astrocyte, an oligodendrocyte, a GABAergic neuronal cell, a dopaminergic neuronal cell, etc.

The kit of the present invention may not be particularly limited, but any type of kit that can be conventionally used in the art may be used.

The kit of the present invention may be packaged in a form in which a first composition including SOX2 proteins and nucleic acid molecules encoding the SOX2 proteins, and a second composition including HMGA2 proteins and nucleic acid molecules encoding the HMGA2 proteins, are contained in a separate container, respectively, or in a single container which is partitioned into more than one section.

In an exemplary embodiment of the present invention, in order to confirm the effects of SOX2 and HMGA2 proteins during the reprogramming-inducing process from human fibroblasts to induced neural stem cells, these proteins were overexpressed, and their morphological changes and reprogramming-inducing efficiency by PAX6/NESTIN-positive colony analysis were continuously examined. As a result, it was confirmed that when the expressions of both SOX2 and HMGA2 were increased simultaneously, the self-renewal capacity, proliferation capacity, and differentiation potential into neuronal cells as well as the reprogramming-inducing efficiency were increased, compared to when only the SOX2 expression alone was increased. In particular, when the reprogramming was induced along with HMGA2, the colonies of induced neural stem cells were formed about 10 days earlier.

Additionally, it was confirmed that SOX2 and HMGA2 can contribute to the effective reprogramming of umbilical cord blood-derived mesenchymal stem cells (hUCB-MSCs) and umbilical cord blood-derived blood cells into induced neural stem cells, and in particular, it was confirmed that HMGA2 can contribute to the improvement of reprogramming efficiency and reduce the time required for reprogramming.

As a non-neuronal cell used in the present invention, umbilical cord blood-derived mesenchymal stem cells are a representative example of adult stem cells, and umbilical cord blood-derived blood cells are a representative example of somatic cells, and these results suggest that, with the aid of SOX2 and HMGA2 as reprogramming-inducing factors, not only somatic cells but also adult stem cells can be effectively reprogrammed by induced neural stem cells.

In another aspect, the present invention provides a method of preparing induced neural stem cells reprogrammed from non-neuronal cells, or neuronal cells differentiated therefrom. Specifically, the method of the present invention may include (a) delivering to a non-neuronal cell a SOX2 protein or a nucleic acid molecule encoding the SOX2 protein, and an HMGA2 protein or a nucleic acid molecule encoding the HMGA2 protein, or increasing the expression of the SOX2 protein and the HMGA2 protein in a non-neuronal cell; and (b) culturing the cells in step (a).

Preferably, the method of the present invention may further include step (c) of separating neural stem cell-like colonies from the cell culture obtained in step (b).

In the method of producing the induced neural stem cells according to the present invention, the expression of SOX2 and HMGA2 in target cells may be increased by introducing expression regulatory elements of SOX2 and/or HMGA2 into the target cells Specifically, the method of delivering reprogramming-inducing factors, such as the SOX2 protein or the nucleic acid molecule encoding the SOX2 protein, and the HMGA2 protein or the nucleic acid molecule encoding the HMGA2 protein, to cells may be performed by the conventional methods for providing nucleic acid molecules or proteins used in the art without limitation, and preferably, a method of adding the reprogramming-inducing factors to a culture medium for non-neuronal cells, or directly injecting the reprogramming-inducing factors into the non-neuronal cells, wherein the reprogramming-inducing factors used herein may be used in the form of viruses, which were obtained from packaging cells transfected with a viral vector, into which the corresponding genes, i.e., the nucleic acid molecules encoding SOX2 proteins and the nucleic acid molecules encoding HMGA2 proteins, were respectively inserted; mRNAs, which were produced by in vitro transcription; or proteins, which were produced in various cell lines.

The method of directly injecting the reprogramming-inducing factors into the differentiated cells may be performed by any method known in the art, but is not limited thereto, and may be performed by appropriately selecting a method from microinjection, electroporation, particle bombardment, direct injection into muscles, and methods using insulators and transposons.

The viral vector to be used may be a vector derived from retrovirus, lentivirus, adenovirus, adeno-associated virus, herpes simplex virus, sendai virus, etc., but is not limited thereto, and preferably, a retroviral vector may be used. Additionally, for the packaging cells, various cells known in the art may be used after selecting according to the viral vectors being used.

Additionally, the expression of SOX2 and HMGA2 within the target cells may be increased by introducing expression regulatory factors of SOX2 and/or HMGA2.

Specifically, the expression regulatory factor of HMGA2 may be a let-7 miRNA cluster inhibitor or a PDE4D inhibitor. The let-7 miRNA cluster is known to be an miRNA that targets HMGA2, thereby reducing its expression. In the present invention, it is possible to increase the amount of HMGA2 expression within the target cells by introducing the let-7 miRNA cluster inhibitor.

Additionally, the expression regulatory factor of SOX2 may be a PDE4D inhibitor. The primary cellular mechanism of cAMP activation is known to be cAMP decomposition by an isoenzyme series called cyclic nucleotide phosphodiesterase (PDE). PDE enzymes include 12 known enzymes. The inhibition of PDE type IV (PDE4) has been acknowledged to be especially effective in both the inhibition of inflammation-mediated release and the relaxation of airway smooth muscle. The cAMP activation was suggested as a promising strategy for inducing neuronal cells to overcome inhibitory signals, after SCI. The inhibition of cAMP hydrolysis by rolipram, which is a PDE4 inhibitor, is known to prevent the reduction of cAMP level after spinal cord contusion. Accordingly, when the PDE4 inhibitor binds to a Schwann cell graft, it promotes considerable conservation of spinal cord and proprioception axon, and formation of myelin sheath. It is possible to use Se1CID™ as an inhibitor of PDE IV activity.

Accordingly, the use of the phosphodiesterase 4D (PDE4D) inhibitor, which is a common expression regulatory factor for both SOX2 and HMGA2, can increase the expression amount of both SOX2 and HMGA2, thereby significantly increasing the reprogramming-inducing efficiency, etc.

The reprogramming-inducing factors may include at least one protein selected from the group consisting of OCT4, KlF4, CMYC, LIN28, and Nanog, or at least one nucleic acid molecule encoding these proteins, in addition to the reprogramming-inducing factors of SOX2 and HMGA2 of the present invention. These proteins are known reprogramming-inducing factors, and among them, CMYC and LIN28 belong to the let-7 miRNA cluster. Therefore, reprogramming-inducing efficiency can be increased by additionally expressing these inducing factors.

Additionally, in the present invention, other nanoparticles or compounds may be used to introduce the SOX2 proteins or nucleic acid molecules encoding the SOX2 proteins, and HMGA2 proteins or nucleic acid molecules encoding the HMGA2 proteins.

The culturing of the cells in step (b) of the present invention may be performed in an appropriate culture medium and culture conditions known in the art. These culturing processes may be easily adjusted by a skilled person in the art according to the cells being selected.

Step (b) includes culturing in a medium for neuronal cell differentiation, and neuronal cells can be formed from the induced neural stem cells.

In another aspect, the present invention provides induced neural stem cells prepared by the method described above or the neuronal cells differentiated therefrom.

The induced neural stem cells are the same as described above.

As confirmed in Examples, the induced neural stem cells can be differentiated into neurons, astrocytes, and oligodendrocytes, and also the neuronal cells differentiated from the induced neural stem cells can be obtained.

In another aspect, the present invention provides a cell therapy product for neuronal cell regeneration, including the induced neural stem cells or the neuronal cells differentiated from the induced neural stem cells, as an active ingredient.

The induced neural stem cells of the present invention are those which can be differentiated into neuron-associated cells, and are thus useful for regeneration of neuronal cells. Accordingly, they may be used as a cell therapy product.

The cell therapy product of the present invention may include from $1.0 \times 10^5$ cells to $1.0 \times 10^9$ cells per 1 mL, preferably from $1.0 \times 10^6$ cells to $1.0 \times 10^8$ cells per 1 mL, and more preferably $1.0 \times 10^7$ cells per 1 mL, but is not limited thereto.

The cell therapy product of the present invention may be used without freeze-drying or freeze-dried for later use. When the freeze-drying is necessary standard cryopreservative (e.g., DMSO, glycerol, and Epilife™ cell freeze-drying medium (Cascade Biologics)) may be added to a cell population before freeze-drying.

Additionally, the cell therapy product may be administered after being formulated into a unit administration form suitable for administration into a patient's body according to the conventional method in the pharmaceutical field, and the formulation may include an administration dose which will be effective after a single or a few administrations. Examples of the formulations suitable for this purpose, as a formulation for parenteral administration, may preferably be injections such as injection ampoules, infusion agents such as infusion bags, and spraying agents such as aerosol formulations, etc. The injection ampoules may be prepared by mixing with an injection immediately prior to use. For injection solutions, physiological saline, glucose, mannitol, Ringer's solution, etc., may be used. Additionally, for infusion bags, materials of polyvinyl chloride or polyethylene may be used, and infusion bags manufactured by Baxter, Becton Dickinson, Medcep, National Hospital Products, and Terumo.

The cell therapy product may further include at least one pharmaceutically acceptable carrier, e.g., a preserving agent, an analgesic, a solubilizer, a stabilizer, etc., for injection formulations; and a base, an excipient, a lubricant, a preserving agent, etc., for topical formulations.

The thus-prepared cell therapy product of the present invention may be administered by the conventional administration method used in the art along with other stem cells, which are used for transplantation and other uses, or in a mixed form with these stem cells, and may be preferably engrafted or transplanted directly to the disease area, or directly transplanted or infused to the abdominal cavity of a patient in need of treatment, but is not limited thereto. Additionally, the administration may be administered either by a non-surgical administration method using a catheter or by a surgical administration method by injecting into the disease area after cutting it off or transplanting to the disease area, but it is more preferable to administer by a non-surgical administration method using a catheter. Additionally, a parenteral administration according to the conventional method, for example, direct administration into the lesions, and also a transplantation by infusion into the blood vessel, which is a general method for hemopoietic stem cell transplantation, are possible.

The daily dose of the cells described above may be administered once or as a few divided doses daily in the amount of from $1.0 \times 10^4$ cells/kg to $1.0 \times 10^{10}$ cells/kg body weight, and preferably $1.0 \times 10^5$ cells/kg to $1.0 \times 10^9$ cells/kg body weight. However, it should be understood that the actual dose of active ingredients is determined considering various related factors such as disease to be treated, severity of illness, administration route, body weight, age, and gender of a patient, etc., and thus the dose should not be construed as limiting the scope of the present invention in any manner.

In another aspect, the present invention provides a method for inhibiting or recovering neuronal cell damage of a subject including administering the reprogrammed induced neural stem cells or the neuronal cells differentiated therefrom. Specifically, the neuronal cell damage of a subject may be inhibited or recovered by administering the induced neural stem cells, which were reprogrammed by delivering, to non-neuronal cells, the SOX2 protein or the nucleic acid molecule encoding the SOX2 protein, and the HMGA2 protein or the nucleic acid molecule encoding the HMGA2 protein; and culturing the cells, or the neuronal cells differentiated therefrom.

As used herein, the term "a subject" refers to cattle, dogs, pigs, chickens, sheep, horses, and mammals including humans, but is not limited thereto. Preferably, the administration of the reprogrammed induced neural stem cells or the culture product thereof may be intraperitoneal or intravascular administration, direct administration into the lesions or administration into the synovial cavity of a joint, etc.

The inhibition or recovery of the neuronal cell damage may include the prevention or treatment of neuronal cell damage-associated diseases.

In another aspect, the present invention provides a pharmaceutical composition for preventing or treating neuronal cell damage-associated diseases, including the SRY (sex determining region Y)-box 2 (SOX2) protein or the nucleic acid molecule encoding the SOX2 protein, and the high mobility group at-hook 2 (HMGA2) protein or the nucleic acid molecule encoding the HMGA2 protein, as active ingredients.

As explained above, the composition, which includes the SOX2 protein or the nucleic acid molecule encoding the SOX2 protein and the HMGA2 protein or the nucleic acid molecule encoding the HMGA2 protein, may be introduced into a non-neuronal cell to induce its reprogramming into a neural stem cell, and is thereby used for the prevention or treatment of neuronal cell damage-associated diseases.

Additionally, the SOX2 and/or HMGA2 gene(s) may be provided in the form where an intracellular gene delivery system or gene transporter known in the art, for example, lipoplex, polyplex, cell permeable peptide (CPP), protein transduction domain (PTD), etc., but are not limited thereto.

The PTD may be used without limitation as long as it can improve the efficiency of intracellular introduction of the SOX2 and/or the HMGA2.

Additionally, the SOX2 and/or the HMGA2 may be in the form of a fusion protein, which is encoded by a conjugate between a SOX2 and/or HMGA2 plasmid and a transporter to deliver the plasmid into a cell. For example, it may be in the form of a fusion protein between the SOX2 and/or HMGA2 and CPP or PTD, or between the SOX2 and/or HMGA2 and a low molecular weight protamine conjugate.

As used herein, the term "neuronal cell damage-associated diseases" refers to diseases that may occur due to modification, loss, etc., of neuronal cells, including Parkinson's disease, Alzheimer's disease, Pick's disease, Huntington's disease, amyotrophic lateral sclerosis, ischemic encephalopathy such as stroke, demyelinating disease, multiple sclerosis, epilepsy, degenerative neuronal diseases, spinal cord injury, etc., but is not limited thereto.

As used herein, the term "prevention" refers to all kinds of actions associated with the inhibition or delay of the neuronal cell damage-associated diseases by administering the above composition, and the term "treatment" refers to all kinds of actions associated with the improvement or advantageous changes in symptoms of the neuronal cell damage-associated diseases by administering the above composition.

In another aspect, the present invention provides a method of screening a regeneration promoter or a regeneration inhibitor for a neural stem cell or neuronal cell, including 1) preparing an isolated non-neuronal cell; 2) inducing the production of an induced neural stem cell by delivering, to a non-neuronal cell, a SOX2 protein or a nucleic acid molecule encoding the SOX2 protein; and an HMGA2 protein or a nucleic acid molecule encoding the HMGA2 protein, or increasing the expression of the SOX2 protein and the HMGA2 protein in a non-neuronal cell; 3) optionally, differentiating the induced neural stem cell produced in step 2) into a neuronal cell; and 4) treating with the candidate material after step 1 or step 2, and determining whether or not the induced neural stem cell or the neuronal cell is produced, or the production level thereof, depending on the treatment of a candidate material.

In the present invention, the presence of production or the production level of neural stem cells or neuronal cells by reprogramming of non-neuronal cells may be evaluated by observing the changes such as the morphological change in non-neuronal cells, presence of expression of neuronal cell-specific markers, self-renewal capacity, proliferation capacity, differentiation potential into neuronal cells, etc., before and after treatment with a candidate material.

Additionally, the present invention may further include a step of determining the candidate material as a regeneration promoter for neural stem cells or neuronal cells, if the production level of the induced neural stem cells or the neuronal cells is increased in step 4.

Preferably, the screening method may be to screen a patient-customized regeneration promoter or a patient-customized regeneration inhibitor for a neural stem cell or neuronal cell using a non-neuronal cell isolated from a patient.

Specifically, a method for treatment may be provided by determining a regeneration promoter or regeneration inhibitor for neuronal cells suitable for the constitution or environment of an individual patient based on individual investigation. Accordingly, a customized therapeutic agent may be selected by selecting a candidate drug as the regeneration promoter or regeneration inhibitor for neuronal cells, according to the screening method, treating the drug on the patients with the neuronal cell damage-associated diseases, and confirming the therapeutic effects followed by mapping and storing the same. That is, by combining both the in vitro screening method and the in vivo confirmation method, customized therapeutic agents for neuronal cell damage-associated patients can be more effectively selected and confirmed.

In an exemplary embodiment of the present invention, it was confirmed by the above screening method that the induction efficiency into the induced neural stem cells was increased by about two fold or higher when HMGA2 gene was additionally introduced, compared to when SOX2 gene or the like was introduced, and thus it was confirmed that HMGA2 proteins can be used as a regeneration promoter for neuronal cells.

In another aspect, the present invention provides a method of screening a personal customized therapeutic agent for a neuronal cell including: 1) preparing an isolated non-neuronal cell; 2) inducing the production of an induced neural stem cell by delivering, to a non-neuronal cell, a SOX2 protein or a nucleic acid molecule encoding the SOX2 protein; and an HMGA2 protein or a nucleic acid molecule encoding the HMGA2 protein, or increasing the expression of the SOX2 protein and the HMGA2 protein in a non-neuronal cell; 3) differentiating the induced neural stem cell produced in step 2) into a neuronal cell; and 4) treating the non-neuronal cell formed in step 3 with the candidate material, and determining whether or not the candidate material is the therapeutic agent for a neuronal cellcustomized to a subject from which the non-neuronal cell is derived or not.

Specifically, in order to select a personal customized neuronal cell therapy product according to the constitution or environment of an individual patient, it can be confirmed and verified whether the non-neuronal cells used for producing the induced neural stem cells can be used as a customized neuronal cell therapy product for a subject from which the non-neuronal cells were derived, by confirming the changes in neuron regeneration-related mechanism and in expression of proteins related thereof, by treating the neural stem cells induced in step 2 or the neuronal cells formed in step 3 with the candidate material.

In another aspect, the present invention provides a composition for promoting reprogramming of a non-neuronal cell into an induced neural stem cell (iNSC) including an HMGA2 protein or a nucleic acid encoding the HMGA2 protein as an active ingredient.

In an exemplary technical feature of the present invention, it was confirmed that the induction efficiency from non-neuronal cells to induced neural stem cells and proliferation capacity were significantly higher when the expression of the HMGA2 protein was increased along with the SOX2 factor, which is conventionally well known as a transcription factor for neuron differentiation, than in reprogramming using the conventional SOX2. Accordingly, the HMGA2 proteins and nucleic acid molecules encoding the same can be used for promoting reprogramming non-neuronal cells into neural stem cells.

In another aspect, the present invention provides a composition for cell proliferation or a composition for inhibiting cellular senescence containing an HMGA2 protein or a nucleic acid encoding the HMGA2 protein as an active ingredient As used herein, the term "cell proliferation" includes the increase of cell number, and accordingly, the cell proliferation accompanies DNA replication, cell division, and increase of various cellular components, and the rate of cell proliferation can be controlled in vivo.

Additionally, the term "cellular senescence" refers to a process including degeneration of characteristics and functions of a cell until the time of cell death or termination of cell proliferation. The known reasons of senescence include inhibition of metabolism by metabolites, change in cell surface, increase of crosslinking between cytoskeleton molecules such as collagen, accumulation of degraded molecules by free radicals in cells, accumulation of errors in transcription and translation of genetic information, life expectancy of cells genetically programmed by lethal genes, deterioration in intracellular DNA damage and repair activity, etc. As used herein, the term "senescence" not only includes cellular senescence but also aging of tissues and living organisms. In particular, the senescence of stem cells may accompany increase of the expression of senescence associated β-galactosidase in stem cells, increase of the size of stem cells, decrease of proliferation rate of stem cells, decrease of proliferation period, decrease of telomerase activity, or decrease of differentiation potential of stem cells, according to the increase of the number of subcultures.

In Examples 11 through 20 of the present invention, it was confirmed that HMGA2-transduced human umbilical cord blood-derived cells (hUCBSCs) not only showed a reduced change in morphology but also showed a decrease in SA-β-gal expression and maintenance of cell proliferation. In contrast, when HMGA2 was inhibited the change in morphology increased, and also cell proliferation was significantly decreased along with the increase of SA-f3-gal expression. Accordingly, it was confirmed that the overexpression of HMGA2 protein can promote proliferation of stromal cells while inhibiting senescence of the cells. Additionally, the controlling proliferation, maintenance, and senescence of stromal cells according to the present invention can be performed by controlling the proliferation of the stromal cells by inducing the expression of HMGA2 protein via transfection of the stromal cells, and maintaining differentiation potential and stem cell capability, thereby preventing senescence of stromal cells. Therefore, as the number of the subculture increases during culture, the senescence of stromal cells proceeds more rapidly, and thus the problem of rapid decrease in cell division can be solved. This method can be also applied to stem cells.

Hereinafter, the present invention will be described in more detail with reference to the following Examples. However, these Examples are for illustrative purposes only, and the invention is not intended to be limited by these Examples.

Preparation Example 1

Cell Culture (1) Human umbilical cord blood-derived mesenchymal stem cells (hUCB-MSC) were obtained from 20- to 30-year-old mothers immediately after full-term delivery, and only the blood samples collected within 24 hours from delivery were used. The umbilical cord blood samples were mixed with HetaSep solution (Stem Cell Technology, Vancouver, Canada) at a ratio of 5:1 (v/v), and then incubated at room temperature until the red blood cells were depleted. Upon incubation, the supernatant was collected and mononuclear cells were collected by a Ficoll (GE healthcare life sciences, Pittsburgh, Pa.) density-gradient centrifugation at 2,500 rpm for 20 minutes. The cells were washed twice with PBS and seeded on culture dishes with growth media of endothelial cell growth medium-2 (Gibco BRL, Grand Island, N.Y.) containing 10% fetal bovine serum (FBS; Gibco BRL). The isolation and research protocols were performed under the approval of the Boramae Hospital institutional Review Board (IRB) and the IRB of Seoul National University (1109/001-006).

(2) Meanwhile, human dermal fibroblasts (hDFs, C-013-5C) were purchased from Life Technologies and were cultured in fibroblast growth medium-2 (Gibco BRL) containing 10% FBS.

(3) H9-dervied human neural stem cells (H9-hNSCs, NA800-100) were purchased from Gibco and cultured in a KnockOut DMEM/F12 basal medium containing StemPro Neural Supplement, basic FGF, and EGF recombinant proteins.

(4) Human umbilical cord blood-derived stromal cells were isolated and cultured as described below. Specifically, in order to remove red blood cells from the umbilical cord blood (Seoul National University Hospital), the umbilical cord blood was mixed with HetaSep solution (Stem Cell Technology, Vancouver, Canada) at a ratio of 5:1 (v/v), and then incubated at room temperature for 30 minutes. The supernatant was carefully collected and mononuclear cells were collected by adding a Ficoll solution and centrifuged at 2,500 rpm for 20 minutes. Only the isolated cells were obtained, washed twice with PBS, and cultured in an EMEM (Gibco) medium containing heparin, ascorbic acid, recombinant human epidermal growth factor (rhEGF), hydrocortisone, vascular endothelial growth factor (VEGF), recombinant human fibroblast growth factor (rhFGF-B), recombinant long R insulin-like growth factor-1 (R3-IGF-1), gentamycin sulfate, amphotericin-B (GA-1000)), and 10% FBS (Gibco), at a concentration of $2 \times 10^5$ cells/cm$^2$. 4 days after the incubation, those cells which were not attached to the bottom were removed, and subcultures were performed when 80% of the cells had been confluent.

Preparation Example 2

Preparation of Human Induced Neural Stem Cells (hiNSCs) from Human Dermal Fibroblasts by Transduction SOX2, HMGA2, CMYC, and LIN28 plasmids were transfected into 293T cells with VSV-G and gag/pol plasmids and Fugene 6 transfection reagent (Roche, Indianapolis, Ind.). The viruses were collected after 48 hours and 72 hours post-transfection, and charged with 5 µg/mL Polybrene (Sigma, Ronkonkoma, N.Y.) to transduce the genes either singly or in a combination of at least two genes to hDFs, hUCB-MSCs, and hUCB-CD34$^+$ MNCs. After the transduction, the cells were washed twice with PBS to remove the viruses and were cultured in a growth medium for proliferation.

For neural stem cell induction, media were replaced with ReNcell NSC maintenance media (Millipore, Billerica, Mass.), which are neural stem cell induction media containing bFGF (Sigma) and EGF (Sigma). The hiNSCs were subcultured by Accutase (Gibco BRL).

Example 1

Isolation of iNSCs and Confirmation of their Characteristics

The hDFs were transfected into hiNSCs on a glass coverslip coated with poly-L-ornithine (PLO) and fibronectin (FN) with STO feeder cells using retroviral SOX2. SOX2- and NSC-like colonies were generated from the SOX2-transduced hDFs within 2 weeks to 3 weeks of the transfection.

The induced neural stem cell colonies were isolated, and stabilized by repeated subcultures and neurosphere culture. For the attachment of the induced neural stem cells, the glass coverslip was coated with PLO/FN, and $5\times10^4$ of induced neural stem cells were spread thereon. In 24 hours, the cells were fixed with 4% paraformaldehyde (PFA) for 20 minutes and then permeabilized with 0.3% Triton X-100 PBS for 10 minutes. The cells were blocked with 5% normal goat serum (NGS) for 1 hour and treated with primary antibodies at a concentration of 1:100 overnight. On the next day, the cells were incubated with secondary antibodies at a concentration of 1:1000 for 1 hour. Their nuclei were stained with DAPI and dried after mounting.

As a result, the SOX2-transduced iNSCs had a similar morphology to that of H9-derived NSC (H9-NSCs) and showed the expression of NSC-specific markers, such as PAX6, NESTIN, VIMENTIN, and SOX2 (FIGS. 1A to 1D and S1A).

Example 2

Analysis of miRNA Expression Profile in SOX2-Transduced hiNSCs

Example 2-1

MicroRNA Microarray Analysis

The total RNA was extracted from cells using Trizol reagent, and in order to produce fluorescence-labeled miR-NAs, 100 ng of the total RNA sample was labeled and hybridized using the Agilent miRNAs complete labeling and hybridization kit. The signals of the labeled miRNAs were scanned by Agilent microarray scanner. Raw data were extracted using the software (Agilent Feature Extraction Software (v11.0.1.1)) and analyzed and visualized using R statistical language v. 2.15.0.

Example 2-2

Results of Analysis of miRNA Expression Profile

The miRNA profiles of hDF, H9-NSCs, and SOX2-transduced hiNSCs were determined through the microarray analysis as in Example 2-1.

As a result, it was confirmed that the miRNA expression pattern of SOX2-transduced hiNSCs was more similar to that of H9-NSCs than that of hDFs (FIG. 1E).

Specifically, it was confirmed that the expression levels of neural lineage-specific miRNAs, such as miR-9-5p, miR-9-3p, and miR-124, which play key roles in the conversion of fibroblasts into functional neurons, were more up-regulated in H9-NSCs and SOX2-transduced hiNSCs than in hDFs.

Additionally, regarding let-7, which is known to play roles in the control of NSC maintenance and self-renewal, it was confirmed that the expression levels of the entire let-7/miR-98 family were more down-regulated in H9-NSCs and SOX2-transduced hiNSCs than in hDFs (FIGS. 1F and 1J).

However, significant alteration of expression of embryonic stem cell-specific miRNAs, the miR-302/367 family, was not detected between hDFs, H9-NSCs, and SOX2-transduced hiNSCs, whereas a significant expression was detected in human embryonic stem cells (hESCs).

Example 3

Analysis of iNSC Reprogramming Efficiency, Proliferation, and Self-Renewal by Let-7b

Example 3-1

Analysis of iNSC Reprogramming Efficiency by miRNA Activity

In order to confirm whether miRNA activity promotes reprogramming of hDFs to iNSCs, miR-9-5p, miR-9-3p, miR-124, anti-let-7b, let-7b, miR-CTL, and anti-miR-CTL were transfected during reprogramming with SOX2.

Specifically, miRNA was overexpressed using the commercially available hsa-let-7b (Invitrogen, PM11050), miR-124-3p (Invitrogen, PM10691), miR-9-5p (Invitrogen, PM10022), miR-9-3p (Invitrogen, PM13072), and anti-let-7b (Invitrogen, AM11050), and an appropriate pre-miRNA precursor-negative control (Invitrogen, AM17110) and anti-miRNA inhibitor-negative control (Invitrogen, AM17010) were used.

For the colony forming efficiency assay, $2\times10^4$ cells of SOX-2-transduced hDFs were seeded in a 24-well plate before transfection. The transfection was performed using 50 nM of hsa-let-7b, miR-124-3p, miR-9-5p, miR-9-3p, and anti-let-7b (day 0), and transfected again 3 days later (day 3).

As a result, it was confirmed that the SOX2-transduced hDFs were converted into neuron-like cells rather than NSC-like colonies. The efficiency of forming PAX6/NESTIN-positive colonies was reduced little or not changed at all in cells transfected with miR-124, miR-9-5p, or miR-9-3p, compared to the cells transfected with miR-CTL.

However, the overexpression of let-7b reduced the reprogramming efficiency, whereas the inhibition of let-7b increased the reprogramming efficiency by at least 3.5 times, compared to anti-miR-CTL (FIG. 11).

Example 3-2

Capability of hiNSCs Proliferation by Let-7b

In order to confirm whether miRNA let-7b controls the proliferation of hiNSCs, let-7b was transfected with SOX2-transduced hiNSCs, and the cell proliferation was measured by 5-bromo-2-deoxyuridine (BrdU) labeling of dividing cells.

Specifically, in order to measure the proliferation rate of cells, iNSCs were stained with 5-bromo-2-deoxyuridine (BrdU; Sigma) as described below. Briefly, 10 µM BrdU was added in a cell culture medium and incubated for 5 hours at 37° C. Then, the cells were washed with PBS and fixed with 4% PFA for 10 minutes at room temperature. For permeabilization, sodium citrate buffer were used for 15 minutes at 85° C. and the cells were incubated with blocking solution (5% NGS). The cells were then incubated overnight at 4° C. with BrdU primary antibodies diluted in the blocking solution (Abcam, Cambridge, Mass.). The cells were treated with secondary Alexa-488 antibodies for 1 hour. For staining the nuclei, DAPI was diluted to 1:1000 in PBS and incubated with the cells for 10 minutes. The images were captured with a confocal microscope (Eclipse TE200, Nikon, Tokyo, Japan).

As a result, it was confirmed that the percentage of BrdU-positive cells was reduced, and in particular, the transfection of let-7b reduced the proliferation of hiNSCs in a dose-dependent manner (FIGS. 6A and 6B).

Example 3-3

Self-Renewal Capability of hiNSCs by Let-7b

In order to confirm whether the let-7b regulates self-renewal of SOX2-transduced hiNSCs, neurosphere-forming assay was performed.

Specifically, after the treatment of miRNA, 2,000 cells were cultured in non-adherent culture dishes in order to form primary neurospheres. Primary neurosphere cells were dissociated into single cells using Accutase, then replated at clonal density in nonadherent cultures to form secondary neurospheres. The number and size of the secondary neurospheres were counted and measured after 7 days of culture.

As a result, it was confirmed that the size of the let-7b-transfected hiNSCs was smaller than that of the miR-CTL-transfected hiNSCs, and also that the increasing of let-7b during subcloning formed almost no secondary neurospheres (FIGS. 6C to 7E).

Example 4

Activation of hiNSC Reprogramming by Simultaneous Transduction of SOX/HMGA2

Because it was confirmed in Example 3 that let-7b overexpression reduced the hiNSC reprogramming efficiency, it was examined whether the overexpression of MYC and LIN28 (which are known to inhibit the expression of let-7b), and HMGA2 (whose expression is known to be inhibited by let-7b), can improve the hiNSC reprogramming efficiency.

Example 4-1

Confirmation of Cell Proliferation by HMGA2

In order to examine whether overexpressions of CMYC, LIN28, and HMGA2 in combination with SOX2 increase cell proliferation compared to overexpression of SOX2 alone, MTT assay was performed. Specifically, 1x10$^4$ cells were seeded in a 24-well plate. After 48 hours of incubation, 50 μL MTT stock solution (5 mg/mL) was added to the medium. After 4 hours of incubation at 37° C., the medium containing MTT solution was removed. DMSO was added in order to solubilize the formazan crystals, and then the solution was transferred to a 96-well plate. The absorbance at a wavelength of 540 nm was measured by EL800 microplate reader (BIO-TEK Instruments, Winooski, Vt.).

As a result, it was confirmed that, among them, HMGA2 has the least proliferation capability, and this was less than CMYC by 32%, and less than LIN28 by 17% (FIG. 2A).

Example 4-2

Confirmation of the Improvement of iNCS Reprogramming Efficiency by HMGA2

In order to confirm whether overexpressions of CMYC, LIN28, and HMGA2 in combination with SOX2 promote reprogramming of hiNSCs compared to overexpression of SOX2 alone, the efficiency of forming PAX6/NESTIN-positive colonies was measured for each case, respectively.

As a result, it was confirmed that the overexpression of HMGA2 along with SOX2 significantly increased the reprogramming efficiency of hiNSCs (FIG. 2C), and the simultaneous overexpression of SOX2/HMGA2 reduced the time required for forming PAX6/NESTIN-positive colonies from 17 days to 7.4 days (FIG. 2B).

Example 4-3

Confirmation of Change in Immunophenotype by HMGA2

In order to confirm whether the change in immunophenotype is induced at the early stage of reprogramming, fluorescence activated cell sorting (FACS) was confirmed.

As a result, it was observed that only the cells with SOX2/HMGA2 overexpression showed changes in cell population from CD44-positive to CD44-negative in about 10% of the total cells at 7 days after transfection, and simultaneously, about 7% of the cell population showed a shift from CD184-negative to CD184-positive (FIG. 2D).

The majority of hiNSCs and H9-NSCs showed CD44-negative and CD184-positive cell populations (FIG. 7A), and SOX2/HMGA2-transduced hiNSCs also showed similar morphological characteristics to those of SOX2-transduced hiNSCs and H9-NSCs, and expression of NSC-specific markers, such as PAX6, NESTIN, SOX2, Ki67, and HMGA2 (FIG. 2E).

Example 4-4

Evaluation of Reprogramming Level of Transcriptome by HMGA2

In order to evaluate the reprogramming level of transcriptome by HMGA2, comparative global gene expression data was analyzed by microarray analysis, and quantitative real-time PCR (qRT-PCR) was performed to evaluate the microarray data.

As a result, it was confirmed that the global genome heat map and pairwise scatter plots indicated that hiNSCs closely resembled the H9-NSCs but were different from the parental hDFs (FIGS. 7B and 7C). SOX2, HMGA2, PAX6, NESTIN, OLIG2, MSI1, and GLAST were induced in both SOX2- and SOX2/HMGA2-transduced iNSCs, and their expression levels were comparable with that of H9-NSCs (FIG. 2F).

Example 4-5

Analysis of Methylation State of SOX2 Promoter

In order to analyze the methylation state of SOX2 DNA in hDFs, H9-NSCs, and SOX2- and SOX2/HMGA2-transduced hiNSCs, unmethylated thymines were converted into cytosines using EZ DNA Methylation-Gold kit (Zymo Research, Irvine, Calif.).

Specifically, the unmethylated cytosines in CpG islands were converted into uracil via integration of heat-denaturation and sodium bisulfate treatment with a CT-conversion reagent. As the recovery of DNA following DNA bisulfite conversion, the converted DNA was desulfonated and subsequently cleaned and eluted. Then, the bisulfite-modified DNA was immediately amplified by PCR and stored at below −20° C. For the amplification of the bisulfite-converted DNA, primers were designed at MethPrimer (www.urogene.org/methprimer), and PCR was performed. The primer sequences are shown below:

```
Sox2 sense
                                        (SEQ ID NO: 1)
5'-GGGATATGATTAGTATGTATTTTTT-3', Sox2 antisense
                                        (SEQ ID NO: 2)
5'-AATTTTCTCCATACTATTTCTTACTCTCCT-3'
```

The produced PCR products were ligated with pGEM T-Easy Vector System I (Promega, Madison, Wis.). Then, the plasmid DNAs were cloned into bacteria (DH5α). Extracted plasmid DNA from the bacterial clones was analyzed via sequencing with the M13 reverse primer (5'-AGCGGATAACAATTTCACACAGGA-3') using an ABI 3730XL capillary DNA sequencer (Applied Biosystems). Subsequently, the methylated CpGs were represented by black circles, whereas the unmethylated CpGs were represented by white circles.

As a result, it was confirmed that SOX2 promoter was hypomethylated in hiNSCs similarly to H9-NSCs, suggesting that SOX2 was transcriptionally activated (FIG. 2G). Thus, it was confirmed that HMGA2 served the role as a chromatin modulator to promote hypomethylation of SOX2 promoter.

Conclusively, the Example suggests that HMGA2, as a let-7b target, significantly increased SOX2-induced reprogramming efficiency and time into hiNSCs, and SOX2/HMGA2-transduced hiNSCs showed similar characteristics to H9-NSCs at a cell surface marker signature, transcriptional level, methylation pattern, etc.

Example 5

Confirmation of Inhibition of Proliferation and Self-Renewal of hiNSCs by Down-Regulation of HMGA2

In order to confirm whether HMGA2 controls the proliferation of hiNSCs, hiNSCs were transfected with HMGA2-targeting siRNA (siHMGA2), and cell proliferation was measured by BrdU labeling of dividing cells, specifically, using commercially available siRNA (Dharmacon, ON Target plus SMART pool, Cat #L-013495-00-0005, Lafayette, Colo.) as an HMGA2 inhibitor, and non-targeting siRNA (Dharmacon, ON Target plus SMART pool, Cat # D-001810-01) as a control. The cells were seeded in a 24-well plate at a concentration of $1 \times 10^4$, and 50 nM siRNA was transfected with a Dharmafect transfection reagent (Dharmacon) added in culture media without antibiotics.

As a result, the down-regulation of HMGA2 dramatically reduced the percentage of BrdU-positive cells (FIGS. 8A and 8B). Additionally, it was confirmed that siHMGA2-transfected hiNSCs significantly reduced neurosphere size, and also reduced self-renewal, as confirmed by number and percentage of cells that can give rise to secondary neurospheres among primary neurospheres (FIGS. S4C to S4E). Taken together, it was suggested that the down-regulation of HMGA2 with an siRNA against HMGA2 inhibits proliferation and self-renewal of hiNSCs.

Example 6

Confirmation of Multipotency of hiNSCs

For neural differentiation, hiNSCs were seeded at a density of 1,000 on each of the poly-L-ornithine/fibronectin coated coverslips in a 24-well plate containing an iNSC maintenance medium (ReNcell NSC maintenance Media (Millipore)). After 24 hours, the medium was changed into Neurocult (Stem Cell Technology) for random differentiation. Following 1 week of Neurocult, the medium was replaced with three specific lineages' (neurons, astrocytes, and oligodendrocytes) induction media.

Meanwhile, after the induction of the differentiation, the iNSCs were confirmed with lineage-related markers via immunocytochemistry.

Example 6-1

Confirmation of Differentiation Potential into Neurons

As the neuronal induction medium, a 1:1 mixture between DMEM/F12 (Gibco BRL) and Neurobasal (Gibco BRL), which contains B27 (Gibco BRL), Gmax (Gibco BRL), retinoic acid (Sigma), ascorbic acid (Sigma), BDNF (Peprotech, Rocky Hill, N.J.), GDNF (Peprotech), and Forskolin (Sigma), was used.

As a result of the differentiation, 10 days to 15 days after the neuronal induction of SOX2/HMGA2-transduced hiNSCs, the expressions of immature neuronal markers, neuron-specific class III beta-tubulin (TUJ1), doublecortin (DCX), and neuronal intermediate filaments, α-internexin, and neurofilament (NF) were confirmed (FIG. 3A).

Additionally, as a result of clonal analysis for the evaluation of the self-renewal potential of the hiNSCs, it was confirmed that neuronal differentiation was induced and NF and α-internexin were stained in clones at multiple passages. After 10 days to 25 days of the neuronal induction, MAP2 (a mature neuronal marker), tyrosine hydroxylase (TH) (a dopaminergic and noradrenergic neuron marker), and choline acetyltransferase (ChAT) were expressed at a similar level compared to that of H9-NSCs (FIGS. 3A and 9A).

Example 6-2

Confirmation of Differentiation Potential into Astrocytes

As the medium of astrocytes induction, a DMEM (high glucose) medium containing N2 (Gibco BRL), Gmax, and 1% FBS was used.

As a result, it was confirmed that the SOX2/HMGA2-transduced hiNSCs produced glial fibrillary acidic protein (GFAP)-positive cells, thereby confirming the differentiation of the hiNSCs into astrocytes (FIG. 3A).

Example 6-3

Confirmation of Differentiation Potential into Oligodendrocytes

There are two different types of oligodendrocyte induction media. First, the cells were cultured in a DMEM/F12 medium supplemented with N2, MEM non-essential amino acids solution (MEM NEAA; Gibco BRL), heparin (Sigma), RA, SHH (Peprotech), and B27 for 2 weeks and then the medium was replaced with a DMEM/F12 medium supplemented with N2, B27, MEM NEAA, T3, cAMP (Sigma), PDGF (Peprotech), IGF (R&D), and NT3 (Sigma) for 2 weeks.

As a result, it was confirmed that O4- and OLIG2 (oligodendrocyte markers)-double positive cells were detected after 20 days to 35 days of induction toward oligodendroglial fate (FIG. 3A).

Example 7

Analysis of Electrophysiological Characteristics of hiNSCs

In order to evaluate the functionality of SOX2/HMGA2-transduced hiNSCs, the electrophysiological properties were tested through patch-clamp reading. Specifically, whole cell patch-clamp recordings in neurons derived from iNSCs were recorded using an EPC 10 USB amplifier (HEKA Elektronik, Lamprecht, Germany) at room temperature (22±1° C.). The recording chamber was filled with continuously flowing Tyrode solution (flow rate, 10 mL/min), and the patch electrodes were made of borosilicate glass capillaries by a PC-10 puller (Narishige Company). The resistance of the electrodes was 4 MΩ to 7 MΩ when it was filled with a pipette solution. Data were acquired and analyzed using Pulse program version 8.67 (HEKA Electronik) and Origin 6.1 software (MircoCal). The current was filtered at 3 kHz using a four-pole Bessels filter and digitized at 10 kHz. Tyrode solution contained 143 mM NaCl, 5.4 mM KCl, 0.5 mM $MgCl_2$, 1.8 mM $CaCl_2$, 0.5 mM $NaHPO_4$, 10 mM glucose, and 5 mM 4-(2 hydroethyl)-1-piperazineethanesulfonic acid (HEPES); and the pH was adjusted to 7.5 with NaOH. The pipette solution contained 150 mM KCl, 1.0 mM $MgCl_2$, 10 mM HEPES, 5 mM EGTA, 2 mM Mg-ATP, and the pH was adjusted to 7.2 with NaOH. Lidocaine (0.1%) was used for blocking the Na current.

As a result, it was confirmed that SOX2/HMGA2-transduced hiNSCs can generate various action potentials while giving rise to neurons which expressed sodium current. The sodium current (or internal current) and action potentials were inhibited by sodium channel blocker lidocaine and restored to normal status after washout (FIGS. 3B to 3D and 9B to 9D). These data suggest that the neurons differentiated from hiNSCs have the functional membrane properties and activities of normal neurons.

Example 8

Test of Differentiation and Survivability of hiNSCs in an Animal Model

Example 8-1

Transplantation of CMDiI-Labeled hiNSCs

SOX2/HMGA2-transduced hiNSCs were detached using Accutase and suspended in PBS. The hiNSCs were labeled with CM-DiI (molecular probes) for tracking after injection. The hiNSCs were incubated with CM-DiI in a 37° C. water bath for 15 minutes and then at 4° C. for 10 minutes. The CM-DiI labeled hiNSCs were suspended in PBS at a density of $1\times10^5$ cells/µL. The CM-DiI labeled hiNSCs were transplanted into the subventricular zone (SVZ) using the stereotaxic apparatus and the ultra-micropump (World Precision Instruments, Sarasota, Fla.). After transplantation, the scalp was closed by suture, and the animals were allowed to recover from anesthesia, thereby preparing 4-week-old mouse models.

Example 8-2

IHC Cryosection

Three weeks after the transplantation, brains were isolated from the mouse models and soaked in 4% PFA overnight, and then transferred to 30% sucrose for 48 hours. Then, the isolated brains were molded with an infiltration mixture (OCT compound; Sakura Finetek, Tokyo, Japan), kept at −70° C. overnight, and the cryosection was performed on a cryostat (CM 3050, Leica, Wetzlar, Germany). Specifically, tissues were incubated with 0.05% Triton X-100 for 20 minutes. The tissues were incubated with 5% NGS for blocking unspecific antibody binding. Then, the tissues were incubated with primary antibodies at a dilution ratio of 5% NGS overnight at 4° C. The tissues were incubated with secondary Alexa 488- or Alexa 594-labeled antibodies (1:1000) for 1 hour at room temperature. The nuclei were stained with DAPI for 10 minutes. The images were photographed using a confocal microscope (Nikon).

As a result, the transplanted cells were detected by immunostaining, and the detected cells were co-stained with markers of three different lineages. The immunostaining revealed that grafted hiNSCs were found to be positive for TUJ1 (neurons), GFAP (astrocytes), and MBP (oligodendrocytes), which are co-localized with CMDfl 1 fluorescence (FIGS. 3E and 9E). Taken together, it is suggested that the SOX2/HMGA2-transduced hiNSCs are able to survive and differentiate into neurons, astrocytes, and oligodendrocytes in vivo.

Example 9

Efficient Reprogramming of Various Somatic Cells into hiNSCs by HMGA2

Example 9-1 iNSC Reprogramming of hUCB-MSCs by HMGA2

Because human umbilical cord blood (hUCB) cells have advantages in that they can be obtained without invasiveness and retain minimal genetic mutations, it was evaluated whether hUCB can be used as a source for iNSC reprogramming.

Mesenchymal stem cell (MSC) populations were isolated from hUCB as described in Preparation Example 1. Following SOX2/HMGA2 transduction into hUCB-MSCs, hUCB-MSC-derived hiNSC colonies appeared at day 7 to day 12 after transfection, and they were immunocytochemically proven to be iNSCs positively stained with PAX6 and NESTIN (FIG. 4A). It has been reported that MSCs are positive for CD73 and CD105, but are negative for the hematopoietic markers CD34, CD45, and HLA-DR. The hUCB-MSC-derived hiNSCs were negative for CD73 and CD105, suggesting that cell surface marker signature had been changed (FIG. 10A).

Additionally, it was confirmed that the expression of HMGA2 was significantly higher in hUCB-MSCs compared to hDFs (FIG. 10B). The SOX2/HMGA2-transduced hUCB-MSCs gave rise to a 3- to 4-fold higher PAX6/NESTIN-positive colonies compared to SOX2-transduced hUCB-MSCs (FIG. 10C).

Example 9-2

Difference in Proliferation Capacity Between H9-NSCs and hiNSCs

In order to confirm the difference in proliferation capacity between H9-NSCs and hiNSCs from different cell sources and combination of transgenes, the proliferation rates of H9-NSCs and hiNSCs were measured by cumulative population doubling level analysis (CPDL). Specifically, the proliferation rates were determined by the entire cumulative population doubling level using the equation $CPDL=\ln(N_f/N_i)\ln 2$, wherein $N_i$ is the initial number of cells seeded, $N_f$ is the final number of harvested cells, and ln is the natural logarithm.

$5\times10^4$ cells were inoculated in triplicate on 6-well plates and subcultured every 4 days. In order to detect only the live cells, the final number of cells was counted using tryphan blue and $5\times10^4$ cells were inoculated again. For calculation of cumulative population doubling level, the population doubling for each passage was calculated and added to the population doubling level of the previous passage.

As a result, it was confirmed that there was no significant difference in proliferation capacity between H9-NSCs and hiNSCs cell lines, and this suggests that H9-NSCs and hiNSCs cell lines possess similar proliferation capacity (FIG. 10D).

Example 9-3

Confirmation of Induction Capability of Senescent hUCB-MSCs into Neural Stem Cells In order to study the role of let-7b/HMGA2 in reprogramming efficiency, it was examined whether senescent hUCU-MSCs can be induced into neural stem cells by transduction of SOX2 alone or in combination with let-7 targeting factors. To this end, senescent hUCB-MSCs, whose senescence was confirmed via senescence-associated (SA)-β-galactosidase assay, were transduced with SOX2, SOX2/CMYC, SOX2/LIN28, and SOX2/HMGA2 (FIG. 4B).

For the galactosidase assay, hUCB-MSCs were seeded in 6-well plate and incubated until the population reached 40% to 50%, washed with PBS twice, and fixed with 0.5% glutaldehyde in PBS for 5 minutes at room temperature. The cells were washed with PBS containing 1 mM $MgCl_2$ (pH 7.2) and incubated with X-gal solution (1 mg/mL X-gal, 0.12 mM $K_3Fe[CN]_6$ (potassium ferricyanide), 0.12 mM $K_4Fe[CN]_6$ (potassium ferrocyanide) and 1 mM $MgCl_2$ in PBS, pH 6.0) overnight at 37° C. On the next day, the images were photographed under a microscope (IX70, Olympus, Japan).

The combination between SOX2/CMYC and SOX2/LIN28 resulted in morphological changes but failed to generate hiNSC colonies, and only the SOX2/HMGA2 overexpression was apparently shown to promote the formation of hiNSC colonies (FIG. 4B). The SOX2/HMGA2 overexpression led to formation of 2 to 4 colonies from $1\times10^5$ senescent hUCB-MSCs (conversion efficiency of 0.004% to 0.008%), three weeks after the conversion (FIG. 4C).

Example 10

Reprogramming of hiNSCs by Umbilical Cord Blood $CD34^+$ Cells

Example 10-1

Isolation and Purification of Umbilical Cord Blood $CD34^+$ Cells

The isolation of $CD34^+$ cells was performed by CD34 microbead sorting system (MACS). Specifically, 50 μL of CD34 microBeads (#130-046-703, Miltenyi Biotech) was incubated with mononuclear cells (about $1\times10^8$) harvested from umbilical cord blood using Lymphoprep (ProteoGenix, Portland, Oreg.) density-gradient centrifugation at 2° C. to 8° C. for 30 minutes and thereby magnetically labeled the $CD34^+$ cells. The suspension of mononuclear cells was passed through the MACS sorter with a magnetic field after attaching a MACS column so that only magnetically labeled $CD34^+$ cells could be confined inside the column. After removing the column from the MACS sorter, the buffer solution was pushed away by pressing, thereby isolating the confined $CD34^+$ cells. $CD34^+$ cells were cultured in Iscove's modified Dulbecco's medium (IMDM) containing 10% FBS, 50 ng/mL SCF, 20 ng/mL IL-6, 50 ng/mL TPO, and 100 ng/mL Flt3.

The purification efficiency of $CD34^+$ cells was measured via flow cytometry using anti-CD34-FITC antibodies (Miltenyi Biotech), and as a result, it was confirmed that $CD34^+$ cells with 84.15% purity were isolated and purified (FIGS. 4E and 27).

Example 10-2

Confirmation of Reprogramming of hiNSCs by Umbilical Cord Blood $CD34^+$ Cells For the stimulation of cytokinesis, hUCB-$CD34^+$ cells were cultured with cytokines (SCF, Flt3L, TPO, and IL-6) for 3 days, and transduced with SOX2/HMGA2 by retrovirus (FIG. 4D). The cells were then plated on the feeder until 10 days to 14 days after the transduction, and iNSC colonies were observed under the NSC condition. The results of immunocytochemical staining revealed that hUCB-$CD34^+$ iNSCs had positive expressions of PAX6, SOX2, and NESTIN. Additionally, these hUCB-$CD34^+$ iNSCs were able to develop into neurons or astrocytes (FIG. 4F). SOX2 alone was sufficient to generate hUCB-$CD34^+$ iNSCs, but showed a very low efficiency. The hUCB-$CD34^+$ cells, which coexpress SOX2 and HMGA2, showed a 10- to 20-fold increase in the frequency of forming PAX6/NESTIN-positive colonies (FIG. 10E).

In summary, an efficient direct reprogramming by synergistic interaction between SOX2 and HMGA2 enables not only stem cells but also various somatic cells such as blood cells to be reprogrammed into hiNSCs.

Example 11

Confirmation of Increase of HMGA2 Protein Expression in Transfected hUCBSCs Cells

Example 11-1

Transfection for HMGA2 Overexpression

In order to verify the role of HMGA2 protein in differentiation and senescence of human umbilical cord blood-derived stromal cells (hUCBSCs), the hUCBSCs at the early stage for generations of 8 or less were transfected with HMGA2.

First, HMGA2 sequence was cloned into pMX retroviral vector. HMGA2 plasmid was transfected into 293T cells along with VSV-G and gag/pol plasmids. The viral suspensions were collected 48 hours and 72 hours after the transfection, and used to transfect hUCBSCs in the presence of 5 μg/mL Polybrene. The transduction efficiency was measured and shown to be 80% or higher, as shown in FIG. 12.

Example 11-2

Immunocytochemical Analysis

In human umbilical cord blood-derived stromal cells (hUCBSCs) at the early stage for generations of 8 or less transfected with HMGA2, prepared in Example 11-1, the increase of HMGA2 protein expression was confirmed by immunocytochemical analysis, and the results are shown in FIG. 13.

Example 11-3

Microarray

In human umbilical cord blood-derived stromal cells (hUCBSCs) at the early stage for generations of 8 or less transfected with HMGA2, prepared in Example 11-1, the increase of HMGA2 protein expression was confirmed by microarray analysis, and the results are shown in FIG. 14.

Example 11-4

Measurement of HMGA2 Expression Level According to the Progress of Subculture Passages In human umbilical cord blood-derived stromal cells (hUCBSCs) transduced with HMGA2, prepared in Example 11-1, the level of HMGA2 expression according to the progress of subcultures was confirmed by PCR.

According to the manufacturer's recommended protocol, total RNA was extracted using Trizol Reagent™ (Invitrogen, USA), and then oligo dT primer and Accupower RT premix (Bioneer, Korea) were added thereto to synthesize cDNA. PCR was performed according to the manufacturer's recommended protocol using the cDNA as a template, and the results are shown in FIG. 15. From the results of the PCR experiment, it was confirmed that the level of HMGA2 expression reduced as the subculture proceeded from the $6^{th}$ passage to the $20^{th}$ passage.

Example 12

Confirmation of Morphological Changes According to Progress of Subculture Passages In human umbilical cord blood-derived stromal cells (hUCBSCs) transduced with HMGA2, prepared in Example 11-1, the cellular morphology according to the progress of subculture passages were measured by phase contrast image, and the results are shown in FIG. 16.

From FIG. 16, it was confirmed that the human umbilical cord blood-derived stromal cells (hUCBSCs) became flatter and lengthier with the progress of the passages, whereas the morphological change in human umbilical cord blood-derived stromal cells (hUCBSCs) was mitigated.

Example 13

SA-b-Gal (Senescence Associated Beta-Galactosidase) Staining

In order to confirm the level of senescence of the human umbilical cord blood-derived stromal cells (hUCBSCs) transduced with HMGA2, prepared in Example 11-1, the level of senescence associated beta-galactosidase (SA-β-gal) expression according to the progress of subculture passages was measured by β-gal staining method, and the results are shown in FIG. 17.

From FIG. 17, it was confirmed that the human umbilical cord blood-derived stromal cells (hUCBSCs) reduced the level of senescence associated beta-galactosidase (SA-β-gal) expression.

Example 14

Cell Proliferation According to Subculture Passages

In human umbilical cord blood-derived stromal cells (hUCBSCs) transduced with HMGA2, prepared in Example 11-1, the level of cell proliferation according to the progress of subculture passages was measured by an MTT assay, and the results are shown in FIG. 18.

From FIG. 18, it was confirmed that the human umbilical cord blood-derived stromal cells (hUCBSCs) reduced less in the level of cell proliferation according to the progress of subculture passages, compared to that in controls.

Example 15

Evaluation of the Effect of HMGA2 on PI3K/AKT Pathway

Example 15-1

Confirmation of Related Genes

In human umbilical cord blood-derived stromal cells (hUCBSCs) transduced with HMGA2, prepared in Example 11-1, the HMGA2 overexpression-related signaling pathway-associated genes and molecular cellular function related gene were specified by ingenuity pathway analysis (IPA) software, and the results are shown in FIG. 19.

From FIG. 19, it was confirmed that elF4 and p70S6K signals, which are related to transcriptional control, were expressed abundantly, and that mTOR and PI3K/AKT signal pathways, which are related to elF4 and p70S6K, were expressed abundantly.

Example 15-2

Western Blot

In human umbilical cord blood-derived stromal cells (hUCBSCs) transduced with HMGA2, prepared in Example 11-1, a Western blot was performed to evaluate the effect of HMGA2 overexpression on PI3K/AKT pathway and mTOR/p70s6K.

The Western blot analysis was performed on (i) hUCBSCs in which HMGA2 is overexpressed, (ii) hUCBSCs in which LY294002-treated HMGA2 is overexpressed, and (iii) GFP as a comparative example.

Specifically, the cells were pulverized in 50 mM Tris-HCl buffer containing 1 mM phenylmethylsulfonyl fluoride, 1 mM aprotinin, 1 mM leupeptin, 1 mM antipain, and 0.1 mM sodium orthovanadate. The protein content was confirmed by DC assay kit (Bio-Rad, USA), and SDS-PAGE was performed by loading a certain amount of proteins on a 10% to 15% polyacrylamide gel, and the proteins were transferred to a nitrocellulose membrane at 50 V and 350 mA for 5 hours. All antibodies were used according to the manufacturer's instruction, and the protein bands were confirmed by enhanced chemiluminescence detection kit (Amersham Pharmacia Biotech, Buckinghamshire, UK), and the results are shown in FIG. 20.

From FIG. 20, it was confirmed that the phosphorylation of AKT, mTOR, and p70S6K were induced by HMGA2, and when treated with LY294002 there was no change in the amount of total protein expression, but the phosphorylation of AKT, mTOR, and p70S6K were inhibited.

Although the expression levels of $p16^{INK4A}$ and $p21^{CIP1}$/WAF1 were inhibited by HMGA2, the expression levels were recovered by LY294002 treatment, and thus the PI3K/AKT/mTOR/p70S6K pathways are suitable for reducing the expression levels of $p16^{INK4A}$ and $p21^{CIP1}$/WAF1.

Additionally, it was confirmed that the HMGA2 overexpression activates the PI3K/AKT/mTOR/p70S6K pathways and inhibits the expression of $p16^{INK4A}$ and $p21^{CIP1}$/WAF1.

Example 16

Confirmation of Morphological Change According to the Progress of Subculture Passages by HMGA2 Inhibition In order to verify the role of HMGA2 protein in differentiation and senescence of human umbilical cord blood-derived stromal cells (hUCBSCs), the HMGA2 expression in hUCBSCs at early stage for generations of 8 or less was inhibited using siRNA.

In the human umbilical cord blood-derived stromal cells (hUCBSCs) where HMGA2 expression was inhibited, the cell morphology according to the progress of subculture passages was measured by phase contrast image, and the results are shown in FIG. 21. That is, it was confirmed that the human umbilical cord blood-derived stromal cells (hUCBSCs), where HMGA2 expression was inhibited, became flatter and lengthier.

Example 17

Measurement of Expression Level of Senescence Associated Beta-Galactosidase (SA-β-Gal) by HMGA2 Inhibition In order to confirm the senescence level of the human umbilical cord blood-derived stromal cells (hUCBSCs) where HMGA2 expression was inhibited, the expression level of senescence associated beta-galactosidase (SA-β-gal) was measured by β-gal staining, and the results are shown in FIG. 21.

It was confirmed that the hUCBSCs transduced with HMGA2 increased the expression level of senescence associated beta-galactosidase (SA-β-gal).

Example 18

Confirmation of the Effect of Subculture Passages on Cell Proliferation

In the human umbilical cord blood-derived stromal cells (hUCBSCs) where HMGA2 expression was inhibited, the cell proliferation according to the progress of subculture passages were measured by an MTT assay, and the results are shown in FIG. 22. From FIG. 22, it was confirmed that the HMGA2-inhibited hUCBSCs significantly reduced cell proliferation according to the progress of subculture passages.

Example 19

Western Blot

In the human umbilical cord blood-derived stromal cells (hUCBSCs), in order to evaluate the effect of HMGA2 inhibition on PI3K/AKT pathways and mTOR/p70s6K, Western blots were performed and the results are shown in FIG. 23.

From FIG. 23, it was confirmed that the phosphorylation of AKT, mTOR, and p70S6K were drastically reduced, whereas the expression levels of $p16^{INK4A}$ and $p21^{CIP1}$/WAF1 increased. From these results, it was confirmed that the HMGA2 inhibition inhibits the PI3K/AKT/mTOR/p70S6K pathways while increasing the expression of $p16^{INK4A}$ and $p21^{CIP1}$/WAF1.

Based on the results of Example 15-2 and Example above, the signaling pathway of the human umbilical cord blood-derived stromal cells (hUCBSCs) by the HMGA2 protein expression is shown in FIG. 24.

Example 20

Measurement of Differentiation Potential into Adipose Tissues

The differentiation potential of the HMGA2-inhibited human umbilical cord blood-derived stromal cells (hUCBSCs) was measured.

In order to figure out the differentiation level based on the accumulated fats present in the cells, the cultured cells were stained with Oil Red O, and the Oil Red O penetrated into the cells were extracted again using 100% isopropyl alcohol and quantitated at OD 500 by ELISA plate reader (EL800, Bio-Tek Instruments, USA). The results are shown in FIG. 25.

From FIG. 25, it was confirmed that the Oil Red O-stained percentage of the HMGA2-inhibited human umbilical cord blood-derived stromal cells (hUCBSCs) was lower than that of the control group, and the expression rates of genes associated with fat cell differentiation, such as PPARr, aP2, and C/EBP-b, were rapidly decreased.

Example 21

Screening of HMGA2 Control-Related Genes and PCR

The gene expression in HMGA2-overexpressing human umbilical cord blood-derived stromal cells (hUCBSCs) prepared in Example 11-1 and the gene expression in HMGA2-inhibited human umbilical cord blood-derived stromal cells (hUCBSCs) prepared in Example 7 were compared as shown in FIG. 26.

Based on the results of FIG. 26, the three genes of Cyclin F, Cyclin E1, and CDC25A, whose expression levels increase when HMGA2 is overexpressed while the expression levels decrease when HMGA2 is inhibited, were selected, and also five genes of C14orf153, EID2B, ZNF394, CDKN2AIPNL, and C9orf80, whose expression levels decrease when HMGA2 is overexpressed while the expression levels increase when HMGA2 is inhibited, were selected. The thus-selected eight genes were subjected to PCR and the results are shown in FIG. 27.

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

What is claimed is:

1. A method tor direct reprograming of a non-neuronal cell into a neural stern cell, said method comprising;
   (a) transducing or infecting a mammalian non-neuronal cell with a viral vector comprising a nucleic acid encoding a SOX2 protein and a nucleic acid encoding a High Mobility Group AT-hook 2 (HMGA2) protein to express SOX2 protein and HMGA2 protein, wherein said cell is cultured in a cell culture medium; and
   (b) culturing the cells expressing SOX2 protein and HMGA2 protein from step (a) in a neuronal stem cell culture medium for a period of time sufficient to obtain, neural stem cell-like colonies containing neural stem cells expressing Pax6 and Nestin, thereby directly reprogramming the non-neuronal cell into a neuronal stem cell,
   wherein overexpression of SOX2 and HMGA2 increased the reprogramming efficiency of the neural stem cells compared to the overexpression of SOX2 alone or HMGA2 alone, and
   wherein the non-neuronal cell is selected from the group consisting of a human dermal fibroblast, an umbilical blood cell derived stem cell and a blood cell.

2. The method of claim 1, further comprising:
   (c) separating neural stem cell-like colonies from the culture obtained in step (b).

3. The method of claim 1, wherein step (a) is performed by adding, to the culture medium for the non-neuronal cell a viral vector comprising a nucleic acid encoding a SOX2 protein and a nucleic acid encoding a High Mobility Group AT-hook 2 (HMGA2) protein.

4. The method of claim 1, wherein the non-neuronal cell is derived from humans.

5. The method of claim 1, wherein step (a) is performed by adding directly to the non-neuronal cell, a viral vector comprising a nucleic acid encoding a SOX2 protein and a nucleic acid encoding a High Mobility Group AT-hook 2 (HMGA2) protein.

* * * * *